US012655458B2

(12) United States Patent
Liu et al.

(10) Patent No.: US 12,655,458 B2
(45) Date of Patent: Jun. 16, 2026

(54) METHODS FOR CYCLIZATION OF (POLY)PEPTIDES COMPRISING $N^{\gamma}$-HYDROXY- OR $N^{\gamma}$-AMINO-L-ASPARAGINE

(71) Applicant: NANYANG TECHNOLOGICAL UNIVERSITY, Singapore (SG)

(72) Inventors: Chuan Fa Liu, Singapore (SG); Yiyin Xia, Singapore (SG); James P. Tam, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 462 days.

(21) Appl. No.: 18/548,832

(22) PCT Filed: Mar. 7, 2022

(86) PCT No.: PCT/SG2022/050117
§ 371 (c)(1),
(2) Date: Sep. 1, 2023

(87) PCT Pub. No.: WO2022/186782
PCT Pub. Date: Sep. 9, 2022

(65) Prior Publication Data

US 2024/0167070 A1 May 23, 2024

(30) Foreign Application Priority Data

Mar. 5, 2021 (SG) ............................ 10202102295S

(51) Int. Cl.
*C12P 21/02* (2006.01)
*C07K 7/64* (2006.01)

(52) U.S. Cl.
CPC ................ *C12P 21/02* (2013.01); *C07K 7/64* (2013.01)

(58) Field of Classification Search
CPC .................................. C12P 21/02; C07K 7/64
See application file for complete search history.

(56) References Cited

U.S. PATENT DOCUMENTS

2012/0244575 A1 9/2012 Poth et al.

FOREIGN PATENT DOCUMENTS

WO WO 2020226572 A1 11/2020

OTHER PUBLICATIONS

Abe et al., "Asparaginyl Endopeptidase of Jack Bean Seeds," The Journal of Biological Chemistry 268:3525-3529, Feb. 1993. (5 pages).

Altschul et al., "Basic Local Alignment Search Tool," J. Mol. Biol. 215:403-410, Oct. 1990. (8 pages).

Altschul et al., "Gapped BLAST and PSI-BLAST: a new generation of protein database search programs," *Nucleic Acids Research* 25(17):3389-3402, Sep. 1997. (14 pages).

Avrutina et al., "Trypsin inhibition by macrocyclic and open-chain variants of the squash inhibitor MCoTI-II," *Biol. Chem.* 386:1301-1306, Dec. 2005. (6 pages).

Baeriswyl et al., "Polycyclic Peptide Therapeutics," *ChemMedChem* 8:377-384, Mar. 2013. (8 pages).

Berjanskii et al., "PREDITOR: a web server for predicting protein torsion angle restraints," *Nucleic Acids Research* 34:W63-W69, Jul. 2006. (7 pages).

Bernath-Levin et al., "Peptide Macrocyclization by a Bifunctional Endoprotease," *Chemistry & Biology* 22:571-582, May 2015. (13 pages).

Bi et al., "Enzymatic Engineering of Live Bacterial Cell Surfaces Using Butelase I," *Angew. Chem. Int. Ed.* 56:7822 -7825, Jun. 2017. (4 pages).

Brooks et al., "Localization of Matrix Metalloproteinase MMP-2 to the Surface of Invasive Cells by Interaction with Integrin $\alpha v\beta 3$," *Cell* 85:683-693, May 1996. (11 pages).

Camarero et al., "Biosynthesis of a Fully Functional Cyclotide inside Living Bacterial Cells," *ChemBioChem* 8:1363-1366, Aug. 2007. (4 pages).

Cao et al., "Butelase-mediated synthesis of protein thioesters and its application for tandem chemoenzymatic ligation†," Chem. Commun. 51:17289-17292, Oct. 2015. (4 pages).

Conibear et al., "The Cyclic Cystine Ladder of Theta-Defensins as a Stable, Bifunctional Scaffold: A Proof-of-Concept Study Using the Integrin-Binding RGD Motif.," *ChemBioChem* 15:451-459, Feb. 2014. (9 pages).

D'Souza et al., "Using the MCoTI-II Cyclotide Scaffold To Design a Stable Cyclic Peptide Antagonist of SET, a Protein Overexpressed in Human Cancer," *Biochemistry* 55:396-405, Dec. 2015. (10 pages).

Daly et al., "Structural Insights into the Role of the Cyclic Backbone in a Squash Trypsin Inhibitor*," *The Journal of Biological Chemistry* 288(50):36141-36148, Dec. 2013. (8 pages).

Du et al., "A bifunctional asparaginyl endopeptidase efficiently catalyzes both cleavage and cyclization of cyclic trypsin inhibitors," *Nature Communications* 11:1575, Mar. 2020. (11 pages).

Emery et al., "Periodate Oxidation of Hydroxylamine Derivatives. Products, Scope and Application1," Contribution from the Department of Biochemistry, University of California, Berkeley 4, California, vol. 82, pp. 4903-4904, Sep. 1960. (2 pages).

Fosgerau et al., "Peptide therapeutics: current status and future directions," *Drug Discovery Today* 20(1):122-128, Jan. 2015. (7 pages).

(Continued)

*Primary Examiner* — Amber D Steele
(74) *Attorney, Agent, or Firm* — Seed Intellectual Property Law Group LLP

(57) ABSTRACT

The present invention relates to methods that employ enzymes having Asn-specific cyclase activity as a means for generating cyclic (poly)peptides from (poly)peptides that comprise a ligation motif comprising a $N^{\gamma}$-hydroxy-L-asparagine or $N^{\gamma}$-amino-L-asparagine residue. Further encompassed are the resulting cyclic (poly)peptides and the corresponding uses.

16 Claims, 24 Drawing Sheets

Specification includes a Sequence Listing.

(56) References Cited

OTHER PUBLICATIONS

Gran et al., "*Oldenlandia affinis* (R&S) DC A plant containing uteroactive peptides used in African traditional medicine," *Journal of Ethnopharmacology* 70:197-203, Jun. 2000. (7 pages).
Güntert et al., "Torsion Angle Dynamics for NMR Structure Calculation with the New Program DYANA," *J. Mol. Biol.* 273:283-298, Oct. 1997. (16 pages).
Harris et al., "A suite of kinetically superior AEP ligases can cyclise an intrinsically disordered protein," *Scientific Reports* 9(10820), Jul. 2019 [Published online Jul. 2019]. (13 pages).
Harris et al., "Efficient backbone cyclization of linear peptides by a recombinant asparaginyl endopeptidase," *Nature Communications* 6:10199, Dec. 2015. (10 pages).
Hashimoto et al., "Structural Basis for Matrix Metalloproteinase-2 (MMP-2)-selective Inhibitory Action of β-Amyloid Precursor Protein-derived Inhibitor*," *The Journal of Biological Chemistry* 286(38):33236-33243, Sep. 2011. (8 pages).
Hemu et al., "Ligase-Controlled Cyclo-oligomerization of Peptides," *Org. Lett* 21:2029-2032, Feb. 2019. (4 pages).
Hemu et al., "Structural determinants for peptide-bond formation by asparaginyl ligases," PNAS 116(24):11737-11746, Jun. 2019. (10 pages).
Hemu et al., "Total Synthesis of Circular Bacteriocins by Butelase 1," *J. Am. Chem. Soc.* 138:6968-6971, May 2016. (4 pages).
Hemu et al., "Turning an Asparaginyl Endopeptidase into a Peptide Ligase," ACS Catal. 10:8825-8834, Jul. 2020. (10 pages).
Hernandez et al., "Squash Trypsin Inhibitors from *Momordica cochinchinensis* Exhibit an Atypical Macrocyclic Structure†," *Biochemistry* 39:5722-5730, May 2000 [Published online Apr. 2000]. (9 pages).
Hider et al., "Origin of the positive 225-230 nm circular dichroism band in proteins Its application to conformational analysis," *Biophysical Chemistry* 31:45-51, Aug. 1988. (7 pages).
Higashi et al., "Identification of a Region of ß-Amyloid Precursor Protein Essential for Its Gelatinase A Inhibitory Activity*," *The Journal of Biological Chemistry* 278(16):14020-14028, Apr. 2003. (9 pages).
Higashi et al., "Molecular Design of a Highly Selective and Strong Protein Inhibitor against Matrix Metalloproteinase-2 (MMP-2)*," The Journal of Biological Chemistry 268(13):9066-9076, Mar. 2013. (11 pages).
James et al., "The macrocyclizing protease butelase 1 remains autocatalytic and reveals the structural basis for ligase activity," *The Plant Journal* 98:988-999, Jun. 2019 [Published online Feb. 2019]. (12 pages).
Lau et al., "Therapeutic peptides: Historical perspectives, current development trends, and future directions," *Bioorganic & Medicinal Chemistry* 26:2700-2707, Jun. 2018 [Published online Jul. 2017]. (8 pages).
Lee et al., "NMRFAM-SPARKY: enhanced software for biomolecular NMR spectroscopy," *Bioinformatics* 31(8):1325-1327, Apr. 2015. (3 pages).
Luckett et al., "High-Resolution Structure of a Potent, Cyclic Proteinase Inhibitor from Sunflower Seeds," *J. Mol. Biol.* 290:525-533, Jul. 1999. (9 pages).
Maola et al., "Engineered Peptide Macrocycles Can Inhibit Matrix Metalloproteinases with High Selectivity," *Angew. Chem. Int. Ed.* 58:11801-11805, Aug. 2019. (5 pages).
Min et al., "In vitro splicing of concanavalin A is catalyzed by asparaginyl endopeptidase," *Structural Biology* 1(8):502-504, Aug. 1994. (3 pages).
Muri et al., "Hydroxamic Acids as Pharmacological Agents," Current Medicinal Chemistry 9:1631-1653, Sep. 2002. (23 pages).
Nguyen et al., "Butelase 1 is an Asx-specific ligase enabling peptide macrocyclization and synthesis," *Nature Chemical Biology* 10:732-740, Sep. 2014. (9 pages).
Nguyen et al., "Butelase-mediated cyclization and ligation of peptides and proteins," *Nature Protocols* 11(10):1977-1988, Oct. 2016. (12 pages).
Nguyen et al., "Butelase-Mediated Macrocyclization of d-Amino-Acid-Containing Peptides," *Angew. Chem. Int. Ed.* 55:12802-12806, Oct. 2016. (5 pages).
Pfaff et al., "Selective Recognition of Cyclic RGD Peptides of NMR Defined; Conformation by ?IIb?3, aV?3, and ?5?1 Integrins," The Journal of Biological Chemistry 269(32):20233-20238, Aug. 1994. (6 pages).
Rehm et al., "Site-Specific Sequential Protein Labeling Catalyzed by a Single Recombinant Ligase," *J. Am. Chem. Soc.* 141:17388-17393, Oct. 2019. (6 pages).
Saska et al., "An Asparaginyl Endopeptidase Mediates in Vivo Protein Backbone Cyclization*," *The Journal of Biological Chemistry* 282(40):29721-29728, Oct. 2007. (8 pages).
Stanger et al., "Backbone cyclization of a recombinant cystine-knot peptide by engineered Sortase A," *FEBS Letters* 588:4487-4496, Nov. 2014 [Published online Oct. 2014]. (10 pages).
Tam et al., "Peptide asparaginyl ligases-renegade peptide bond makers," Sci China Chem 63(3):296-307, Feb. 2020. (12 pages).
Thongyoo et al., "Chemical and biomimetic total syntheses of natural and engineered MCoTI cyclotides," *Org. Biomol. Chem.* 6:1462-1470, Apr. 2008 [Published online Mar. 2008]. (9 pages).
Thongyoo et al., "Total synthesis of the macrocyclic cysteine knot microprotein MCoTI-II†," *Chem. Commun.*:2848-2850, Jun. 2006. (3 pages).
Trabi et al., "Three-Dimensional Structure of RTD-1, a Cyclic Antimicrobial Defensin from Rhesus Macaque Leukocytes†,‡," *Biochemistry* 40:4211-4221, Apr. 2001 [Published online Mar. 2001]. (11 pages).
Vinogradov et al., "Macrocyclic Peptides as Drug Candidates: Recent progress and Remaining Challenges," *J. Am. Chem. Soc.* 141:4167-4181, Feb. 2019. (15 pages).
Wishart et al., "1H, 13C and random coil NMR chemical shifts of the common amino acids. I. Investigations of nearest-neighbor effects," *Journal of Biomolecular NMR* 5:67-81, Jan. 1995. (15 pages).
Xia et al., "Ng-Hydroxyasparagine: A Multifunctional Unnatural Amino Acid That is a Good P1 Substrate of Asparaginyl Peptide Ligases," *Angew. Chem. Int. Ed.* 60:22207-22211, Oct. 2021. (5 pages).
Yoganathan et al., "An efficient chemical synthesis of carboxylate-isostere analogs of daptomycin†," *Org. Biomol. Chem* 11:4680-4685, Jul. 2013. (6 pages).
Zauner et al., "Structural analyses of *Arabidopsis thaliana* legumain γ reveal differential recognition and processing of proteolysis and ligation substrates," *J. Biol. Chem.* 293(23):8934-8946, Jun. 2018. (13 pages).
Zheng et al., "Synthesis of Cyclic Peptides and Cyclic Proteins via Ligation of Peptide Hydrazides," *ChemBioChem* 13:542-546, Mar. 2012. (5 pages).

```
                              SEQUENCE LISTING


<160> NUMBER OF SEQ ID NOS: 45

<210> SEQ ID NO 1
<211> LENGTH: 269
<212> TYPE: PRT
<213> ORGANISM: Artificial
<220> FEATURE:
<223> OTHER INFORMATION: VyPAL2 core domain

<400> SEQUENCE: 1

Asp Ser Ile Gly Thr Arg Trp Ala Val Leu Ile Ala Gly Ser Lys Gly
1               5                   10                  15

Tyr His Asn Tyr Arg His Gln Ala Asp Val Cys His Met Tyr Gln Ile
            20                  25                  30

Leu Arg Lys Gly Gly Val Lys Asp Glu Asn Ile Ile Val Phe Met Tyr
        35                  40                  45

Asp Asp Ile Ala Tyr Asn Glu Ser Asn Pro Phe Pro Gly Ile Ile Ile
    50                  55                  60

Asn Lys Pro Gly Gly Glu Asn Val Tyr Lys Gly Val Pro Lys Asp Tyr
65                  70                  75                  80

Thr Gly Glu Asp Ile Asn Asn Val Asn Phe Leu Ala Ala Ile Leu Gly
                85                  90                  95

Asn Lys Ser Ala Ile Ile Gly Gly Ser Gly Lys Val Leu Asp Thr Ser
            100                 105                 110

Pro Asn Asp His Ile Phe Ile Tyr Tyr Ala Asp His Gly Ala Pro Gly
        115                 120                 125

Lys Ile Gly Met Pro Ser Lys Pro Tyr Leu Tyr Ala Asp Asp Leu Val
    130                 135                 140

Asp Thr Leu Lys Gln Lys Ala Ala Thr Gly Thr Tyr Lys Ser Met Val
145                 150                 155                 160

Phe Tyr Val Glu Ala Cys Asn Ala Gly Ser Met Phe Glu Gly Leu Leu
                165                 170                 175

Pro Glu Gly Thr Asn Ile Tyr Ala Met Ala Ala Ser Asn Ser Thr Glu
            180                 185                 190

Gly Ser Trp Ile Thr Tyr Cys Pro Gly Thr Pro Asp Phe Pro Pro Glu
        195                 200                 205
```

-continued

```
Phe Asp Val Cys Leu Gly Asp Leu Trp Ser Ile Thr Phe Leu Glu Asp
    210                 215                 220

Cys Asp Ala His Asn Leu Arg Thr Glu Thr Val His Gln Gln Phe Glu
225                 230                 235                 240

Leu Val Lys Lys Lys Ile Ala Tyr Ala Ser Thr Val Ser Gln Tyr Gly
                245                 250                 255

Asp Ile Pro Ile Ser Lys Asp Ser Leu Ser Val Tyr Met
            260                 265


<210> SEQ ID NO 2
<211> LENGTH: 281
<212> TYPE: PRT
<213> ORGANISM: Artificial
<220> FEATURE:
<223> OTHER INFORMATION: butelase-1 active fragment

<400> SEQUENCE: 2

Val Glu Gly Thr Arg Trp Ala Val Leu Val Ala Gly Ser Lys Gly Tyr
1               5                   10                  15

Val Asn Tyr Arg His Gln Ala Asp Val Cys His Ala Tyr Gln Ile Leu
            20                  25                  30

Lys Lys Gly Gly Leu Lys Asp Glu Asn Ile Ile Val Phe Met Tyr Asp
        35                  40                  45

Asp Ile Ala Tyr Asn Glu Ser Asn Pro His Pro Gly Val Ile Ile Asn
    50                  55                  60

His Pro Tyr Gly Ser Asp Val Tyr Lys Gly Val Pro Lys Asp Tyr Val
65                  70                  75                  80

Gly Glu Asp Ile Asn Pro Pro Asn Phe Tyr Ala Val Leu Leu Ala Asn
                85                  90                  95

Lys Ser Ala Leu Thr Gly Thr Gly Ser Gly Lys Val Leu Asp Ser Gly
            100                 105                 110

Pro Asn Asp His Val Phe Ile Tyr Tyr Thr Asp His Gly Gly Ala Gly
        115                 120                 125

Val Leu Gly Met Pro Ser Lys Pro Tyr Ile Ala Ala Ser Asp Leu Asn
    130                 135                 140

Asp Val Leu Lys Lys Lys His Ala Ser Gly Thr Tyr Lys Ser Ile Val
145                 150                 155                 160

Phe Tyr Val Glu Ser Cys Glu Ser Gly Ser Met Phe Asp Gly Leu Leu
                165                 170                 175

Pro Glu Asp His Asn Ile Tyr Val Met Gly Ala Ser Asp Thr Gly Glu
            180                 185                 190

Ser Ser Trp Val Thr Tyr Cys Pro Leu Gln His Pro Ser Pro Pro Pro
        195                 200                 205

Glu Tyr Asp Val Cys Val Gly Asp Leu Phe Ser Val Ala Trp Leu Glu
    210                 215                 220

Asp Cys Asp Val His Asn Leu Gln Thr Glu Thr Phe Gln Gln Gln Tyr
225                 230                 235                 240

Glu Val Val Lys Asn Lys Thr Ile Val Ala Leu Ile Glu Asp Gly Thr
                245                 250                 255

His Val Val Gln Tyr Gly Asp Val Gly Leu Ser Lys Gln Thr Leu Phe
            260                 265                 270

Val Tyr Met Gly Thr Asp Pro Ala Asn
        275                 280


<210> SEQ ID NO 3
<211> LENGTH: 483
```

-continued

<212> TYPE: PRT
<213> ORGANISM: Viola yedoensis

<400> SEQUENCE: 3

```
Met Gln Leu Phe Ala Ala Gly Val Ile Leu Phe Phe Leu Leu Ala Leu
1               5                   10                  15

Ser Gly Thr Ile Ala Gly Gly Leu Asp Val Asp Ser Leu Gln Leu Pro
            20                  25                  30

Ser Glu Ala Ala Lys Phe Phe His Asn Asp Asn Ser Thr Asn Asp Asp
        35                  40                  45

Asp Ser Ile Gly Thr Arg Trp Ala Val Leu Ile Ala Gly Ser Lys Gly
    50                  55                  60

Tyr His Asn Tyr Arg His Gln Ala Asp Val Cys His Met Tyr Gln Ile
65                  70                  75                  80

Leu Arg Lys Gly Gly Val Lys Asp Glu Asn Ile Ile Val Phe Met Tyr
                85                  90                  95

Asp Asp Ile Ala Tyr Asn Glu Ser Asn Pro Phe Pro Gly Ile Ile Ile
            100                 105                 110

Asn Lys Pro Gly Gly Glu Asn Val Tyr Lys Gly Val Pro Lys Asp Tyr
        115                 120                 125

Thr Gly Glu Asp Ile Asn Asn Val Asn Phe Leu Ala Ala Ile Leu Gly
    130                 135                 140

Asn Lys Ser Ala Ile Ile Gly Gly Ser Gly Lys Val Leu Asp Thr Ser
145                 150                 155                 160

Pro Asn Asp His Ile Phe Ile Tyr Tyr Ala Asp His Gly Ala Pro Gly
                165                 170                 175

Lys Ile Gly Met Pro Ser Lys Pro Tyr Leu Tyr Ala Asp Asp Leu Val
            180                 185                 190

Asp Thr Leu Lys Gln Lys Ala Ala Thr Gly Thr Tyr Lys Ser Met Val
        195                 200                 205

Phe Tyr Val Glu Ala Cys Asn Ala Gly Ser Met Phe Glu Gly Leu Leu
    210                 215                 220

Pro Glu Gly Thr Asn Ile Tyr Ala Met Ala Ala Ser Asn Ser Thr Glu
225                 230                 235                 240

Gly Ser Trp Ile Thr Tyr Cys Pro Gly Thr Pro Asp Phe Pro Pro Glu
                245                 250                 255

Phe Asp Val Cys Leu Gly Asp Leu Trp Ser Ile Thr Phe Leu Glu Asp
            260                 265                 270

Cys Asp Ala His Asn Leu Arg Thr Glu Thr Val His Gln Gln Phe Glu
        275                 280                 285

Leu Val Lys Lys Lys Ile Ala Tyr Ala Ser Thr Val Ser Gln Tyr Gly
    290                 295                 300

Asp Ile Pro Ile Ser Lys Asp Ser Leu Ser Val Tyr Met Gly Thr Asp
305                 310                 315                 320

Pro Ala Asn Asp Asn Arg Thr Phe Val Asp Glu Asn Ser Leu Arg Pro
                325                 330                 335

Pro Leu Lys Val Ile His Gln His Asp Ala Asp Leu Tyr His Ile Trp
            340                 345                 350

Cys Lys Tyr Asn Met Ala Pro Glu Gly Ser Ser Lys Lys Ile Glu Ala
        355                 360                 365

Gln Lys Gln Leu Leu Glu Leu Met Ser His Arg Ala His Val Asp Asn
    370                 375                 380

Ser Ile Thr Leu Ile Gly Lys Leu Leu Phe Gly Val Asn Lys Ala Ser
385                 390                 395                 400
```

-continued

Lys Val Leu Asn Thr Val Arg Pro Val Gly Gln Pro Leu Val Asp Asp
405 410 415

Trp Gln Cys Leu Lys Ala Met Ile Arg Thr Phe Glu Thr His Cys Gly
420 425 430

Ser Leu Ser Glu Tyr Gly Met Lys His Thr Leu Ser Phe Ala Asn Met
435 440 445

Cys Asn Ala Gly Ile Gln Lys Glu Gln Leu Ala Glu Ala Ala Ala Gln
450 455 460

Ala Cys Val Thr Phe Pro Ser Asn Pro Tyr Ser Ser Leu Ala Glu Gly
465 470 475 480

Phe Ser Ala

<210> SEQ ID NO 4
<211> LENGTH: 482
<212> TYPE: PRT
<213> ORGANISM: Clitoria ternatea

<400> SEQUENCE: 4

Met Lys Asn Pro Leu Ala Ile Leu Phe Leu Ile Ala Thr Val Val Ala
1 5 10 15

Val Val Ser Gly Ile Arg Asp Asp Phe Leu Arg Leu Pro Ser Gln Ala
20 25 30

Ser Lys Phe Phe Gln Ala Asp Asp Asn Val Glu Gly Thr Arg Trp Ala
35 40 45

Val Leu Val Ala Gly Ser Lys Gly Tyr Val Asn Tyr Arg His Gln Ala
50 55 60

Asp Val Cys His Ala Tyr Gln Ile Leu Lys Lys Gly Gly Leu Lys Asp
65 70 75 80

Glu Asn Ile Ile Val Phe Met Tyr Asp Asp Ile Ala Tyr Asn Glu Ser
85 90 95

Asn Pro His Pro Gly Val Ile Ile Asn His Pro Tyr Gly Ser Asp Val
100 105 110

Tyr Lys Gly Val Pro Lys Asp Tyr Val Gly Glu Asp Ile Asn Pro Pro
115 120 125

Asn Phe Tyr Ala Val Leu Leu Ala Asn Lys Ser Ala Leu Thr Gly Thr
130 135 140

Gly Ser Gly Lys Val Leu Asp Ser Gly Pro Asn Asp His Val Phe Ile
145 150 155 160

Tyr Tyr Thr Asp His Gly Gly Ala Gly Val Leu Gly Met Pro Ser Lys
165 170 175

Pro Tyr Ile Ala Ala Ser Asp Leu Asn Asp Val Leu Lys Lys Lys His
180 185 190

Ala Ser Gly Thr Tyr Lys Ser Ile Val Phe Tyr Val Glu Ser Cys Glu
195 200 205

Ser Gly Ser Met Phe Asp Gly Leu Leu Pro Glu Asp His Asn Ile Tyr
210 215 220

Val Met Gly Ala Ser Asp Thr Gly Glu Ser Ser Trp Val Thr Tyr Cys
225 230 235 240

Pro Leu Gln His Pro Ser Pro Pro Pro Glu Tyr Asp Val Cys Val Gly
245 250 255

Asp Leu Phe Ser Val Ala Trp Leu Glu Asp Cys Asp Val His Asn Leu
260 265 270

Gln Thr Glu Thr Phe Gln Gln Gln Tyr Glu Val Val Lys Asn Lys Thr
275 280 285

Ile Val Ala Leu Ile Glu Asp Gly Thr His Val Val Gln Tyr Gly Asp
    290                 295                 300

Val Gly Leu Ser Lys Gln Thr Leu Phe Val Tyr Met Gly Thr Asp Pro
305                 310                 315                 320

Ala Asn Asp Asn Asn Thr Phe Thr Asp Lys Asn Ser Leu Gly Thr Pro
                325                 330                 335

Arg Lys Ala Val Ser Gln Arg Asp Ala Asp Leu Ile His Tyr Trp Glu
            340                 345                 350

Lys Tyr Arg Arg Ala Pro Glu Gly Ser Ser Arg Lys Ala Glu Ala Lys
        355                 360                 365

Lys Gln Leu Arg Glu Val Met Ala His Arg Met His Ile Asp Asn Ser
    370                 375                 380

Val Lys His Ile Gly Lys Leu Leu Phe Gly Ile Glu Lys Gly His Lys
385                 390                 395                 400

Met Leu Asn Asn Val Arg Pro Ala Gly Leu Pro Val Val Asp Asp Trp
                405                 410                 415

Asp Cys Phe Lys Thr Leu Ile Arg Thr Phe Glu Thr His Cys Gly Ser
            420                 425                 430

Leu Ser Glu Tyr Gly Met Lys His Met Arg Ser Phe Ala Asn Leu Cys
        435                 440                 445

Asn Ala Gly Ile Arg Lys Glu Gln Met Ala Glu Ala Ser Ala Gln Ala
    450                 455                 460

Cys Val Ser Ile Pro Asp Asn Pro Trp Ser Ser Leu His Ala Gly Phe
465                 470                 475                 480

Ser Val

<210> SEQ ID NO 5
<211> LENGTH: 10
<212> TYPE: PRT
<213> ORGANISM: Artificial
<220> FEATURE:
<223> OTHER INFORMATION: APP-IP

<400> SEQUENCE: 5

Ile Ser Tyr Gly Asn Asp Ala Leu Met Pro
1               5                   10

<210> SEQ ID NO 6
<211> LENGTH: 20
<212> TYPE: PRT
<213> ORGANISM: Artificial
<220> FEATURE:
<223> OTHER INFORMATION: RTD1-derived peptide

<400> SEQUENCE: 6

Cys Leu Cys Arg Arg Gly Val Cys Arg Cys Ile Cys Thr Ile Ser Tyr
1               5                   10                  15

Cys Asp Ala Leu
            20

<210> SEQ ID NO 7
<211> LENGTH: 36
<212> TYPE: PRT
<213> ORGANISM: Artificial
<220> FEATURE:
<223> OTHER INFORMATION: MCoTI-II DIV peptide

<400> SEQUENCE: 7

Gly Gly Val Cys Pro Lys Ile Leu Lys Lys Cys Arg Arg Asp Ser Asp

-continued 1               5                   10                  15

Cys Pro Gly Ala Cys Ile Cys Arg Gly Asn Gly Tyr Cys Gly Ser Gly
            20                  25                  30

Ser Asp Ile Val
        35

<210> SEQ ID NO 8
<211> LENGTH: 31
<212> TYPE: PRT
<213> ORGANISM: Artificial
<220> FEATURE:
<223> OTHER INFORMATION: kB2-DIV peptide

<400> SEQUENCE: 8

Gly Leu Pro Val Cys Gly Glu Thr Cys Phe Gly Gly Thr Cys Asn Thr
1               5                   10                  15

Pro Gly Cys Ser Cys Thr Trp Pro Ile Cys Thr Arg Asp Ile Val
            20                  25                  30

<210> SEQ ID NO 9
<211> LENGTH: 16
<212> TYPE: PRT
<213> ORGANISM: Artificial
<220> FEATURE:
<223> OTHER INFORMATION: STFI-DIV peptide

<400> SEQUENCE: 9

Gly Arg Cys Thr Lys Ser Ile Pro Pro Ile Cys Phe Pro Asp Ile Val
1               5                   10                  15

<210> SEQ ID NO 10
<211> LENGTH: 8
<212> TYPE: PRT
<213> ORGANISM: Artificial
<220> FEATURE:
<223> OTHER INFORMATION: RGD-DIV peptide

<400> SEQUENCE: 10

Phe Leu Ala Arg Gly Asp His Val
1               5

<210> SEQ ID NO 11
<211> LENGTH: 20
<212> TYPE: PRT
<213> ORGANISM: Artificial
<220> FEATURE:
<223> OTHER INFORMATION: RGD-defensin-DSL

<400> SEQUENCE: 11

Ala Cys Arg Cys Leu Cys Arg Arg Gly Asp Cys Arg Cys Ile Cys Arg
1               5                   10                  15

Gly Asp Ser Leu
            20

<210> SEQ ID NO 12
<211> LENGTH: 20
<212> TYPE: PRT
<213> ORGANISM: Artificial
<220> FEATURE:
<223> OTHER INFORMATION: RTD1-derived peptide
<220> FEATURE:
<221> NAME/KEY: MISC_FEATURE
<222> LOCATION: (18)..(18)
<223> OTHER INFORMATION: N-hydroxy-L-asparagine

<400> SEQUENCE: 12

-continued

```
Cys Leu Cys Arg Arg Gly Val Cys Arg Cys Ile Cys Thr Ile Ser Tyr
1               5                   10                  15

Cys Xaa Ala Leu
            20


<210> SEQ ID NO 13
<211> LENGTH: 16
<212> TYPE: PRT
<213> ORGANISM: Artificial
<220> FEATURE:
<223> OTHER INFORMATION: pB1 peptide

<400> SEQUENCE: 13

Lys Leu Gly Thr Ser Pro Gly Arg Leu Arg Tyr Ala Gly Asn Gly Leu
1               5                   10                  15


<210> SEQ ID NO 14
<211> LENGTH: 8
<212> TYPE: PRT
<213> ORGANISM: Artificial
<220> FEATURE:
<223> OTHER INFORMATION: RGD-N(OH)HV peptide
<220> FEATURE:
<221> NAME/KEY: MISC_FEATURE
<223> OTHER INFORMATION: N-hydroxyl-L-asparagine
<220> FEATURE:
<221> NAME/KEY: misc_feature
<222> LOCATION: (6)..(6)
<223> OTHER INFORMATION: Xaa can be any naturally occurring amino acid

<400> SEQUENCE: 14

Phe Leu Ala Arg Gly Xaa His Val
1               5


<210> SEQ ID NO 15
<211> LENGTH: 6
<212> TYPE: PRT
<213> ORGANISM: Artificial
<220> FEATURE:
<223> OTHER INFORMATION: RGD-N(OH) peptide
<220> FEATURE:
<221> NAME/KEY: MISC_FEATURE
<222> LOCATION: (6)..(6)
<223> OTHER INFORMATION: Xaa = N-hydroxyl-L-asparagine

<400> SEQUENCE: 15

Phe Leu Ala Arg Gly Xaa
1               5


<210> SEQ ID NO 16
<211> LENGTH: 12
<212> TYPE: PRT
<213> ORGANISM: Artificial
<220> FEATURE:
<223> OTHER INFORMATION: cyclized RGD-peptide dimer
<220> FEATURE:
<221> NAME/KEY: MISC_FEATURE
<222> LOCATION: (6)..(6)
<223> OTHER INFORMATION: xaa = N-hydroxyl-L-asparagine
<220> FEATURE:
<221> NAME/KEY: MISC_FEATURE
<222> LOCATION: (12)..(12)
<223> OTHER INFORMATION: xaa = N-hydroxyl-L-asparagine

<400> SEQUENCE: 16

Phe Leu Ala Arg Gly Xaa Phe Leu Ala Arg Gly Xaa
1               5                   10
```

<210> SEQ ID NO 17
<211> LENGTH: 14
<212> TYPE: PRT
<213> ORGANISM: Artificial
<220> FEATURE:
<223> OTHER INFORMATION: peptide

<400> SEQUENCE: 17

Ala Ile Tyr Arg Arg Gly Arg Leu Tyr Arg Arg Asn His Val
1 5 10

<210> SEQ ID NO 18
<211> LENGTH: 14
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (12)..(12)
<223> OTHER INFORMATION: Xaa = N-hydroxy-L-asparagine

<400> SEQUENCE: 18

Ala Ile Tyr Arg Arg Gly Arg Leu Tyr Arg Arg Xaa His Val
1 5 10

<210> SEQ ID NO 19
<211> LENGTH: 14
<212> TYPE: PRT
<213> ORGANISM: Artificial
<220> FEATURE:
<223> OTHER INFORMATION: peptide

<400> SEQUENCE: 19

Ala Ile Tyr Arg Arg Gly Arg Leu Tyr Arg Arg Asp His Val
1 5 10

<210> SEQ ID NO 20
<211> LENGTH: 14
<212> TYPE: PRT
<213> ORGANISM: Artificial
<220> FEATURE:
<223> OTHER INFORMATION: peptide

<400> SEQUENCE: 20

Ala Ile Tyr Arg Arg Gly Arg Leu Tyr Arg Arg Asn Ser Leu
1 5 10

<210> SEQ ID NO 21
<211> LENGTH: 14
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (12)..(12)
<223> OTHER INFORMATION: Xaa = N-hydroxy-L-asparagine

<400> SEQUENCE: 21

Ala Ile Tyr Arg Arg Gly Arg Leu Tyr Arg Arg Xaa Ser Leu
1 5 10

<210> SEQ ID NO 22
<211> LENGTH: 14
<212> TYPE: PRT
<213> ORGANISM: Artificial
<220> FEATURE:
<223> OTHER INFORMATION: peptide -continued

<400> SEQUENCE: 22

Ala Ile Tyr Arg Arg Gly Arg Leu Tyr Arg Arg Asp Ser Leu
1               5                   10

<210> SEQ ID NO 23
<211> LENGTH: 10
<212> TYPE: PRT
<213> ORGANISM: Artificial
<220> FEATURE:
<223> OTHER INFORMATION: (cyclized) APP-IP peptide
<220> FEATURE:
<221> NAME/KEY: MISC_FEATURE
<222> LOCATION: (6)..(6)
<223> OTHER INFORMATION: Xaa = N-hydroxy-L-asparagine

<400> SEQUENCE: 23

Ile Ser Tyr Gly Asn Xaa Ala Leu Met Pro
1               5                   10

<210> SEQ ID NO 24
<211> LENGTH: 10
<212> TYPE: PRT
<213> ORGANISM: Artificial
<220> FEATURE:
<223> OTHER INFORMATION: cyclized APP-IP peptide
<220> FEATURE:
<221> NAME/KEY: MISC_FEATURE
<222> LOCATION: (6)..(6)
<223> OTHER INFORMATION: Xaa = N-hydroxy-L-asparagine

<400> SEQUENCE: 24

Ile Ser Tyr Gly Gln Xaa Ala Leu Met Pro
1               5                   10

<210> SEQ ID NO 25
<211> LENGTH: 12
<212> TYPE: PRT
<213> ORGANISM: Artificial
<220> FEATURE:
<223> OTHER INFORMATION: (cyclized) APP-IP peptide
<220> FEATURE:
<221> NAME/KEY: MISC_FEATURE
<222> LOCATION: (7)..(7)
<223> OTHER INFORMATION: Xaa = N-hydroxy-L-asparagine

<400> SEQUENCE: 25

Ser Ile Ser Tyr Gly Gln Xaa Ala Leu Met Pro Gly
1               5                   10

<210> SEQ ID NO 26
<211> LENGTH: 14
<212> TYPE: PRT
<213> ORGANISM: Artificial
<220> FEATURE:
<223> OTHER INFORMATION: cyclized APP-IP peptide
<220> FEATURE:
<221> NAME/KEY: MISC_FEATURE
<222> LOCATION: (8)..(8)
<223> OTHER INFORMATION: Xaa = N-hydroxy-L-asparagine

<400> SEQUENCE: 26

Ser Gly Ile Ser Tyr Gly Gln Xaa Ala Leu Met Pro Ser Gly
1               5                   10

<210> SEQ ID NO 27
<211> LENGTH: 16
<212> TYPE: PRT
<213> ORGANISM: Artificial

<220> FEATURE:
<223> OTHER INFORMATION: cyclized APP-IP peptide
<220> FEATURE:
<221> NAME/KEY: MISC_FEATURE
<222> LOCATION: (9)..(9)
<223> OTHER INFORMATION: Xaa = N-hydroxy-L-asparagine

<400> SEQUENCE: 27

Gly Ser Gly Ile Ser Tyr Gly Gln Xaa Ala Leu Met Pro Ser Gly Ala
1 5 10 15

<210> SEQ ID NO 28
<211> LENGTH: 18
<212> TYPE: PRT
<213> ORGANISM: Artificial
<220> FEATURE:
<223> OTHER INFORMATION: cyclized APP-IP peptide
<220> FEATURE:
<221> NAME/KEY: MISC_FEATURE
<222> LOCATION: (10)..(10)
<223> OTHER INFORMATION: Xaa = N-hydroxy-L-asparagine

<400> SEQUENCE: 28

Ala Thr Ser Gly Ile Ser Tyr Gly Gln Xaa Ala Leu Met Pro Ser Gly
1 5 10 15

Tyr Met

<210> SEQ ID NO 29
<211> LENGTH: 20
<212> TYPE: PRT
<213> ORGANISM: Artificial
<220> FEATURE:
<223> OTHER INFORMATION: cyclized APP-IP peptide
<220> FEATURE:
<221> NAME/KEY: MISC_FEATURE
<222> LOCATION: (11)..(11)
<223> OTHER INFORMATION: Xaa = N-hydroxy-L-asparagine

<400> SEQUENCE: 29

Ala Thr Arg Ser Gly Ile Ser Tyr Gly Gln Xaa Ala Leu Met Pro Ser
1 5 10 15

Gly Gln Tyr Met
20

<210> SEQ ID NO 30
<211> LENGTH: 18
<212> TYPE: PRT
<213> ORGANISM: Artificial
<220> FEATURE:
<223> OTHER INFORMATION: cyclic RTD1-derived peptide

<400> SEQUENCE: 30

Gly Phe Cys Arg Cys Leu Cys Arg Arg Gly Val Cys Arg Cys Ile Cys
1 5 10 15

Thr Arg

<210> SEQ ID NO 31
<211> LENGTH: 18
<212> TYPE: PRT
<213> ORGANISM: Artificial
<220> FEATURE:
<223> OTHER INFORMATION: cyclic RTD1-derived peptide
<220> FEATURE:
<221> NAME/KEY: MISC_FEATURE
<222> LOCATION: (4)..(4)
<223> OTHER INFORMATION: Xaa = N-hydroxy-L-asparagine

<400> SEQUENCE: 31

```
Ser Tyr Cys Xaa Cys Leu Cys Arg Arg Gly Val Cys Arg Cys Ile Cys
1               5                   10                  15

Thr Ile


<210> SEQ ID NO 32
<211> LENGTH: 18
<212> TYPE: PRT
<213> ORGANISM: Artificial
<220> FEATURE:
<223> OTHER INFORMATION: cyclic RTD1-derived peptide

<400> SEQUENCE: 32

Ser Tyr Cys Asp Cys Leu Cys Arg Arg Gly Val Cys Arg Cys Ile Cys
1               5                   10                  15

Thr Ile


<210> SEQ ID NO 33
<211> LENGTH: 18
<212> TYPE: PRT
<213> ORGANISM: Artificial
<220> FEATURE:
<223> OTHER INFORMATION: cyclic RTD1-derived peptide

<400> SEQUENCE: 33

Ser Tyr Cys Asn Cys Leu Cys Arg Arg Gly Val Cys Arg Cys Ile Cys
1               5                   10                  15

Thr Ile


<210> SEQ ID NO 34
<211> LENGTH: 36
<212> TYPE: PRT
<213> ORGANISM: Artificial
<220> FEATURE:
<223> OTHER INFORMATION: MCo-I-II-N(OH)IV
<220> FEATURE:
<221> NAME/KEY: MISC_FEATURE
<222> LOCATION: (34)..(34)
<223> OTHER INFORMATION: Xaa = N-hydroxy-L-asparagine

<400> SEQUENCE: 34

Gly Gly Val Cys Pro Lys Ile Leu Lys Lys Cys Arg Arg Asp Ser Asp
1               5                   10                  15

Cys Pro Gly Ala Cys Ile Cys Arg Gly Asn Gly Tyr Cys Gly Ser Gly
            20                  25                  30

Ser Xaa Ile Val
        35


<210> SEQ ID NO 35
<211> LENGTH: 31
<212> TYPE: PRT
<213> ORGANISM: Artificial
<220> FEATURE:
<223> OTHER INFORMATION: kB2-N(OH)IV
<220> FEATURE:
<221> NAME/KEY: MISC_FEATURE
<222> LOCATION: (29)..(29)
<223> OTHER INFORMATION: Xaa = N-hydroxy-L-asparagine

<400> SEQUENCE: 35

Gly Leu Pro Val Cys Gly Glu Thr Cys Phe Gly Gly Thr Cys Asn Thr
1               5                   10                  15

Pro Gly Cys Ser Cys Thr Trp Pro Ile Cys Thr Arg Xaa Ile Val
            20                  25                  30
```

<210> SEQ ID NO 36
<211> LENGTH: 16
<212> TYPE: PRT
<213> ORGANISM: Artificial
<220> FEATURE:
<223> OTHER INFORMATION: SFTI-N(OH)IV
<220> FEATURE:
<221> NAME/KEY: MISC_FEATURE
<222> LOCATION: (14)..(14)
<223> OTHER INFORMATION: Xaa = N-hydroxy-L-asparagine

<400> SEQUENCE: 36

```
Gly Arg Cys Thr Lys Ser Ile Pro Pro Ile Cys Phe Pro Xaa Ile Val
1               5                   10                  15
```

<210> SEQ ID NO 37
<211> LENGTH: 20
<212> TYPE: PRT
<213> ORGANISM: Artificial
<220> FEATURE:
<223> OTHER INFORMATION: RGD-defensin-N(OH)SL
<220> FEATURE:
<221> NAME/KEY: MISC_FEATURE
<222> LOCATION: (18)..(18)
<223> OTHER INFORMATION: Xaa = N-hydroxy-L-asparagine

<400> SEQUENCE: 37

```
Ala Cys Arg Cys Leu Cys Arg Arg Gly Asp Cys Arg Cys Ile Cys Arg
1               5                   10                  15

Gly Xaa Ser Leu
            20
```

<210> SEQ ID NO 38
<211> LENGTH: 14
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (12)..(12)
<223> OTHER INFORMATION: Xaa = N-methyl-L-asparagine

<400> SEQUENCE: 38

```
Ala Ile Tyr Arg Arg Gly Arg Leu Tyr Arg Arg Xaa His Val
1               5                   10
```

<210> SEQ ID NO 39
<211> LENGTH: 34
<212> TYPE: PRT
<213> ORGANISM: Artificial
<220> FEATURE:
<223> OTHER INFORMATION: MCoTI-II

<400> SEQUENCE: 39

```
Gly Gly Val Cys Pro Lys Ile Leu Lys Lys Cys Arg Arg Asp Ser Asp
1               5                   10                  15

Cys Pro Gly Ala Cys Ile Cys Arg Gly Asn Gly Tyr Cys Gly Ser Gly
            20                  25                  30

Ser Asp
```

<210> SEQ ID NO 40
<211> LENGTH: 14
<212> TYPE: PRT
<213> ORGANISM: Artificial
<220> FEATURE:
<223> OTHER INFORMATION: SFTI

<400> SEQUENCE: 40

Gly Arg Cys Thr Lys Ser Ile Pro Pro Ile Cys Phe Pro Asp
1 5 10

<210> SEQ ID NO 41
<211> LENGTH: 9
<212> TYPE: PRT
<213> ORGANISM: Artificial
<220> FEATURE:
<223> OTHER INFORMATION: peptide

<400> SEQUENCE: 41

Ser Tyr Gly Asn Asp Ala Leu Met Pro
1 5

<210> SEQ ID NO 42
<211> LENGTH: 8
<212> TYPE: PRT
<213> ORGANISM: Artificial
<220> FEATURE:
<223> OTHER INFORMATION: peptide

<400> SEQUENCE: 42

Tyr Gly Asn Asp Ala Leu Met Pro
1 5

<210> SEQ ID NO 43
<211> LENGTH: 6
<212> TYPE: PRT
<213> ORGANISM: Artificial
<220> FEATURE:
<223> OTHER INFORMATION: Ligation motif peptide
<220> FEATURE:
<221> NAME/KEY: MISC_FEATURE
<222> LOCATION: (4)..(4)
<223> OTHER INFORMATION: N is N-gamma-amino-L-asparagine

<400> SEQUENCE: 43

Lys Tyr Ser Asn Gly Leu
1 5

<210> SEQ ID NO 44
<211> LENGTH: 5
<212> TYPE: PRT
<213> ORGANISM: Artificial
<220> FEATURE:
<223> OTHER INFORMATION: Ligation acceptor substrate

<400> SEQUENCE: 44

Gly Ile Arg Gly Ile
1 5

<210> SEQ ID NO 45
<211> LENGTH: 299
<212> TYPE: PRT
<213> ORGANISM: Artificial
<220> FEATURE:
<223> OTHER INFORMATION: OaAEPb1 active domain

<400> SEQUENCE: 45

Ser Val Gly Thr Arg Trp Ala Val Leu Ile Ala Gly Ser Lys Gly Tyr
1 5 10 15

Ala Asn Tyr Arg His Gln Ala Gly Val Cys His Ala Tyr Gln Ile Leu
20 25 30

Lys Arg Gly Gly Leu Lys Asp Glu Asn Ile Val Val Phe Met Tyr Asp

-continued

```
        35                  40                  45

Asp Ile Ala Tyr Asn Glu Ser Asn Pro Arg Pro Gly Val Ile Ile Asn
    50                  55                  60

Ser Pro His Gly Ser Asp Val Tyr Ala Gly Val Pro Lys Asp Tyr Thr
65                  70                  75                  80

Gly Glu Glu Val Asn Ala Lys Asn Phe Leu Ala Ala Ile Leu Gly Asn
                85                  90                  95

Lys Ser Ala Ile Thr Gly Gly Ser Gly Lys Val Val Asp Ser Gly Pro
            100                 105                 110

Asn Asp His Ile Phe Ile Tyr Tyr Thr Asp His Gly Ala Ala Gly Val
        115                 120                 125

Ile Gly Met Pro Ser Lys Pro Tyr Leu Tyr Ala Asp Glu Leu Asn Asp
    130                 135                 140

Ala Leu Lys Lys Lys His Ala Ser Gly Thr Tyr Lys Ser Leu Val Phe
145                 150                 155                 160

Tyr Leu Glu Ala Cys Glu Ser Gly Ser Met Phe Glu Gly Ile Leu Pro
                165                 170                 175

Glu Asp Leu Asn Ile Tyr Ala Leu Thr Ser Thr Asn Thr Thr Glu Ser
            180                 185                 190

Ser Trp Ala Tyr Tyr Cys Pro Ala Gln Glu Asn Pro Pro Pro Pro Glu
        195                 200                 205

Tyr Asn Val Cys Leu Gly Asp Leu Phe Ser Val Ala Trp Leu Glu Asp
    210                 215                 220

Ser Asp Val Gln Asn Ser Trp Tyr Glu Thr Leu Asn Gln Gln Tyr His
225                 230                 235                 240

His Val Asp Lys Arg Ile Ser His Ala Ser His Ala Thr Gln Tyr Gly
                245                 250                 255

Asn Leu Lys Leu Gly Glu Glu Gly Leu Phe Val Tyr Met Gly Ser Asn
            260                 265                 270

Pro Ala Asn Asp Asn Tyr Thr Ser Leu Asp Gly Asn Ala Leu Thr Pro
        275                 280                 285

Ser Ser Ile Val Val Asn Gln Arg Asp Ala Asp
    290                 295
```

METHODS FOR CYCLIZATION OF (POLY)PEPTIDES COMPRISING $N^{\gamma}$-HYDROXY- OR $N^{\gamma}$-AMINO-L-ASPARAGINE

STATEMENT REGARDING SEQUENCE LISTING

The Sequence Listing associated with this application is provided in text format in lieu of a paper copy, and is hereby incorporated by reference into the specification. The name of the text file containing the Sequence Listing is 613USPC_SeqListing.txt. The text file is 27.2 KB, was created on Sep. 1, 2023, and is being submitted electronically.

CROSS-REFERENCE TO RELATED APPLICATIONS

This application claims the benefit of priority of Singapore Patent Application No. 10202102295S filed Mar. 5, 2021, the content of which being hereby incorporated by reference in its entirety for all purposes.

FIELD OF THE INVENTION

The present invention lies in the technical field of enzymatic (poly)peptide cyclization and specifically relates to methods that employ enzymes having Asn-specific cyclase activity as a means for generating cyclic (poly)peptides from (poly)peptides that comprise a ligation motif comprising a $N^{\gamma}$-hydroxy-L-asparagine or $N^{\gamma}$-amino-L-asparagine residue. Further encompassed are the resulting cyclic (poly) peptides and the corresponding uses.

BACKGROUND OF THE INVENTION

Macrocyclization is an effective way to restrict the conformations of linear peptides, which can increase their metabolic stability and pharmacological activity (Vinogradov et al. *ChemMedChem,* 2013, 8, 377-384). The large surface areas of cyclic peptides confer high binding affinity and selectivity to inhibit protein-protein interactions, which are typically 'undruggable' with small-molecule compounds (Lau & Dunn, *Bioorg. Med. Chem.,* 2018, 26, 2700-2707; Fosgerau & Hoffmann, *Drug Discovery Today,* 2015, 20, 122-128). Recently, it has been shown that asparaginyl endopeptidases (AEPs) are the biocatalysts for the macrocyclization of cyclotides in plants (Saska et al. *J. Biol. Chem.,* 2007, 282, 29721-29728; S. Harris et al. *Nat. Commun.,* 2015, 6, 10199; Nguyen et al. *Nat. Chem. Biol.,* 2014, 10, 732-738). AEPs are cysteine endopeptidases that typically recognize and hydrolyze peptide bonds after an Asn or Asp residue (Abe et al. *J. Biol. Chem.,* 1993, 268, 3525-3529; Wang & Hugh, *Nat. Struct. Mol. Biol.,* 1994, 1, 502-504). Interestingly, some members of the AEP family catalyze formation of new asparaginyl peptide bonds through transpeptidation and as such qualify as peptidyl asparaginyl ligases (PALs) (Nguyen et al. *Nat. Chem. Biol.,* 2014, 10, 732-738; Harris et al. *Sci. Rep.,* 2019, 9, 10820; Hemu et al. *Proc. Natl. Acad. Sci.,* 2019, 116, 11737-1174; Hemu et al. *ACS Catal.* 2020, 10, 8825-8834; Tam et al. *Sci. China Chem.* 2020, 3, 296-307). Although PALs are classified as Asx-specific enzymes, most of them have a strong preference for P1-Asn substrates to the P1-Asp substrates, with a typical 100-to-800-fold difference in the rate of cyclization reactions for the two types of substrates (Nguyen et al., supra; Bernath-Levn et al. *Chemistry & Biology,* 2015, 22, 571-582). Therefore, almost all applications of PAL-mediated ligation/cyclization reported to date were limited for P1-Asn substrates (Harris et al. *Sci. Rep.,* 2019, 9, 10820; Hemu et al. *J. Am. Chem. Soc.,* 2016, 138, 6968-6971; Rehm et al. *J. Am. Chem. Soc.,* 2019, 141, 17388-17393; Nguyen et al. *Angew. Chem. Int. Ed.,* 2016, 55, 12802; Cao et al. *Chem. Commun.,* 2015, 51, 17289-17292; Bi et al. *Angew. Chem. Int. Ed.,* 2017, 56, 7822-7825). The applications of PALs, such as butelase1 and VyPAL2 and OaAEPb1, can be largely expanded if their substrate scope can be broadened.

AEPs cleave aspartyl peptide bonds at acidic pH, and perform transpeptidation at near neutral pH. It has been shown from structural characterization of AEP-aspartyl peptide inhibitor complexes that the sidechain carboxyl gamma-COOH of P1-Asp acts as a hydrogen bond donor to form a hydrogen bond with a key residue in the S1 pocket of the enzyme (Zauner et al. *J. Biol. Chem.,* 2018, 293, 8934-8946; James et al. *PlantJ,* 2019, 98, 988-999). Given the low pKa of the carboxylic acid group, a low pH—optimally pH 4-5—is required to maintain it in the protonated form for enzyme binding. However, at this pH, the amine nucleophile of any incoming peptide is mostly protonated, making it less available to attack the acyl-enzyme thioester intermediate in a ligation reaction. This dilemma is the main reason that PAL-catalyzed ligation is much slower at aspartyl than at asparaginyl bonds.

Thus, there exists a need in the art for strategies that allow cyclization of (poly)peptides via Asp residues by using the enzymatic activity of PALs.

SUMMARY OF THE INVENTION

The inventors surprisingly found that $N^{\gamma}$-hydroxy-L-asparagine (also referred to as "Asn(OH)" or "N(OH)" herein; synonyms: beta-L-aspartylhydroxamic acid; L-aspartic acid beta-hydroxyamate), which was designed as a mimetic of Asn and has its side-chain amide modified by an N-hydroxyl group, has the ability to form via its the sidechain gamma-CO—NH(OH) similar interactions with the enzyme's S1 pocket as Asn. Especially, the higher pKa value of the N—OH group helps to maintain it as a hydrogen bond donor at neutral to weakly basic pH. It could be shown that P1-Asn(OH) peptides are well recognized by PALs, such as butelase-1 and VyPAL2, in the cyclization reaction (Table 1 and FIG. 5, 6). This unnatural Asn(OH) residue can later function as a chelator for metal ions to inhibit metalloenzymes or can be converted to Asp in a mild oxidation reaction (FIG. 1). A similar behavior has been observed for $N^{\gamma}$-amino-L-asparagine (also referred to as N-gamma-amino-L-asparagine, "Asn($NH_2$)" or "N($NH_2$)" herein), wherein the side chain amide group has been modified by an N-amino group. Said residue may also be oxidized to yield D.

In a first aspect, the invention relates to methods for the cyclization of a (poly)peptide comprising an $N^{\gamma}$-hydroxy-L-asparagine (Asn(OH)) or $N^{\gamma}$-amino-L-asparagine (Asn ($NH_2$)) residue, the method comprising the steps of:

(i) providing a linear (poly)peptide comprising an $N^{\gamma}$-hydroxy-L-asparagine or $N^{\gamma}$-amino-L-asparagine residue;

(ii) contacting the linear (poly)peptide comprising an $N^{\gamma}$-hydroxy-L-asparagine or $N^{\gamma}$-amino-L-asparagine residue with a peptidyl asparaginyl ligase (PAL) under conditions that allow cleavage of the amino acids C-terminal to the $N^{\gamma}$-hydroxy-L-asparagine or $N^{\gamma}$-amino-L-asparagine residue and ligation of the C-terminus of the $N^{\gamma}$-hydroxy-L-asparagine or $N^{\gamma}$-amino-L-asparagine residue to the N-terminus of the (poly)peptide to cyclize the (poly)peptide.

In various embodiments, the linear (poly)peptide comprising an $N^{\gamma}$-hydroxy-L-asparagine or $N^{\gamma}$-amino-L-asparagine residue comprises or consists of the amino acid sequence $(X)_o N(OH)(X)_p$, with X being any amino acid, o being an integer of 1 or more, preferably 2 or more, p being an integer of 1 or more, preferably of 2 or more, more preferably 2, and N(OH) being $N^{\gamma}$-hydroxy-L-asparagine. In such embodiments, $(X)_p$ may be $X^3X^4(X)_r$, with $X^3$ being any amino acid with the exception of P, preferably A, C, F, G, H, K, N, Q, R, S, Y, I, preferably H, G, S, N, Q and R, more preferably H, G or S, $X^4$ being a hydrophobic or aromatic amino acid, preferably selected from L, I, V, F, C, W, Y and M, preferably V, L, I and F, and r being 0 or an integer of 1 or more, preferably 0. Accordingly, in various embodiments, the (poly)peptide comprises the amino acid sequence N(OH)HV or N(OH)GL or N(OH)SL or N(OH)AL or N(OH)IV, preferably on its C-terminus, wherein N(OH) represents the $N^{\gamma}$-hydroxy-L-asparagine residue. In these embodiments N(OH) may be replaced by $N(NH_2)$ representing the $N^{\gamma}$-amino-L-asparagine.

In various embodiments, the (poly)peptide comprises the N-terminal amino acid sequence $X^1X^2$, wherein $X^1$ is G or H and $X^2$ being G, F, L, V or I.

While in principle all PALs with cyclization activity are suitable for the methods described herein, in various embodiments the PAL is selected from butelase-1 and VyPAL2 and OaAEPb1 or variants thereof, as these have been found to have the highest cyclization activity. VyPAL2 may comprise or consist of the amino acid sequence set forth in SEQ ID NO:1 or may be a variant thereof that has an amino acid sequence that has at least 80% sequence identity to the amino acid sequence set forth in SEQ ID NO:1 over its entire length. Butelase-1 may comprise or consist of the amino acid sequence set forth in SEQ ID NO:2 or may be a variant thereof that has an amino acid sequence that has at least 80% sequence identity to the amino acid sequence set forth in SEQ ID NO:2 over its entire length. OaAEP1b may comprise or consist of the amino acid sequence set forth in SEQ ID NO:45 or may be a variant thereof that has an amino acid sequence that has at least 80% sequence identity to the amino acid sequence set forth in SEQ ID NO:45 over its entire length. The asparaginyl ligase consisting of SEQ ID NO:1 is also referred to herein as "VyPAL2" or "VyPAL2 active form/domain". The asparaginyl ligase consisting of SEQ ID NO:2 is also referred to herein as "butelase-1" or "butelase-1 active form/domain". The asparaginyl ligase consisting of SEQ ID NO:45 is also referred to herein as "OaAEPb1" or "OaAEPb1 active form". The full-length polypeptide sequence of VyPAL2 is set forth in SEQ ID NO:3. The full-length polypeptide sequence of butelase-1 is set forth in SEQ ID NO:4.

In various embodiments where the PAL is VyPAL2 or a variant thereof, the (poly)peptide comprises the amino acid sequence $(X)_o N(OH)X^3X^4(X)_p$ or $(X)_o N(NH_2)X^3X^4(X)_p$, wherein X is any amino acid and o is an integer of at least 2, $X^3$ is G or S, and $X^4$ is a hydrophobic or aromatic amino acid, preferably selected from L, I, V, F, C, W, Y and M, preferably L or F, and p is 0 or an integer of 1 or more and N(OH) is $N^{\gamma}$-hydroxy-L-asparagine and $N(NH_2)$ is Nγ-amino-L-asparagine. In alternative embodiments where the PAL is butelase-1 or a variant thereof, the (poly)peptide comprises the amino acid sequence $(X)_o N(OH)X^3X^4(X)_p$ or $(X)_o N(NH_2)X^3X^4(X)_p$, wherein X is any amino acid and o is an integer of at least 2, $X^3$ is H, and $X^4$ is a hydrophobic or aromatic amino acid, preferably selected from L, I, V, F, C, W, Y and M, preferably V, and p is 0 or an integer of 1 or more and N(OH) is $N^{\gamma}$-hydroxy-L-asparagine and $N(NH_2)$ is $N^{\gamma}$-amino-L-asparagine.

While the peptide to be cyclized can be any peptide or polypeptide, in various embodiments, it is a peptide hormone or therapeutic peptide. The (poly)peptides to be cyclized typically comprise only a single $N^{\gamma}$-hydroxy-L-asparagine or $N^{\gamma}$-amino-L-asparagine residue (that is located in the ligation motif). In various embodiments, the (poly)peptide to be cyclized does not comprise any one or more of the sequence motifs NHV, NGL, NSL, NAL, NIV, preferably does not comprise the amino acid motif $NX^3X^4$, with $X^3$ being any amino acid with the exception of P, preferably A, C, F, G, H, K, N, Q, R, S, Y, I, preferably H, G, S, N, Q and R, more preferably H, G or S, $X^4$ being a hydrophobic or aromatic amino acid, preferably selected from L, I, V, F, C, W, Y and M, preferably V, L, I and F, more preferably does not comprise any N residue. This may help to avoid that a side reaction with ligation at another N residue occurs. Accordingly, in various embodiments, it can be preferred that the (poly)peptide to be cyclized does not contain any ligation motif for the used PAL other than that comprising the N(OH) or $N(NH_2)$ residue.

In various embodiments, the method further comprises the step of converting the $N^{\gamma}$-hydroxy-L-asparagine or $N^{\gamma}$-amino-L-asparagine residue into L-aspartic acid/L-aspartate by oxidizing the cyclized (poly)peptide.

The invention further encompasses the cyclized (poly)peptides obtained according to the method of the invention, including the cyclic (poly)peptides comprising a $N^{\gamma}$-hydroxy-L-asparagine or $N^{\gamma}$-amino-L-asparagine residue.

DETAILED DESCRIPTION

Figure 1:
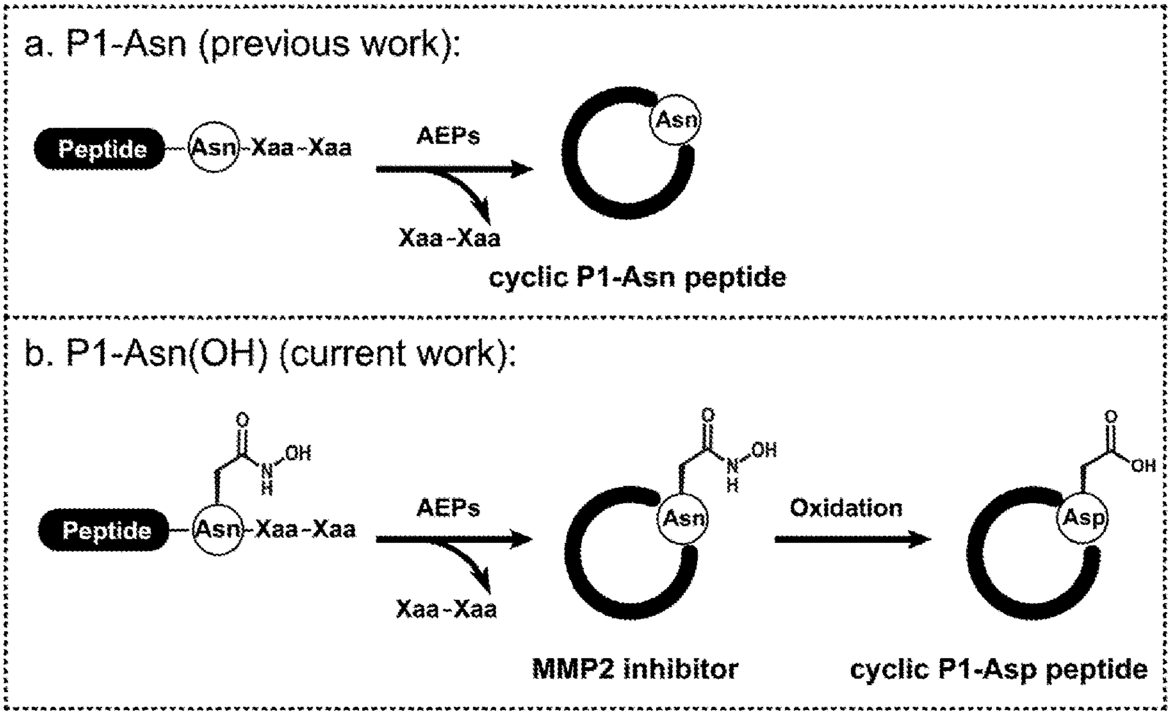
FIG. 1. Previous (a) and current (b) work on PAL-mediated cyclization. (a) cyclization of P1-Asn peptides. (2) cyclization of P1-Asn(OH) peptide substrates and oxidation of Asn(OH) to Asp.

The present invention is based on the inventors' finding that PALs can be efficiently used to convert D-containing (poly)peptides by replacing the D residue in the substrate (poly)peptide by the amino acid $N^{\gamma}$-hydroxy-L-asparagine or $N^{\gamma}$-amino-L-asparagine. Once cyclized this residue can readily be converted back into D. Additionally, it was found that certain of the thus generated cyclic peptides have beneficial activities and functionalities due to the presence of the $N^{\gamma}$-hydroxy-L-asparagine residue and may thus have use as therapeutic peptides.

The invention relates to methods for the cyclization of a (poly)peptide comprising an $N^{\gamma}$-hydroxy-L-asparagine (Asn(OH)) or $N^{\gamma}$-amino-L-asparagine (Asn($NH_2$)) residue using peptidyl asparaginyl ligases (PALs). $N^{\gamma}$-hydroxy-L-asparagine has the following formula and may be incorporated in a given (poly)peptide instead of aspartic acid or asparagine:

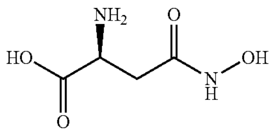

$N^{\gamma}$-amino-L-asparagine has the following formula and may be incorporated in a given (poly)peptide instead of aspartic acid or asparagine:

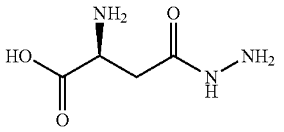

As explained above, it has been found that said residues which were designed as mimetics of Asn have the ability to form via its the sidechain gamma-CO—NH(OH) or gamma-CO—NH($NH_2$) similar interactions with the PAL enzymes as Asn and thus is well recognized by PALs, such as butelase-1 and VyPAL2 and OaAEPb1, in the cyclization reaction. As the N(OH) residue allows easy conversion to Asp, it provides for a means to effectively cyclize (poly) peptides that do not have a suitable N residue, but for which the cyclization efficiency on the D residue is undesirably low. It has also been found that unnatural Asn(OH) residue can function as a chelator for metal ions to inhibit metalloenzymes.

The methods of the invention include a first step of providing a (poly)peptide to be cyclized comprising an $N^{\gamma}$-hydroxy-L-asparagine residue (N(OH)) or $N^{\gamma}$-amino-L-asparagine residue (N($NH_2$)). The N(OH) or N($NH_2$) residue is typically part of a ligation motif that is recognized by the ligase, with all amino acids C-terminal to the N(OH) or N($NH_2$) residue being cleaved off during the ligation reaction. It is thus preferred that the N(OH) or N($NH_2$) residue is located close to the C-terminus in the (poly)peptide to be cyclized, since all amino acids C-terminal thereto will be cleaved off anyway. In the next step of the cyclization reaction, the intramolecular ligation, the C-terminus of the N(OH) or N($NH_2$) residue is linked to the N-terminus of the (poly)peptide, thus cyclizing the (poly)peptide.

The term "(poly)peptide", as used herein, refers to peptides and polypeptides. "Polypeptide", as used herein, relates to polymers made from amino acids connected by peptide bonds. The polypeptides, as defined herein, can comprise more than 50 amino acids, preferably 100 or more amino acids. "Peptides", as used herein, relates to polymers made from amino acids connected by peptide bonds. The peptides, as defined herein, can comprise 2 or more amino acids, preferably 10 or more amino acids, more preferably 15 or more amino acids, for example 15 to 50 amino acids. It is preferred that the peptides have a certain length, such as 10 amino acids, as otherwise cyclization is not possible or puts significant structural constraints on the cyclized molecules.

The N(OH) or N($NH_2$) residue may be artificially added to the (poly)peptide sequence, typically at is C-terminus, preferably in form of one of the ligation motifs disclosed herein, or may replace a D residue in the (poly)peptide to be cyclized. In the latter case, the (poly)peptide in its linear form is preferably artificially rearranged that the D residue replaced by the N(OH) or N($NH_2$) residue is locate on its C-terminus and all amino acids C-terminal thereto in the desired sequence are added to the N-terminus.

This ensures that the cyclized (poly)peptide then has the complete desired sequence even if the D residue replaced by N(OH) or N($NH_2$) is in the middle of the natural sequence. In any case, also in these embodiments, it may be preferred that C-terminal to the N(OH) or N($NH_2$) two additional, non-natural amino acids are added, as the ligation/cyclization efficiency of the PALs is highest if there are two amino acids C-terminal to the cleavage site. Suitable three amino acid long ligation motifs are disclosed herein below.

The (poly)peptides of the invention typically comprise only a single $N^{\gamma}$-hydroxy- or $N^{\gamma}$-amino-L-asparagine residue (that is located in the ligation motif). This avoids that parallel ligation reactions at alternative sites occur. In order to avoid cleavage and ligation at other sites within the (poly)peptide, it may be preferred that it does not contain any further ligation motifs for the PAL employed or these are located within the (poly)peptide structure such that they are not well accessible for the enzyme such that cyclization preferably occurs via the N(OH)- or N($NH_2$)-including ligation site. As the PALs prefer ligation sites at or close to the C-terminus, in certain instances it may be acceptable that the (poly)peptide comprises N residues/ligation motifs N-terminal to the actual desired N(OH)- or N($NH_2$)-comprising ligation site.

"Ligation motif", as used herein, relates to an amino acid sequence motif that is recognized and acted upon by the PAL employed. Typically, it is three amino acids in length and starts with the N or N(OH) or N($NH_2$) residue followed by two other amino acids. These two other amino acids can be, in principle, any amino acids, although they are preferably not P. Preferred amino acids at these positions are disclosed below. The ligation motifs for PALs are well known to those skilled in the art, for example from WO 2020/226572 A1. The motif that is ligated to the C-terminal residue, N or N(OH) or N($NH_2$), after cleavage of the C-terminus is also referred to as "ligation handle", and is rather variable. In various embodiments, it can be preferred that it starts with G at its N-terminus and the second amino acid is any one of these disclosed below. The different specificities of the PALs have also been reported for these ligation handle motifs and can be selected accordingly. However, it needs to be noted that substrate specificity of the PALs is not particularly high and that they can accommodate for a variety of different motifs and thus allow cyclization of a broad variety of peptides without the need for amino acid substitutions.

In various embodiments, the (poly)peptide to be cyclized does not comprise any one or more of the sequence motifs NHV, NGL, NSL, NAL, NIV, preferably does not comprise the amino acid motif $NX^3X^4$, with $X^3$ being any amino acid with the exception of P, preferably A, C, F, G, H, K, N, Q, R, S, Y, I, preferably H, G, S, N, Q and R, more preferably H, G or S, $X^4$ being a hydrophobic or aromatic amino acid, preferably selected from L, I, V, F, C, W, Y and M, preferably V, L, I and F. These are the ligation motifs that have been previously reported for the PALs. In some embodiments, the (poly)peptide does not comprise any N residue. This may help to avoid that a side reaction with ligation at another N residue occurs.

In various embodiments, the linear (poly)peptide comprising an $N^{\gamma}$-hydroxy- or $N^{\gamma}$-amino-L-asparagine residue comprises or consists of the amino acid sequence $(X)_oN(OH)(X)_p$, with X being any amino acid, o being an integer of 1 or more, preferably 2 or more, p being an integer of 1 or more, preferably of 2 or more, more preferably 2, and N(OH) being $N^{\gamma}$-hydroxy-L-asparagine. N(OH) is used as an example and may be replaced in all such embodiments by $N(NH_2)$. In such embodiments, $(X)_p$ may be $X^3X^4(X)_r$, with $X^3$ being any amino acid with the exception of P, preferably A, C, F, G, H, K, N, Q, R, S, Y, I, preferably H, G, S, N, Q and R, more preferably H, G or S, $X^4$ being a hydrophobic or aromatic amino acid, preferably selected from L, I, V, F, C, W, Y and M, preferably V, L, I and F, and r being 0 or an integer of 1 or more, preferably 0. Suitable ligation motifs include, without limitation, the amino acid sequences N(OH)HV or N(OH)GL or N(OH)SL or N(OH)AL or N(OH)IV. These may be located on the C-terminus of the (poly)peptide, wherein N(OH) represents the $N^{\gamma}$-hydroxy-L-asparagine residue. Suitable ligation motifs also include, without limitation, the amino acid sequences $N(NH_2)HV$ or $N(NH_2)GL$ or $N(NH_2)SL$ or $N(NH_2)AL$ or $N(NH_2)IV$. These may be located on the C-terminus of the (poly) peptide, wherein $N(NH_2)$ represents the $N^{\gamma}$-amino-L-asparagine residue.

When reference is herein to "any amino acid", it is typically meant that the respective amino acid can be any naturally occurring amino acid, preferably any one of the 20 proteinogenic (L-)amino acids G, A, V, L, I, M, C, F, W, Y, R, K, H, E, D, Q, N, P, S and T.

In various embodiments where the PAL is VyPAL2 or a variant thereof, the (poly)peptide comprises the amino acid sequence $(X)_oN(OH)X^3X^4(X)_p$ or $(X)_oN(NH_2)X^3X^4(X)_p$, wherein X is any amino acid and o is an integer of at least 2, $X^3$ is G or S, and $X^4$ is a hydrophobic or aromatic amino acid, preferably selected from L, I, V, F, C, W, Y and M, preferably L or F, and p is 0 or an integer of 1 or more and N(OH) is $N^{\gamma}$-hydroxy-L-asparagine and $N(NH_2)$ is Nγ-amino-L-asparagine. It has been found that VyPAL2 works particularly well on these ligation motifs.

Similarly, in various embodiments where the PAL is butelase-1 or a variant thereof, the (poly)peptide comprises the amino acid sequence $(X)_oN(OH)X^3X^4(X)_p$ or $(X)_oN(NH_2)X^3X^4(X)_p$, wherein X is any amino acid and o is an integer of at least 2, $X^3$ is H, and $X^4$ is a hydrophobic or aromatic amino acid, preferably selected from L, I, V, F, C, W, Y and M, preferably V, and p is 0 or an integer of 1 or more and N(OH) is $N^{\gamma}$-hydroxy-L-asparagine and $N(NH_2)$ is $N^{\gamma}$-amino-L-asparagine. Butelase-1 has been found to be particularly efficient for ligation motifs that comprise H as the $X^3$ amino acid.

In various embodiments, the (poly)peptide comprises the N-terminal amino acid sequence $X^1X^2$, wherein $X^1$ is G or H and $X^2$ being G, F, L, V or I.

While the peptide to be cyclized can be any peptide or polypeptide, in various embodiments, it is a peptide hormone or therapeutic peptide. In various embodiments, the peptide may be a beta-amyloid precursor protein-derived inhibitory peptide, which may comprise the amino acid sequence ISYGNNDALMP (SEQ ID NO:5), wherein the D residue may be replaced by N(OH) to allow cyclization. In various other embodiments, the peptide may comprise the amino acid sequence

```
                                        (SEQ ID NO: 6)
CLCRRGVCRCICTISYCDAL
or

                                        (SEQ ID NO: 7)
GGVCPKILKKCRRDSDCPGACICRGNGYCGSGSDIV,

                                        (SEQ ID NO: 8)
GLPVCGETCFGGTCNTPGCSCTWPICTRDIV,

                                        (SEQ ID NO: 9)
GRCTKSIPPICFPDIV,

                                       (SEQ ID NO: 10)
FLaRGDHV,
and

                                       (SEQ ID NO: 11)
ACRCLCRRGDCRCICRGDSL
```

wherein the D residue may be replaced by N(OH) to allow cyclization. Lower case letters indicate D-amino acids.

In various embodiments, the peptide to be cyclized is the linear precursor form of a cyclic cystine knot polypeptide, in particular a cyclotide. Cyclotides are a topologically unique family of plant proteins that are exceptionally stable. They comprise ~30 amino acids arranged in a head-to-tail cyclized peptide backbone that additionally is restrained by a cystine knot motif associated with six conserved cysteine residues. The cystine knot is built from two disulfide bonds and their connecting backbone segments forming an internal ring in the structure that is threaded by the third disulfide bond to form an interlocking and cross braced structure. Superimposed on this cystine knot core motif are a well-defined beta-sheet and a series of turns displaying short surface-exposed loops.

Cyclotides express a diversity of peptide sequences within their backbone loops and have a broad range of biological activities. They are thus of great interest for pharmaceutical applications. Some plants from which they are derived are used in indigenous medicines, including kalata-kalata, a tea from the plant *Oldenlandia affinis* that is used for accelerating childbirth in Africa that contains the prototypic cyclotide kalata B1 (kB1). Their exceptional stability means that they have attracted attention as potential templates in peptide-based drug design applications. In particular, the grafting of bioactive peptide sequences into a cyclotide framework offers the promise of a new approach to stabilize peptide-based therapeutics, thereby overcoming one of the major limitations on the use of peptides as drugs.

The peptides to be cyclized may, in various embodiments, include the linear precursors disclosed in US2012/0244575. This document is for this purpose incorporated herein by reference in its entirety.

In various additional embodiments, the peptides to be cyclized include, but are not limited to linear precursors of peptide toxins and antimicrobial peptides, such as bacteriocins, conotoxins, thanatins (insect antimicrobial peptides) and histatins (human saliva antimicrobial peptides). Other peptides that may be cyclized are precursors of cyclic human or animal peptide hormones, including, but not limited to neuromedin, salusin alpha, apelin and galanin.

Further peptides that can be cyclized using the methods disclosed herein include, without limitation, Adrenocorticotropic Hormone (ACTH), Adrenomedullin, Intermedin, Proadrenomedullin, Adropin, Agelenin, AGRP, Alarin, Insulin-Like Growth Factor-Binding Protein 5, Amylin, Amyloid b-Protein, Amphipathic Peptide Antibiotic, LAH4, Angiotensin I, Angiotensin II, A-Type (Atrial) Natriuretic Peptide (ANP), Apamin, Apelin, Bivalirudin, Bombesin, Lysyl-Bradykinin, B-Type (Brain) Natriuretic Peptide, C-Peptide (insulin precursor), Calcitonin, Cocaine- and Amphetamine-Regulated Transcript (CART), Calcitonin Gene Related Peptide (CGRP), Cholecystokinin (CCK)-33, Cytokine-Induced Neutrophil Chemoattractant-1/growth-related oncogene (CINC), Colivelin, Corticotropin-Releasing Factor (CRF), Cortistatin, C-Type Natriuretic Peptide (CNP), Decorsin, human neutrophil peptide-1 (HNP-1), HNP-2, HNP-3, HNP-4, human defensin HDS, HD6, human beta defensin-1 (hbd1), hbd2, hbd3, hbd4, Delta Sleep-Inducing Peptide (DSIP), Dermcidin-1L, Dynorphin A, Elafin, Endokinin C, Endokinin D, b-Lipotropin, g-Endorphin, Endothelin-1, Endothelin-2, Endothelin-3, Big-Endothelin-1, Big-Endothelin-2, Big-Endothelin-3, Enfuviritide, Exendin-4, MBP, Myelin Oligodendrocyte Protein (MOG), Glu-fibrinopeptide B, Galanin, Galanin-like Peptide, Big Gastrin (Human), Gastric Inhibitory Polypeptide (GIP), Gastrin Releasing Peptide, Ghrelin, Glucagon, Glucagon-like peptide-1 (GLP-1), GLP-2, Growth Hormone Releasing Factor (GRF, GHRF), Guanylin, Uroguanylin, Uroguanylin Isomer A, Uroguanylin Isomer B, Hepcidin, Liver-Expressed Antimicrobial Peptide (LEAP-2), Humanin, Joining Peptide (rJP), Kisspeptin-10, Kisspeptin-54, Liraglutide, LL-37 (Human Cathelicidine), Luteinizing Hormone Releasing Hormone (LHRH), Magainin 1, Mastoparan, alpha-Mating Factor, Mast Cell Degranulating (MCD) Peptide, Melanin-Concentrating Hormone (MCH), alpha-Melanocyte Stimulating Hormone (alpha-MSH), Midkine, Motilin, neuroendocrine regulatory peptide 1 (NERP1), NERP2, Neurokinin A, Neurokinin B, Neuromedin B, Neuromedin C, Neuromedin S, Neuromedin U8, Neuronostatin-13, Neuropeptide B-29, Neuropeptide S (NPS), Neuropeptide W-30, Neuropeptide Y (NPY), Neurotensin, Nociceptin, Nocistatin, Obestatin, Orexin-A, Osteocalcin, Oxytocin, Catestatin, Chromogranin A, Parathyroid Hormone (PTH), Peptide YY, Pituitary Adenylate Cyclase Activating Polypeptide 38 (PACAP-38), Platelet Factor-4, Plectasin, Pleiotrophin, Prolactin-Releasing Peptide, Pyroglutamylated RFamide Peptide (QRFP), RFamide-Related Peptide-1, Secretin, Serum Thymic Factor (FTS), Sodium Potassium ATPase Inhibitor-1 (SPAI-1), Somatostatin, Somatostatin-28, Stresscopin, Urocortin, Substance P, Echistatin, Enterotoxin STp, Guangxitoxin-1E, Urotensin II, Vasoactive intestinal peptide (VIP), and Vasopressin as well as fragments and derivatives thereof. The afore-mentioned peptides may be of human or animal, such as rat, mouse, pig, origin. All of them all well-known to those skilled in the art and their amino acid sequences are readily available.

In various embodiments, the (poly)peptide to be cyclized has a length of 5 to 50 amino acids, for example 10 to 50 amino acids. In various other embodiments, it can be longer and have a length of more than 50 amino acids, for example up to 1000 amino acids, up to 500 amino acids, or 51 to 200 amino acids. The length of the (poly)peptide to be cyclized is not particularly limited, but may be influenced by the presence of other potential ligation motifs in its natural sequence.

All (poly)peptides to be cyclized can be produced by routine techniques known to those skilled in the art, including recombinant expression and chemical synthesis, in particular solid phase synthesis. The artificial N(OH) residue or the complete ligation motif, typically consisting of three amino acids, may be chemically added to the C-terminus of a given (poly)peptide or may be incorporated during the solid phase synthesis at the desired position. The respective technologies and methodologies are widely known in the field of peptide production.

The (poly)peptides to be ligated or cyclized according to the methods disclosed herein can therefore be fusion peptides or polypeptides in which an N(OH) or $N(NH_2)$-containing tag has been C-terminally fused to the (poly) peptide of interest that is to be cyclized. The N(OH)- or $N(NH_2)$-containing tag preferably has the amino acid sequences of the ligation motif for asparaginyl ligases defined above, including the various embodiments. Generally, the to be cyclized (poly)peptides may also carry signaling or detectable moieties.

In the next step of the inventive method, the (poly)peptide to be cyclized with the N(OH) or $N(NH_2)$ residue is contacted with a peptidyl asparaginyl ligase (PAL) under conditions that allow cleavage of the amino acids C-terminal to the $N^{\gamma}$-hydroxy- or $N^{\gamma}$-amino-L-asparagine residue and ligation of the C-terminus of the $N^{\gamma}$-hydroxy- or $N^{\gamma}$-amino-L-asparagine residue to the N-terminus of the (poly)peptide to cyclize the (poly)peptide.

The asparaginyl ligases according to the present invention exhibit protein ligation activity, i.e. are capable of forming a peptide bond between two amino acid residues, with these two amino acid residues herein being located on the same peptides or proteins. This protein cyclase activity includes an endopeptidase activity, i.e. the enzyme forms a peptide bond between two amino acid residues following cleavage of an existing peptide bond. This means that cyclization need not to occur between the termini of a given peptide but can also occur between internal amino acid residues, with the amino acids C-terminal to the amino acid used for cyclization being cleaved off. The asparaginyl ligases disclosed herein are “Asn-specific” in that the amino acid C-terminal to which ligation occurs, i.e. the C-terminal end of the peptide that is ligated, is asparagine (Asn or N). While they may have activity on aspartic acid (Asp or D), too, this activity is typically too weak to allow efficient use, therefore the present methods using N(OH) or $N(NH_2)$ have been developed.

The asparaginyl ligases may be naturally occurring enzymes and may be provided in isolated form. “Isolated”, as used herein, relates to the polypeptide in a form where it has been at least partially separated from other cellular components it may naturally occur or associate with. The asparaginyl ligases may be recombinant polypeptides, i.e. polypeptides produced in a genetically engineered organism that does not naturally produce said polypeptide. Both native and recombinant polypeptides may be post-translationally modified by N-linked glycosylation.

While in principle all PALs with cyclization activity are suitable for the methods described herein, in various embodiments the PAL is selected from butelase-1 and VyPAL2 and OaAEPb1 or variants thereof, as these have been found to have the highest cyclization activity. VyPAL2 may comprise or consist of the amino acid sequence set forth in SEQ ID NO:1 or may be a variant thereof that has an amino acid sequence that has at least 80% sequence identity to the amino acid sequence set forth in SEQ ID NO:1 over its entire length. Butelase-1 may comprise or consist of the amino acid sequence set forth in SEQ ID NO:2 or may be a variant thereof that has an amino acid sequence that has at least 80% sequence identity to the amino acid sequence set forth in SEQ ID NO:2 over its entire length. OaAEP1b may comprise or consist of the amino acid sequence set forth in SEQ ID NO:45 or may be a variant thereof that has an amino acid sequence that has at least 80% sequence identity to the amino acid sequence set forth in SEQ ID NO:45 over its entire length. The asparaginyl ligase consisting of SEQ ID NO:1 is also referred to herein as "VyPAL2" or "VyPAL2 active form/domain". The asparaginyl ligase consisting of SEQ ID NO:2 is also referred to herein as "butelase-1" or "butelase-1 active form/domain". The asparaginyl ligase consisting of SEQ ID NO:45 is also referred to herein as "OaAEPb1" or "OaAEPb1 active form". The full-length polypeptide sequence of VyPAL2 is set forth in SEQ ID NO:3. The full-length polypeptide sequence of butelase-1 is set forth in SEQ ID NO:4.

The variants referred to herein are at least 80%, preferably at least 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 99%, 99.25%, or at least 99.5% identical to the amino acid sequence set forth in SEQ ID NO:1 or 2 or 45 over their entire length. The variants may also be fragments of the respective reference sequence of SEQ ID NO:1 or 2 or 45 that retain their activity. Such fragments are typically C- and/or N-terminally truncated versions of the reference sequence and preferably comprise the determinants for the activity of the enzyme as defined herein below. The same definition of variants applies to the respective full-length sequences set forth in SEQ ID Nos. 3 and 4.

In various embodiments, the variant may be a precursor of the mature enzyme.

The identity of nucleic acid sequences or amino acid sequences is generally determined by means of a sequence comparison. This sequence comparison is based on the BLAST algorithm that is established in the existing art and commonly used (cf. for example Altschul et al. (1990) "Basic local alignment search tool", J. Mol. Biol. 215:403-410, and Altschul et al. (1997): "Gapped BLAST and PSI-BLAST: a new generation of protein database search programs"; Nucleic Acids Res., 25, p. 3389-3402) and is effected in principle by mutually associating similar successions of nucleotides or amino acids in the nucleic acid sequences and amino acid sequences, respectively. A tabular association of the relevant positions is referred to as an "alignment." Sequence comparisons (alignments), in particular multiple sequence comparisons, are commonly prepared using computer programs which are available and known to those skilled in the art.

A comparison of this kind also allows a statement as to the similarity to one another of the sequences that are being compared. This is usually indicated as a percentage identity, i.e. the proportion of identical amino acid residues at the same positions or at positions corresponding to one another in an alignment. Indications of identity can be encountered over entire polypeptides or only over individual regions. Identical regions of various amino acid sequences are therefore defined by way of matches in the sequences. Such regions often exhibit identical functions. They can be small, and can encompass only a few amino acids. Small regions of this kind often perform functions that are essential to the overall activity of the protein. It may therefore be useful to refer sequence matches only to individual, and optionally small, regions. Unless otherwise indicated, however, indications of identity herein refer to the full length of the respectively indicated nucleic acid sequence or amino acid sequence.

In various embodiments, the variants of butelase-1 and VyPAL2 and OaAEPb1 described herein comprise the amino acid residue N at the position corresponding to position 19 of SEQ ID NO:1; and/or the amino acid residue H at the position corresponding to position 124 of SEQ ID NO:1; and/or the amino acid residue C at the position corresponding to position 166 of SEQ ID NO:1. In various embodiments, at least the catalytic dyad formed by the amino acid residue H at the position corresponding to position 124 of SEQ ID NO:1 and the amino acid residue C at the position corresponding to position 166 of SEQ ID NO:1 is present, preferably in combination with the amino acid residue N at the position corresponding to position 19 of SEQ ID NO:1, thus forming the complete catalytic triad. It has been found that these amino acid residues are necessary for the catalytic activity (ligase activity) of the polypeptide. In preferred embodiments, the variants thus comprise at least two, more preferably all three of the above indicated residues at the given or corresponding positions.

All amino acid residues are generally referred to herein by reference to their one letter code and, in some instances, their three-letter code. This nomenclature is well known to those skilled in the art and used herein as understood in the field.

In various embodiments, the variants referred to herein comprise the amino acid residue A at the position corresponding to position 126. In various embodiments, the variants referred to herein comprise the amino acid residue A or P, preferably P, at the position corresponding to position 127 of SEQ ID NO:1. Alternatively, the amino acid residue at the position corresponding to position 126 of SEQ ID NO:1 may be G. In these embodiments, the amino acid residue at the position corresponding to position 127 of SEQ ID NO:1 is preferably A. These motifs AP, AA and GA are also referred to herein as Ligase Activity Determinant 2 (LAD2), as they are critical determinants for the ligase activity. In various embodiments the motif at the positions corresponding to positions 126 and 127 of SEQ ID NO:1 is not GP, but either AP, AA or GA.

In various embodiments, the variants referred to herein comprise the amino acid residue W or Y at the position corresponding to position 195, the amino acid residue I or V at the position corresponding to position 196, and the amino acid residue T, A or V at the position corresponding to position 197 of SEQ ID NO:1. It has been found that this motif W-I/V-T/A/V, also referred to herein as Ligase Activity Determinant 1 (LAD1), is also a critical determinant for the ligase activity. In addition to the known gatekeeper position that corresponds to position 196 in SEQ ID NO:1, it has been found that also positions 195 and 197, in particular 195, are relevant for determining ligase/endopeptidase activity.

In various embodiments, the variants referred to herein comprise the amino acid residues R at the position corresponding to position 21, H at the position corresponding to position 22, D at the position corresponding to position 123, E at the position corresponding to position 164, S at the position corresponding to position 194, and D at the position corresponding to position 215 of SEQ ID NO:1. These amino acid residues are also referred to herein as "S1 pocket", which has also been found to be involved in ligase activity.

In various embodiments, the variants referred to herein comprise the amino acid residues C at the positions corresponding to positions 199 and 212 of SEQ ID NO:1. These two residues typically form a disulfide bridge in the mature polypeptide, which contributes to ligase activity.

The variants of the invention may, in various embodiments, comprise further more or less invariable sequence elements, such as the poly-Pro loop (PPL). Said loop has the consensus sequence P/A-G/T/S-X-P/E-G/D/P-V/F/A/P-P-UP/A/E-E and comprises at least 2 and up to 5 proline residues. Typical are 2, 3, 4 or 5 proline residues at the indicated positions. The PPL occupies positions 200-208 of SEQ ID NO:1.

Another motif that may be present in the variants of the invention is the so-called MLA motif spanning residues 244-249 of SEQ ID NO:1. This may have the sequence KKIAYA or NKIAYA (SEQ ID Nos. 5 and 6).

In various embodiments, the variants of the invention comprise the LAD1 and LAD2 motifs as described above. In further embodiments, they additionally comprise one, two, three or all four of the S1 pocket, SS bridge, PPL and MLA motif, as defined above. The presence of these motifs ensures their functionality as ligases even if other parts of the sequence are modified.

In various embodiments, the variants comprise fragments of the asparaginyl ligases described herein, with said fragments retaining enzymatic activity. It is preferred that they have at least 50%, more preferably at least 70, most preferably at least 90% of the protein ligase and/or cyclase activity of the initial molecule, preferably of the polypeptide having the amino acid sequence of SEQ ID NO:1 or 2. The fragments are preferably at least 150 amino acids in length, more preferably at least 200 or 250. It is further preferred that these fragments comprise the amino acids N, H and C at positions corresponding to positions 19, 124 and 166 of SEQ ID NO:1 as well as the above-defined LAD1, LAD2 and optionally also any one or more of the S1 pocket, the PPL, MLA motif and disulfide bridge contained in the initial molecule. Preferred fragments therefore comprise amino acids 19-197, more preferably 19-212, most preferably 19-249 corresponding to the respective positions in the amino acid sequence set forth in SEQ ID NO:1.

It is preferred that the variants of the invention have at least 50%, more preferably at least 70, most preferably at least 90% of the protein ligase activity of the enzyme they are derived from.

In various embodiments, the variants are capable of ligating/cyclizing a given peptide with an efficiency of 60% or more, preferably 80% or more, preferably at a pH of 5.5 or higher. The cyclization activity may also be determined at pH values of 6.0, 6.5, 7.0, 7.5 or higher. This is relevant, since at low pH conditions, such as below pH 5, the ligases may exhibit a certain degree of endopeptidase activity.

The variants of butelase-1 and VyPAL2 and OaAEPb1 according to the embodiments described herein can comprise amino acid modifications, in particular amino acid substitutions, insertions, or deletions. Such variants are, for example, further developed by targeted genetic modification, i.e. by way of mutagenesis methods, and optimized for specific purposes or with regard to special properties (for example, with regard to their catalytic activity, stability, etc.). If such additional modifications are introduced into the asparaginyl ligases of the invention, these preferably do not affect, alter or reverse the sequence motifs detailed above, i.e. the catalytic residues, the LAD1 and LAD2 motifs. This means that the above-defined features of these residues/motifs are not changed by these additional mutations beyond that what is defined above. It can be further preferred that additionally one, two, three or all four of the S1 pocket, SS bridge, PPL and MLA motif are retained without additional modifications, i.e. modifications going beyond those detailed above.

In various embodiments, the polypeptides having ligase/cyclase activity may be post-translationally modified, for example glycosylated. Such modification may be carried out by recombinant means, i.e. directly in the host cell upon production, or may be achieved chemically or enzymatically after synthesis of the polypeptide, for example in vitro.

For example, butelase-1 (SEQ ID NO:4) is glycosylated at N94 and N286 with bulky heterogeneous glycans, which results in an increase of additional mass of about 6 kDa. The recombinant VyPAL2 (SEQ ID NO: 3) is glycosylated at positions N102, N145 and N237, with small glycans, and which results in an additional increased mass of about 3 kDa. The polypeptides of the invention may thus be glycosylated with bulky, heterogeneous glycans, for example at positions corresponding to positions N94 and N286 of SEQ ID NO:4 or with small glycans at positions corresponding to positions N102, N145 and N237 of SEQ ID NO:3.

In the methods and uses described herein, the enzyme, i.e. the asparaginyl ligases, and the substrate, i.e. the (poly) peptide to be cyclized, can be used in a molar ratio of 1:100 or higher, preferably 1:400 or higher, more preferably at least 1:1000. The reaction is typically carried out in a suitable buffer system at a temperature that allows optimal enzyme activity, usually between ambient (20° C.) and 40° C.

Immobilizing enzymes on solid supports has a long history with a primary goal of lowering enzyme consumption by repetitively using the same batch of enzymes. In addition, site-separation of solid-phase immobilization reduces aggregation, leading to increased stability and activity of biocatalysts, and simplifies the purification by avoiding contamination of products by enzymes. Consequently, immobilized biocatalysts have been developed for industrial uses to a billion-scale market, such as immobilized lactase in food industry and immobilized lipase in biodiesel production. Compared with conventional industrial processes using chemical catalysts, immobilized enzymes are economically attractive and environmentally friendly. There are three main-stream immobilization technologies, including attachment to carriers either or non-covalently, physical entrapment, and self-crosslinking. For biocatalysts such as the PALs described herein that have an exposed substrate-binding surface for biomolecule-based substrates, strategies based on attachment to hydrophilic porous resins by either covalent-binding and affinity-binding methods are direct, convenient, and feasible to facilitate their performance in aqueous conditions. The thus immobilized asparaginyl ligases are stable, reusable and highly efficient in mediating macrocyclization and site-specific ligation reactions.

Accordingly, in the methods of the present invention the asparaginyl ligase may be immobilized on a solid support. The major advantages of immobilization on a solid support provide site separation and pseudo-dilution to prevent trans-autolytic degradation and enhance stability. Site-separation of immobilized enzymes permits the use of high enzyme concentrations to accelerate ligation reactions to complete in minutes, such as cyclization, cyclooligomerization and ligation reactions either under one-pot conditions or in a continuous flow-reactor. Suitable support materials include various resins and polymers that are used in chromatography columns and the like. The support may have the form of beads or may be the surface of larger structure, such as a microtiter plate. Immobilization allows for a very easy and simple contacting with the substrate, as well as easy separation of enzyme and substrate after the synthesis. If the polypeptide with the enzymatic function is immobilized on a solid column material, the ligation/cyclization may be a continuous process and/or the substrate/product solution may be cycled over the column.

In various embodiments, the asparaginyl ligase is glycosylated and the immobilization is facilitated by interaction with a carbohydrate-binding moiety, preferably a concanavalin A moiety or variant thereof, covalently linked to the solid support. In such embodiments, the solid support may be an agarose bead.

In various other embodiments, the asparaginyl ligase is biotinylated and the immobilization is facilitated by interaction with a biotin-binding moiety, preferably a streptavidin, avidin or neutravidin moiety or variant thereof, covalently linked to the solid support. Functionalization of the enzyme with the biotin may be achieved using methods known in the art, such as functionalization with a biotin ester with N-hydroxysuccinimide (NHS), such as succinimidyl-6-(biotinamido)hexanoate. In such embodiments, the solid support may be an agarose bead and the biotin-binding moiety may be an avidin variant, such as neutravidin (deglycosylated avidin).

In various other embodiments, the asparaginyl ligase is immobilized on the solid support by reaction of free amino groups in the polypeptide, for example from lysine side chains, with an N-hydroxysuccinimide functional group on the surface of the solid support. The solid support may be agarose beads.

In all these embodiments, the asparaginyl ligases may be the butelase-1 and variants thereof or VyPAL2 and variants thereof or OaAEPb1 and variants thereof, as described herein.

The cyclized (poly)peptides may be subjected to mild oxidative conditions after the cyclization reaction to allow conversion of the N(OH) or N($NH_2$) residue to a D residue, if desired.

The invention further relates to the cyclized (poly)peptides obtained and obtainable according to the methods of the invention. These are characterized in that they comprise at least one N(OH) or N($NH_2$) residue. The inventio further encompasses the cyclized polypeptides after the N(OH) residue has been converted to a D residue.

Specific examples of cyclic peptides that are comprised in the scope of the present invention include all peptides specifically disclosed in the examples, in particular those derived from or having the amino acid sequences set forth in SEQ ID Nos. 14-18, 21, and 34-37.

The invention also relates to the use of peptidyl asparaginyl ligases to cyclize a (poly)peptide comprising a ligation motif comprising a N(OH) or N($NH_2$) residue. All embodiments disclosed herein for the inventive methods similarly apply to these uses.

The invention is further illustrated by the following non-limiting examples and the appended claims.

EXAMPLES

Materials and General Methods

All the solvents and reagents were purchased from commercial suppliers and used without further purification. The synthesis of Fmoc-Asn(OTrt)-COOH and Fmoc-Asn(Me)-COOH were done under a positive pressure of $N_2$ atmosphere. Evaporations of solvents were performed using a Buchi rotary evaporator. The completion of the reactions was monitored using 0.25 cm silica thin-layer chromatography (TLC). Since the Asn compounds contain the Fmoc group, the spots on TLC can be visualised under UV light. The synthesized Asn compounds were purified using 200 mesh silica column chromatographs, eluting with ethyl acetate/hexanes or MeOH/DCM solvent system. Peptides were synthesized following standard Fmoc solid phase synthesis protocols. Synthesized peptides were purified using semi-preparative RP-HPLC. Semi-preparative RP-HPLC was preformed using a Shimadzu HFLC system equipped with a Phenomenex jupiter-C18 RP column (10×250 mm, 5 μm) with a flow rate of 2.5 mL per minute, eluting using a gradient of buffer B (90% acetonitrile, 10% $H_2O$, 0.045% TFA) in buffer A ($H_2O$, 0.045% TFA). All the synthesized compounds were stored at 4° C. or −20° C.

For analysis, $^1H$ and $^{13}C$ NMR spectra were recorded using a Bruker 400 MHz spectrometer. Samples were dissolved in deuterated solvents and the spectra were obtained at 298 K. All chemical shifts were quoted in ppm and coupling constants were measured in Hz. Mass spectra for peptides were obtained using a Bruker Ultraflex Extreme Matrix Assisted Laser Desorption/Ionization (MALDI) Tandem TOF or electrospray ionization (ESI) mass spectroscopy (Thermo Fisher LTQ XL). Data from MALDI was analysed using Data Explorer software and data from ESI was analysed using Thermo Xcalibur Qual Browser software. For characterization of Asn compounds, HRMS (ESI) were recorded using a 6520 QTOF mass spectrometer, equipped with a dual-spray electrospray ionization source (Agilent Technology, Santa Clara, CA). Analytical reverse-phase HPLC (RP-HPLC) was performed on a Shimadzu HPLC system equipped with a Phenomenex jupiter-C18 RP column (4.6×250 mm, 5 μm) with a flow rate of 1.0 mL per minute, eluting with a gradient of buffer B (90% ACN, 10% $H_2O$, 0.045% TFA) in buffer A ($H_2O$, 0.045% TFA).

Solid Phase Peptide Synthesis (SPPS)

All the peptides were synthesized as C-terminal amides using Rink amide MBHA resin or 2-chlorotrityl chloride resin by standard Fmoc chemistry. Before use, the resin was pre-swelled in DCM for 20 min. The resin was then washed with DMF, DCM and DMF successively. The appropriate Fmoc-protected amino acids (4 eq) and PyBop (4 eq) were dissolved in DMF/DCM (50%/50%). DIEA (8 eq) was added into the mixture to activate the Fmoc-amino acid. The solution was added to the resin and shaken for one hour at room temperature. The resin was then washed with DMF (3 times), DCM (3 times), successively. The completion of coupling was tested using the Ninhydrin reagent. To deprotect Fmoc, the resin was treated with 20% piperidine in DMF (2×10 min). The resin was then washed with DMF (3 times), DCM (3 times), successively. For peptide cleavage from resin and deprotection of sidechain protecting groups at the end of SPPS, the peptidyl-resin was treated with a cocktail of TFA/$H_2O$/TIS (95%/2.5%/2.5%) and the mixture was shaken for 1-3 hours. For Cys-containing peptides, TFA/$H_2O$/TIS/EDC (92.5%/2.5%/2.5%/2.5%) was used for cleavage. The cleavage solution was separated from the resin by filtration and the cleaved peptide was precipitated in the cold $Et_2O$ (20-30 mL). The crude product was isolated by centrifugation and purified by reverse-phase HPLC. The peptide fractions after HPLC purification were freeze-dried to afford the peptide in powder form.

Conditions of Enzyme-Mediated Reactions

Enzyme-meditated cyclization and ligation reactions were performed in 20 mM PBS buffer (pH 6.5) at 37° C. with 0.5 mM TCEP. The reaction was quenched by adding 20% TFA. The enzyme concentration was determined by the absorbance at 280 nm using Nanodrop. The reactions were monitored by reverse-phase analytical HPLC, and the products were characterized by MALDI-MS or ESI-MS.

Kinetic Studies

Model peptides (1-6, see Table 51) were used in the kinetic studies. The cyclization reaction was performed in 20 mM PBS buffer (pH 6.5) containing 0.5 mM TCEP, at 37° C. The reaction was monitored by analytical RP-HPLC (5% buffer B-45% buffer B in 20 min). Kinetic constants for these peptides were obtained from the initial reaction rates. To ensure that the measurement of reaction rate was in the range of the initial velocity, the reaction was quenched using 20% TFA, when less than 25% of the substrate has been converted. Each recorded value is an average of measurements in triplicate. All the numbers were input into GraphPad Prism (GraphPad Software, San Diego) to obtain the Michaelis-Menten curve and calculate the kinetic parameters ($k_{cat}$ and $K_m$).

Chemical Cyclization of RTD-1

RTD1 was synthesized as hydrazine peptide using well-established protocols (Zheng et al. *ChemBioChem.,* 2012, 13, 542-546) The hydrazine peptides were treated with 2 eq of $NaNO_2$ in a 6M Guanidine HCl buffer (pH 3) at −20° C. for 10 min. 100 eq of MESNa in PBS buffer (pH 7) was added into the reaction mixture, and the pH was adjusted to pH 7. After leaving the solution for 30 min at RT, 10 mM TCEP was added into solution and the thiolester was purified by RP-HPLC. The thiolester peptide was then dissolved in a pH 7-buffer (20 mM PBS, 1 mM GSH) for 16 h to afford the cyclic and folded RTD-1.

Oxidative Folding

Peptides were folded in 0.1 M $NH_4CO_3$ buffer (pH 8) with 10% DMSO and GSSG/GSH (10 eq/100 eq), for around 8-12 hours at 4° C. The Asn(OH)-RTD1, Asp-RTD1 and Asn-RTD1 peptides were folded in 0.1 M Tris-HCl (pH 8.5), 2 M urea with GSSG/GSH (10 eq/100 eq), for around 12 h at 4° C. The folded products were purified by RP-HPLC and characterized by ESI-MS, then were purified and immediately lyophilized and stored at −20° C.

Converting Asn(OH) to Asp $NaIO_4$ (1 eq) was added into a 20 mM PBS buffer (pH 7.4) containing 200 μM of Asn(OH) peptide and 10 eq of methionine was added as a scavenger to prevent over-oxidation of sensitive residues. The reaction mixture was left on ice for 5-10 min, then subjected to purification by HPLC. The completion of the reaction was confirmed by peak shift on RP-HPLC and mass spectra analysis. The product was afforded as a white powder after lyophilization, and was stored in −20° C.

NMR Measurement and Structure Calculation

The NMR of the Asn(OH)-RTD1 cyclic peptide was measured in $H_2O/D_2O$ (90:10), pH ~4, at a concentration of 0.6 mM. $^1H$-$^1H$ TOCSY and $^1H$-$^1H$ NOESY were acquired on a Bruker Avance-600 spectrometers at 298K. 10 μM Sodium 2,2-dimethyl-2-silapentane-5-sulfonate (DSS) was used as an internal reference. $^1H$-$^1H$ TOCSY spectrum was interpreted using NMRFAM sparky (Lee et al. *Bioinformatics.,* 2015, 31, 1325-1327) for amino acid sequence assignment. Prediction of the torsion angles was performed on a web-base server PREDITOR (Berjanskii et al. *Nucleic Acids Res.,* 2006, 34, W63-W69). The distance constraints were obtained from NOE cross peaks. Based on the distance and the torsion angle constraints, 20 lowest-energy structure conformers were calculated using CYANA (Güntert et al. *J. Mol. Biol.,* 1997, 273, 283-298).

Measurement of Circular Dichroism (CD) spectra

The samples for CD measurement were confirmed to be over 95% pure by HPLC. Around 0.1 mg/mL of linear MCOTI-II, acyclic MCOTI-II and cyclic MCOTI-II were dissolved in 20 mM PBS (pH 7.4), placed in a cell with 1 mm path length. The CD spectra were recorded from 200 nm to 260 nm at 25° C. The final spectra were obtained by averaging 3 independently measured CD spectra of the same sample and then subtracting the CD spectrum of pure buffer.

MMPs Inhibition Assay

The inhibitory activity of the peptides was determined by measuring the MMPs' protease activity towards a FRET substrate. 0.8 nM MMP2 or MMP9 (Sigma-Aldrich), 10 μM substrate (FAM-Lys-Pro-Leu-Gly-Leu-Lys(Dabcyl)-Ala-Arg-$NH_2$, λex 490 nm; λem 520 nm) and various concentrations of the peptides (0.0001 μM-10 μM or 0.001 μM-100 μM) were used. The reactions were performed in 50 mM Tris-HCl buffer (pH 7.5) containing 150 mM NaCl, 10 mM $CaCl_2$, 0.05% Brij35, at 37° C. MMP2 was pre-incubated with the peptide inhibitors for 10 min before adding the substrate. All the numbers were input into GraphPad Prism (GraphPad Software, San Diego) for $IC_{50}$ calculation. The inhibition constants ($K_i$) were calculated according to the equation: $K_i=IC_{50}/(1+[S]_o/K_m)$, where $IC_{50}$ is the peptide concentration when 50% of the enzymatic activity is inhibited, $[S]_0$ is the initial substrate concentration (10 μM), and $K_m$ is the Michaelis-Menten constant. MMP2 has a $K_m$ of 18.83±4.58 μM, and MMP9 have a $K_m$ of 16.23±0.8 μM towards the FRET substrate.

Trypsin Inhibition Assay

The inhibitory activity of MCoTII and SFTI was determined by measuring trypsin's protease activity towards a FRET substrate. 0.1 nM trypsin, 12 μM substrate [GISTGPE (Edans)RVNSL-QQLVRK(Dabcyl)G-$NH_2$, λex 360 nm; λem 490 nm] and various concentrations of the peptides (0.01 nM-500 nM) were applied. The reactions were performed in 50 mM Tris-HCl (pH 8, 100 mM NaCl) solution at 37° C. Trypsin was pre-incubated with the peptide inhibitors for 10 min before adding the substrate. All the numbers were input into GraphPad Prism (GraphPad Software, San Diego) for $IC_{50}$ calculation. The inhibition constants ($K_i$) were calculated according to the equation: $K_i=IC_{50}/(1+([S]_o/K_m)$, where $IC_{50}$ is the peptide concentration when 50% of the enzymatic activity is inhibited, $[S]_0$ is the initial substrate concentration (10 μM), and $K_m$ is the Michaelis-Menten constant of the FRET substrate, which is 1.19±0.23 μM.

Plasma Stability Determination by HPLC Analysis

Peptides were mixed with human serum to a final concentration of 100 μM and incubated at 37° C. Aliquots of the sample were taken out at different time points and 10% TFA was added to quench all protease activities, followed by addition of 10% of DMSO. The solution mixture was centrifuged (11,000 g, 5 min, 4° C.) and the supernatant was analysed by RP-HPLC (15% buffer B-65% buffer B in 25 min) and ESI-MS. The quantity of the remaining peptides was determined by comparing their HPLC peak area with the initial peak area.

Butelase-1 Extraction

Plant flowers of *Clitoria ternatea* grown in the Nanyang Technological University Herb Garden were collected. Butelase-1 was extracted using a chromatography method described previously.[5] Purified butelase-1 was obtained and stored at 4° C. or −80° C. in 50 mM sodium phosphate buffer (pH 6.0) containing 1 mM EDTA, 5 mM β-mercaptoethanol, 0.01% Tween 20 and 20% sucrose.

VyPAL2 Expression and Activation

VyPAL2 was expressed using sf9 insect cells as described previously (Hemu et al. *PNAS,* 2019, 116, 11737-11746). 100 mL of the viral vector containing VyPAL2 gene was used to infect sf9 cells at cell density of 2.5x106 cells/mL. MOI for infection was set between 1-10 for protein expression. The culture was incubated at 27° C. shaker for 3 days (72 hours) at 135 rpm. Protein purification was performed in three steps: Immobilized Metal Affinity Chromatography (IMAC), Ion-Exchange Chromatography (IEX), and Size-Exclusion chromatography (SEC). Pro-VyPAL2 was activated at pH 5 in 50 mM sodium citrate buffer (0.1 M NaCl, 1 mM DTT, 0.5 mM LS) for 2-3 h at 37° C. After activation, the activated enzyme was purified by SEC at pH 6.5 (20 mM PBS, 0.1 M NaCl, 1 mM DTT).

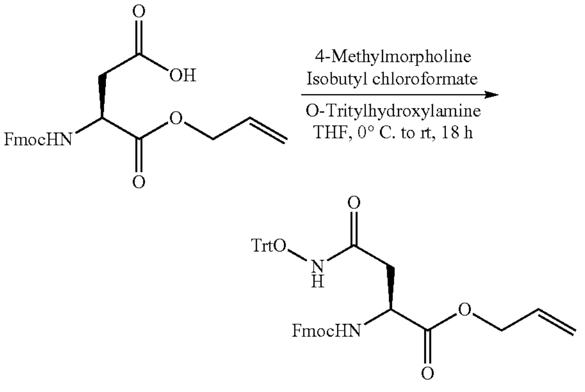

a (S)-3-((((9H-Fluoren-9-yl)methoxy)carbonyl)amino)-4-(allyloxy)-4-oxobutanoic acid (a)

4-Methylmorpholine (0.72 mL, 5.57 mmol) was added to a solution of Fmoc-Asp-OAll (2.0 g, 5.06 mmol) in anhydrous THF (20 mL), followed by isobutyl chloroformate (0.62 mL, 5.57 mmol) at 0° C. The solution was stirred at 0° C. for 10 min and O-tritylhydroxylamine (1.39 g, 5.06 mmol) was added. Reaction mixture was allowed to stir at rt for 18 h under $N_2$ at room temperature. The reaction was quenched by saturated aqueous $NH_4Cl$ (30 mL) and the reaction mixture extracted with ethyl acetate (3x30 mL). The combined organic layer was dried over anhydrous $Na_2SO_4$, evaporated under vacuum. The crude product was purified using column chromatography (10% EA to 40% EA in Hexanes) to afford compound a (2.7 g, 85%) as off-white solid.

$^1H$ NMR (400 MHz, $CDCl_3$) δ 7.80 (d, J=7.6 Hz, 2H), 7.64 (m, 2H), 7.44 (d, J=7.5 Hz, 2H), 7.35 (m, 15H), 5.88 (m, 1H), 5.82 (dd, J=26.1 Hz, 13.6 Hz, 2H), 4.61 (m, 2H), 4.47 (m, 1H), 4.40 (m, 1H), 4.30 (m, 2H), 2.44 (d, J=15.6 Hz, 1H), 1.95 (d, J=17.1 Hz, 1H); $^{13}C$ NMR (100 MHz, $CDCl_3$) δ 174.1, 170.7, 155.9, 143.8, 141.4, 141.3, 140.8, 131.8, 129.1, 128.3, 127.8, 127.1, 125.2, 120.0, 118.4 93.9, 67.2, 66.1, 49.5, 47.2, 34.6; HRMS(ESI): m/z calculated for $C_{41}H_{36}N_2NaO_6$ $[M+Na]^+$ 675.24711, found 675.24702.

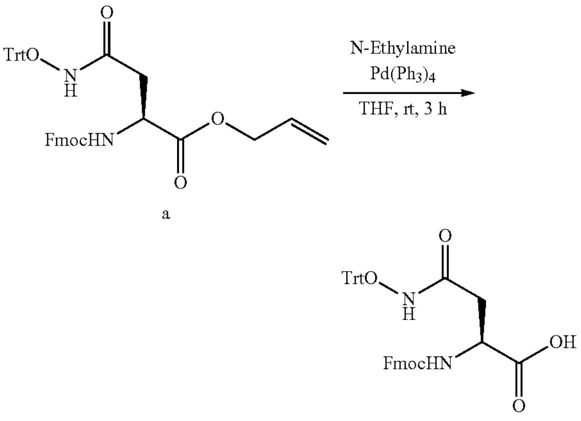

a b $N^2$-(((9H-Fluoren-9-yl)methoxy)carbonyl)-$N^4$-(trityloxy)-L-asparagine (b)

N-Ethylaniline (1.62 mL, 12.9 mmol) was added into a solution of Fmoc-Asn(OTrt)-All (2.7 g, 4.3 mmol) in anhydrous THF (20 mL) and degassed with $N_2$ for 10 min. $Pd(PPh_3)_4$ (0.35 g, 0.43 mmol) was added and the reaction mixture was stirred for 3 h under $N_2$ at room temperature. The reaction was quenched using $H_2O$ (10 mL) and the reaction mixture extracted with ethyl acetate (3x20 mL). The combined organic layer was dried over anhydrous $Na_2SO_4$, evaporated under vacuum. The crude product was precipitated in diethyl ether to afford compound b (2.0 g, 77%) as pale-yellow solid. HRMS(ESI): m/z calculated for $C_{38}H_{32}N_2NaO_6$ $[M+Na]^+$ 635.21581, found 635.21545.

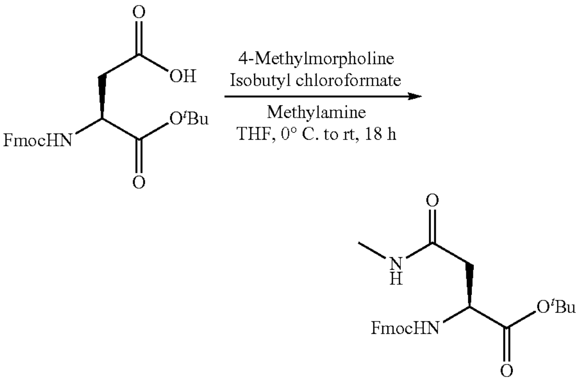

c tert-Butyl $N^2$-(((9H-fluoren-9-yl)methoxy)carbonyl)-$N^4$-methyl-L-asparaginate (c)

4-Methylmorpholine (0.15 mL, 1.34 mmol) was added to a solution of Fmoc-Asp-O$^t$Bu (0.50 g, 1.22 mmol) in anhydrous THF (20 mL), followed by isobutyl chloroformate (0.17 mL, 1.34 mmol) at 0° C. The solution was stirred at 0° C. for 10 min and methylamine in $H_2O$ (1 mL, 3.66 mmol) was added. Reaction mixture was allowed to stir at rt for 18 h under $N_2$ at room temperature. The reaction was quenched by saturated aqueous $NH_4Cl$ (30 mL) and the reaction mixture extracted with ethyl acetate (3×30 mL). The combined organic layer was dried over anhydrous $Na_2SO_4$, evaporated under vacuum. The crude product was purified using column chromatography (10% EA to 40% EA in Hexanes) to afford compound c (0.42 g, 81%) as off-white solid. $^1$H NMR (400 MHz, $CDCl_3$) δ 7.77 (d, J=7.13 Hz, 2H), 7.62 (d, J=6.48 Hz, 2H), 7.41 (d, J=7.13 Hz, 2H), 7.32 (d, J=6.48 Hz, 2H), 4.48 (m, 1H), 4.37 (m, 2H), 4.23 (t, J=6.84 Hz, 1H), 2.89 (m, 1H), 2.78 (d, J=3.87 Hz, 3H), 2.71 (m, 1H); $^{13}$C NMR (100 MHz, $CDCl_3$) δ 170.5, 170.1, 156.3, 143.9, 143.8, 141.28, 127.7, 127.1, 125.2, 120.0, 82.4, 67.1, 51.5, 47.1, 37.9, 27.9, 26.3; HRMS(ESI): m/z calculated for $C_{24}H_{29}N_2O_5$ $[M+H]^+$ 425.20765, found 425.20680.

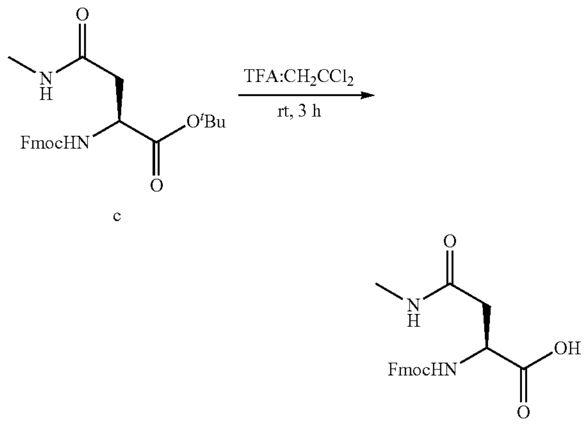

c d

$N^2$-(((9H-Fluoren-9-yl)methoxy)carbonyl)-$N^4$-methyl-L-asparagine (d)

Fmoc-Asn(Me)-O$^t$Bu (0.42 g, 0.99 mmol) was dissolved in 1:1 $CH_2Cl_2$/TFA and stirred for 3 h. Reaction mixture was evaporated and the crude solid was washed with diethyl ether to afford compound d (0.35 g, 95%) as off-white solid. HRMS(ESI): m/z calculated for $C_{20}H_{21}N_2O_5$ $[M+H]^+$ 369.13722, found 369.14514.

Example 1

Figure 5:
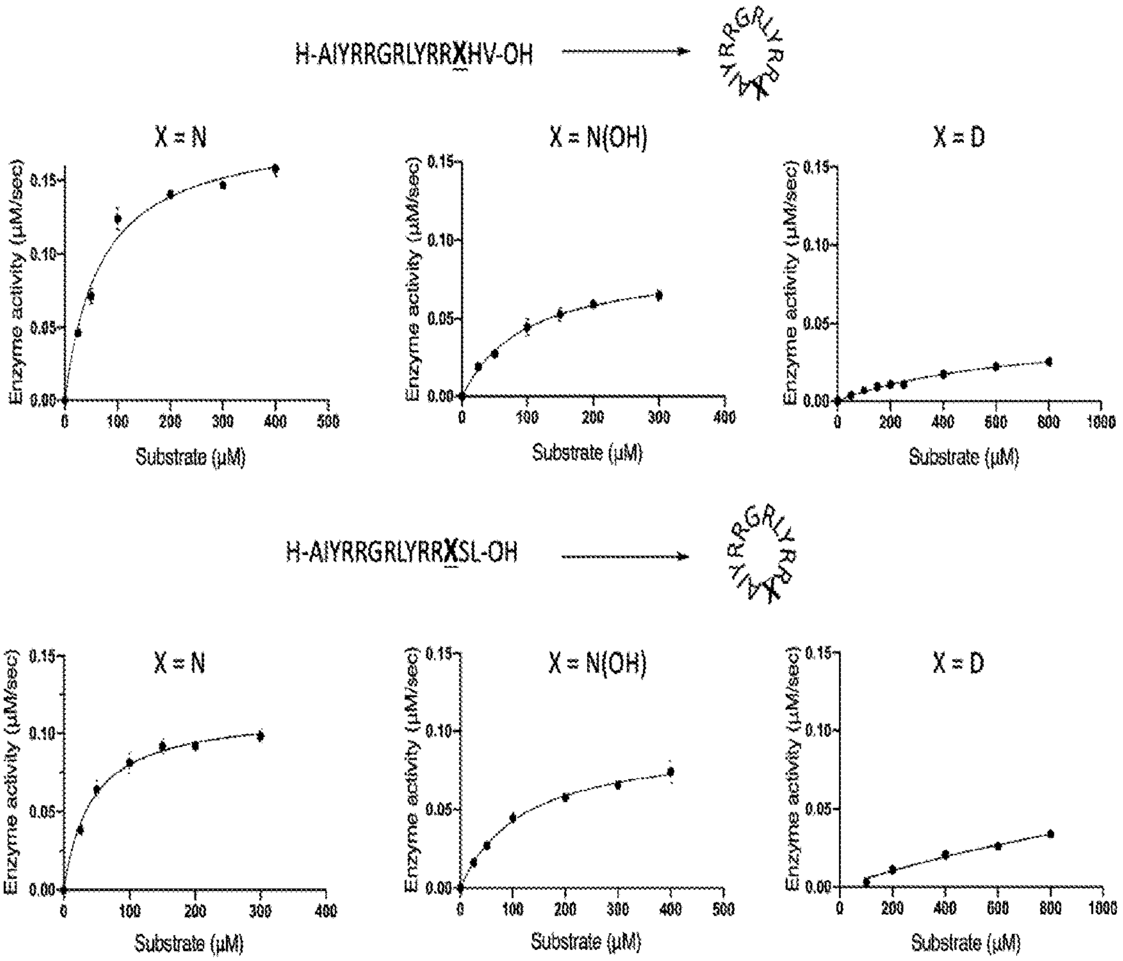
FIG. 5. Kinetics of the cyclization of AX12-XX peptides (1-6) by the catalysis of butelase-1 or VyPAL2. The cyclization reactions were performed at 37° C. in the presence of various concentrations of the peptide substrates in 20 mM PBS (pH 6.5) for 10 min. AX12-HV peptides were cyclized by butelase-1 and AX12-SL peptides were cyclized by VyPAL2. The amount of the ligase used was 12.5 nM (for peptide 1), 25 nM (for peptide 2 and 4), 100 nM (for peptide 3 and 5) or 200 nM (for peptide 6). The reactions were monitored by analytical RP-HPLC. All data are presented as means±SEM. Sequences are set forth in SEQ ID Nos. 17-22.
Figure 6:
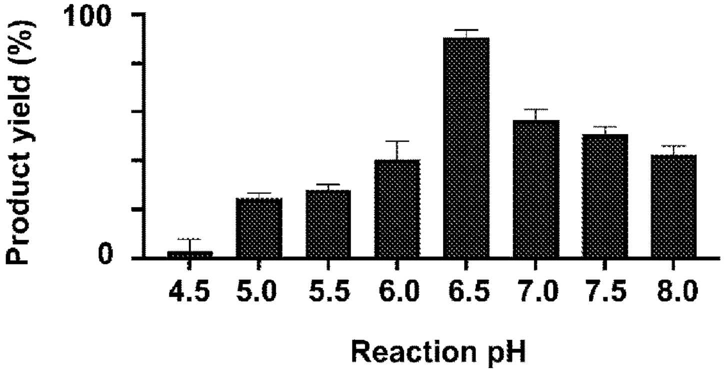
FIG. 6. Ligase activity of Butelase-1 towards P1-Asn (OH). 200 JAM AN(OH)12-HV 2 was treated with butelase-1 (0.001 eq) under pH4.5-8 at 37° C. for 12 min. The reactions were monitored by analytical RP-HPLC. All data are presented as means±SEM.

Fmoc-Asn(OTrt)-COOH was synthesized and used in Fmoc solid phase peptide synthesis to introduce Asn(OH) at the P1 position of PAL substrate peptides. To investigate the effects of P1-Asn, P1-Asn(OH), and P1-Asp on reaction kinetics, six peptides of the sequence AIYRRGRLRRXHV or AIYRRGRLYRRXSL [P1-X=Asn, Asn(OH) or Asp] (Table 1 and S1) were prepared as substrates of butelase-1 or VyPAL2, respectively, both having almost exclusive ligase activity (Nguyen et al. *Nat. Chem. Biol.,* 2014, 10, 732-738; Hemu et al. *Proc. Natl. Acad. Sci.,* 2019, 116, 11737-1174). The catalytic efficiency of butelase-1 on the N(OH)HV substrate 2 is ~6-fold lower than that of the NHV peptide 1 but 48-fold higher than that of the DHV peptide 3 (Table 1 and FIG. 5). Similarly, the catalytic efficiency of VyPAL2 on the N(OH)SL peptide 5 is ~14-fold lower than that of the NSL peptide 4 but 28-fold higher than that of the DSL peptide 6 (Table 1). In general, the P1-Asn(OH) peptides exhibit a much higher binding affinity ($K_m$) and catalytic turnover ($k_{cat}$) than the native P1-Asp peptides.

TABLE 1

Kinetics of peptide cyclization by butelase-1 and VyPAL2

| No | Sequence | $K_{cat}$ ($s^{-1}$) | $K_m$ (μM) | $K_{cat}/K_m$ ($M^{-1}/s^{-1}$) |
|---|---|---|---|---|
| 1 | AIYRRGRLYRRNHV[a] (SEQ ID NO: 17) | 14.86 ± 0.34 | 67.5 ± 2.8 | 220,148 |
| 2 | AIYRRGRLYRRN(OH)HV[a] (SEQ ID NO: 18) | 3.46 ± 0.27 | 98.8 ± 17.8 | 35,020 |
| 3 | AIYRRGRLYRRDHV[a] (SEQ ID NO: 19) | 0.454 ± 0.02 | 629.7 ± 19.5 | 721 |
| 4 | AIYRRGRLYRRNSL[b] (SEQ ID NO: 20) | 4.56 ± 0.24 | 42.5 ± 8.83 | 107,294 |
| 5 | AIYRRGRLYRRN(OH)SL[b] (SEQ ID NO: 21) | 0.942 ± 0.082 | 119.9 ± 19.2 | 7,857 |
| 6 | AIYRRGRLYRRDSL[b] (SEQ ID NO: 22) | 0.581 ± 0.09 | 2069 ± 407 | 281 |

[a]Peptides cyclized by butelase-1;

[b]Peptides cyclized by VyPAL2. The cyclization reactions were performed at 37° C. in PBS at pH 6.5 with various concentrations of substrates. The cyclization rates were calculated by comparing the RP-HPLC peak areas of products and starting materials.

Figure 7:
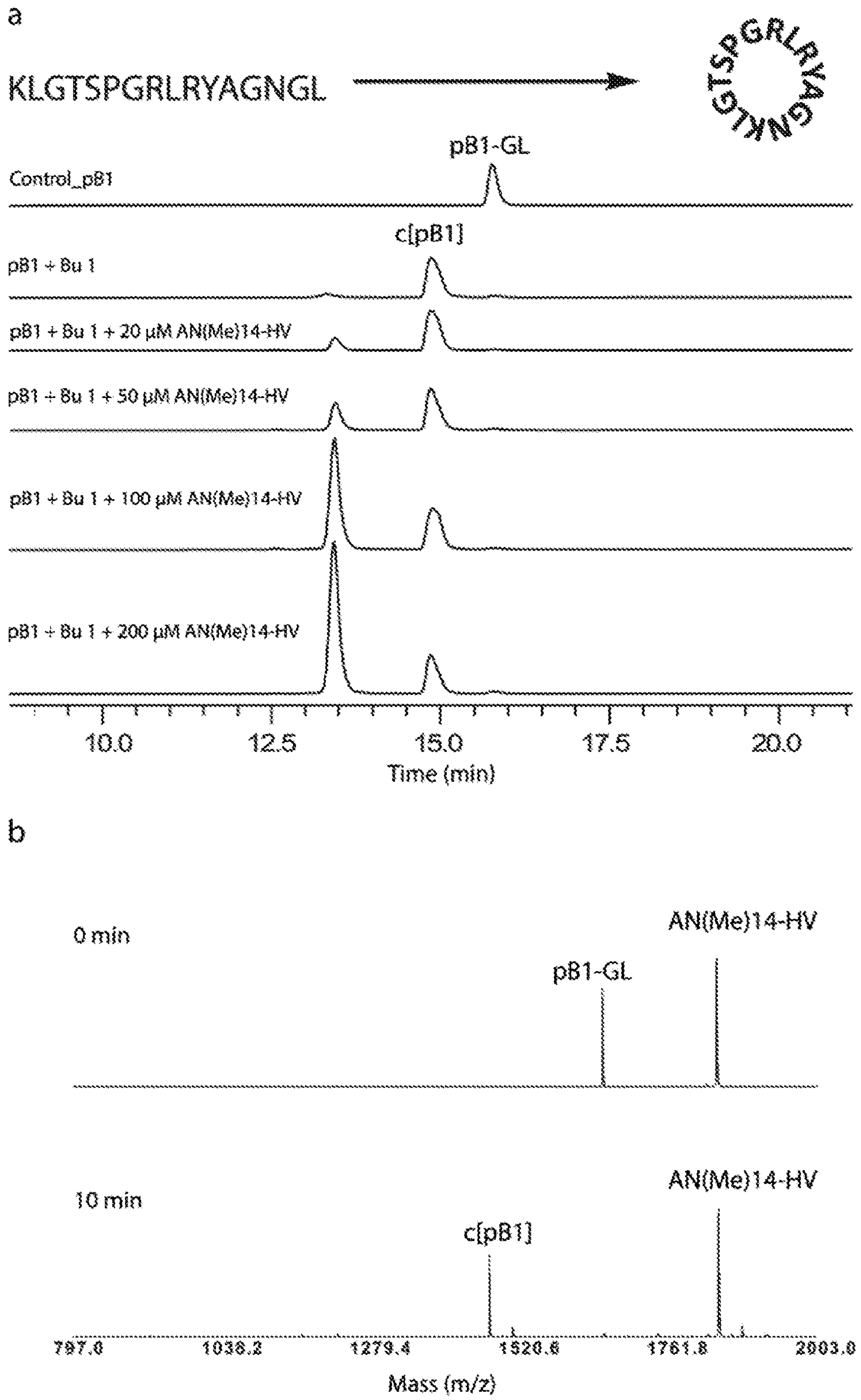
FIG. 7. Inhibitory activity assay of AN(Me)12-HV 7. (a) RP-HPLC trace for cyclization of pB1 peptide (KLGTSPGRLRYAGNGL; SEQ ID NO:13). The cyclization reaction was performed at 37° C. in the present of 200 μM of peptide substrates and 0.001 eq of butelase-1 in 20 mM PBS (pH 6.5) for 10 min. The reactions were monitored by RP-HPLC. The cyclic peptide is labelled as c[pB1] and starred HPLC peak is the potentially inhibitory peptide AN(Me)12-HV 7. Results show that, an increase of the concentration of AN(Me)12-HV 7 didn't affect the cyclization rate of pB1. (b) MALDI profiles of pB1 and AN(Me) 12-HV 7 before and after treatment with butelase-1.
Figure 8:
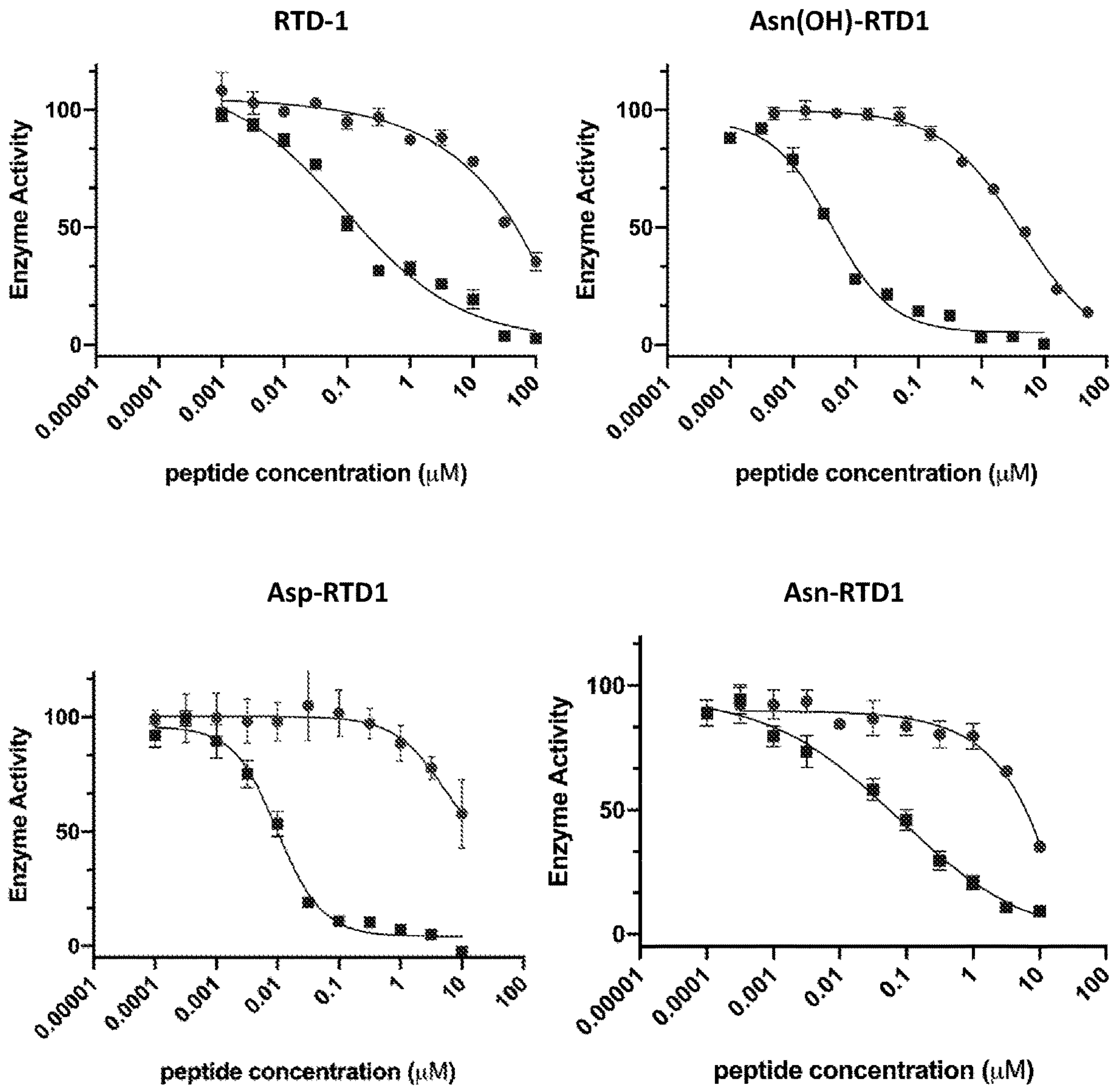
FIG. 8. Inhibition assay of MMP2 and MMP9. Inhibitory activity of RTD1, Asn(OH)-RTD1, Asp-RTD1 and Asn-RTD1 towards MMP2 (square) and MMP9 (round dot). All values are mean±SEM from triplicated measurements.
Figure 9:
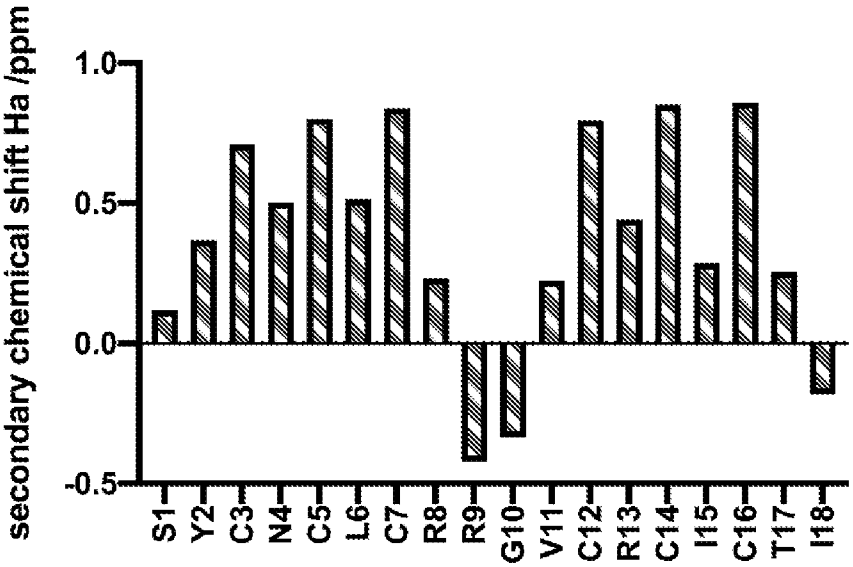
FIG. 9. Secondary chemical shifts of $H_\alpha$. The secondary chemical shift of Asn(OH)-RTD1 shows high similarity with the original RTD1. Using the Hα chemical shifts of random coil as reference, $C^3$-$C^7$ and $C^{12}$-$C^{16}$ regions of Asn(OH)-RTD1 17 seem to have a well-defined β-sheet structure and are joined by 2 loops.

The reason that the P1-Asn(OH) peptides have much better reaction kinetics than the P1-Asp peptides is likely due to the carboxyl group of P1-Asp being deprotonated (as $\gamma COO^-$) at the reaction pH (e.g., pH 6.5, the optimal pH for butelase-1 ligation), which would generate electrostatic repulsion with the negative charged carboxylate of a key Asp residue in the S1 pocket of the ligase (Zauner et al. *J. Biol. Chem.,* 2018, 293, 8934-8946; James et al. *PlantJ,* 2019, 98, 988-999), resulting in weakened binding. Therefore, the higher pKa of the N—OH in Asn(OH) prevents its deprotonation and preserves its H-bonding ability at near neutral pH. Asn(Me), which has an N-methyl group substitution on the side-chain amide, has also been introduced at the P1 position (Table S1). The N-methyl substitution in Asn(Me) removes a H-bond donor and may also hinder the ability of the remaining H on the amide nitrogen to act as an effective H-bond donor for binding to the enzyme's S1 pocket. Results show that the P1-Asn(Me) peptide 7 was not recognized by butelase-1 as it was not a substrate for cyclization nor did it inhibit the cyclization of a known peptide (FIG. 7). It was concluded that, for Asn(OH), the hydrogen atom of the $N^\gamma$-hydroxyl group is essential for binding to the enzyme's S1 pocket through H-bonding.

Figure 2:
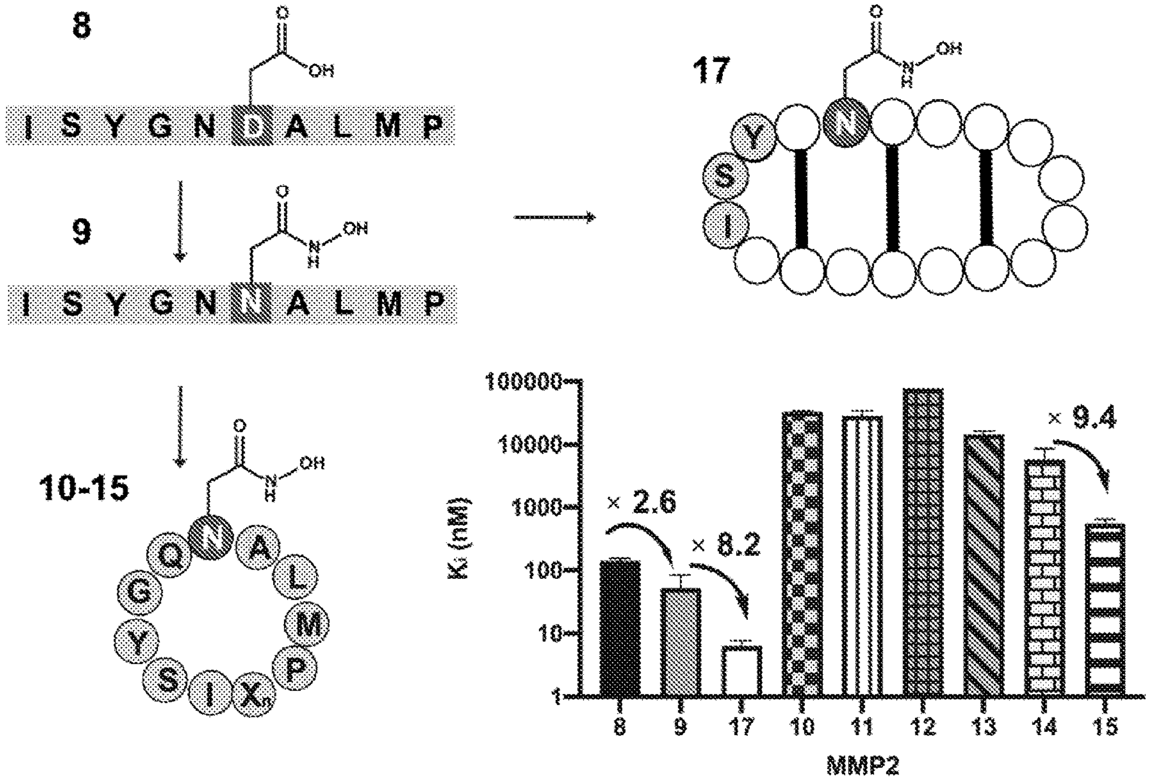
FIG. 2. APP-IP-derived peptides (light grey residues) as inhibitors of MMP2. The key Asp and Asn(OH) residues are colored as dark grey. The peptide 17 shows a single digit $K_i$ (2.8 nM) towards MMP2. Sequences are set forth in SEQ ID NO:5 and 23.

The sidechain hydroxamic acid functionality of Asn(OH) is known to be a metal ion chelator. A variety of hydroxamic acid-derived inhibitors of metalloenzymes have been designed as pharmacologic agents (Muri et al. *Curr. Med. Chem.,* 2002, 9, 1631-1653). Our method provides a convenient way to prepare hydroxamic acid-displaying cyclic peptides as potential inhibitors of pathogenic metalloenzymes, such as matrix metalloprotease 2 which plays pivotal roles in angiogenesis and cancer invasion (Brooks et al. *Cell,* 1996, 85, 683-693). To demonstrate this application, p-amyloid precursor protein-derived inhibitory peptide (APP-IP) was used (Higashi & Miyazaki *J. Biol. Chem.* 2003, 278, 14020-14028; Hashimoto et al. *J Biol Chem.,* 2011, 286, 33236-33243; Higashi et al. *J Biol Chem.,* 2013, 288, 9066-9076) 8, as the starting point (FIG. 2 and Table 2). APP-IP is a known MMP inhibitor and it is largely selective for MMP2 ($K_i$~60 nM) (Higashi & Miyazaki, supra). The aspartic acid residue in APP-IP is responsible for metal binding. Simple replacement of this Asp by Asn(OH) led to a 2.6-fold improvement of inhibitory activity for the derived peptide 9 (FIG. 2 and Table 2) owing to a stronger chelating ability of the hydroxamic acid group in Asn(OH) than the carboxylate in Asp towards the $Zn^{2+}$ in MMP2. Nevertheless, the linear APP-IP peptide has low proteolytic resistance and short half-life in human serum (Higashi et al., supra). Cyclisation is a useful strategy to improve the stability and selectivity of MMP2 inhibitory peptides (Maola et al. *Angew. Chem. Int. Ed.,* 2019, 58, 11801). Head-to-tail cyclisation of APP-IP peptides of varying lengths was performed using the Asn(OH) ligation method (Table 2). However, it was found that the cyclized products, peptides 10-15, had decreased inhibitory activities towards MMP2 likely because simple cyclization locked the peptides into undesirable conformations (Table 2 and FIG. 1).

TABLE 2

IC$_{50}$ and $K_i$ of APP-IP-derived peptides towards MMP2

| No | Peptide sequence | No of AA | IC$_{50}$ (μM) | $K_i$ (μM) |
|---|---|---|---|---|
| 8 | ISYGNDALMP (SEQ ID NO: 5) | 10 | 0.092 | 0.06 |
| 9 | ISYGNN(OH)ALMP (SEQ ID NO: 23) | 10 | 0.035 | 0.023 |
| 10 | cyclo[ISYGQN(OH)ALMP] (SEQ ID NO: 24) | 10 | 32.53 | 21.26 |
| 11 | cyclo[SISYGQN(OH)ALMPG] (SEQ ID NO: 25) | 12 | >100 | >100 |
| 12 | cyclo[SGISYGQN(OH)ALMPSG] (SEQ ID NO: 26) | 14 | 10.68 | 6.98 |
| 13 | cyclo[GSGISYGQN(OH)ALMPSGA] (SEQ ID NO: 27) | 16 | 18.36 | 12.00 |
| 14 | cyclo[ATSGISYGQN(OH)ALMPSGYM] (SEQ ID NO: 28) | 18 | 3.338 | 2.18 |
| 15 | cyclo[ATRSGISYGQN(OH)ALMPSGQYM] (SEQ ID NO: 29) | 20 | 0.354 | 0.231 |

Figure 3:
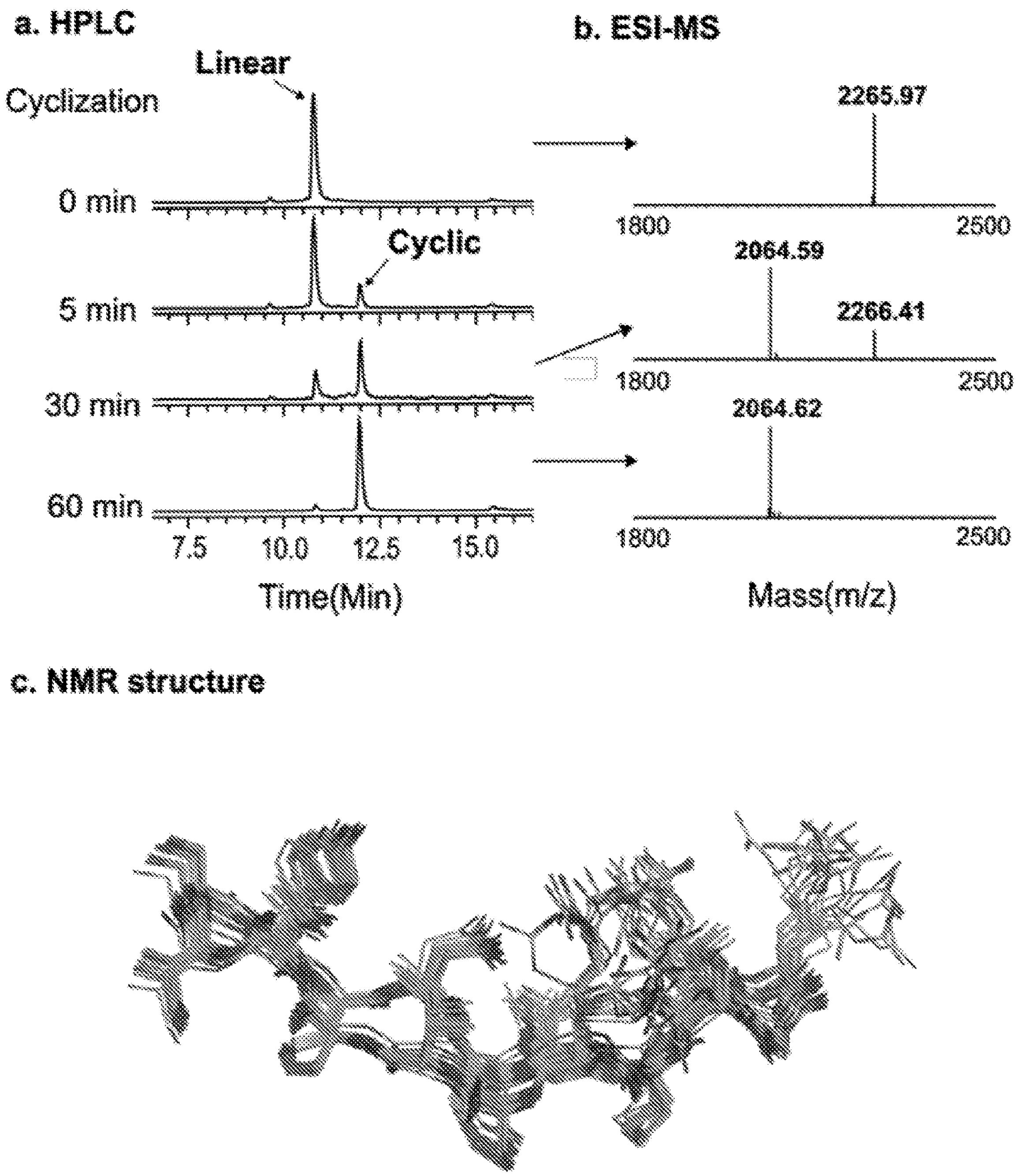
FIG. 3. Synthesis of Asn(OH)-RTD1 17. (a) RP-HPLC trace (15% buffer B to 65% buffer B in 25 mins, 220 nm) and (b) ESI-MS for linear and cyclic Asn(OH)-RTD1. The cyclization reaction was performed at 37° C. using 100 JAM of the linear peptide substrate CLCRRGVCRCICTISYCN(OH)AL (SEQ ID NO:12) (reduced form) and 0.04 eq. of butelase-1 in PBS (pH 6.5). (c) 20 lowest-energy NMR structures of Asn(OH)-RTD1. Asn was used instead of Asn(OH) in structural calculation using Cyana.

Next, the important APP-IP amino acids essential for MMP2 binding were grafted into the highly compact, tetracyclic Cys-ladder structure of rhesus theta defensin-1 (RTD-1) 16 (Table 3; Trabi et al. *Biochemistry,* 2001, 40, 4211-4221). The grafted peptide 17 contained the tripeptide stretch Ile-Ser-Tyr and the key Asn(OH) residue from peptide 9 (FIG. 2 and Table 3). 17 was successfully cyclized at the Asn(OH) residue by incubating the linear substrate with butelase-1 (FIGS. 3*a* and 3*b*). RP-HPLC monitoring indicated that over 60% of the linear peptide was converted to the cyclic product within 30 min and the reaction was completed in 1 h (FIG. 3*a*). ESI-MS showed that the product had a mass loss corresponding to the cleaved dipeptide (Ala-Leu-$NH_2$) after P1-Asn(OH) and formation of a new intramolecular amide bond (FIG. 3*b*). After enzymatic cyclization, 17 was oxidatively folded at pH 8.5 (0.1 M Tris·HCl buffer with 2 M urea) at 4° C. for 8 h. Enzyme inhibition results showed that the folded backbone-cyclic Asn(OH)-RTD1 peptide 17 had a $K_i$ of 2.8 nM towards MMP2 (Table 3 and FIG. 2), a remarkable 8.2-fold improvement over the linear Asn(OH)-APP-IP peptide 9. NMR result shows 17 has the same 3-D structure as RTD-1 (Trabi et al., supra). The Y and N(OH) residues in 17 are constrained in a β-sheet structure and their sidechains are parallelly pointing in the same direction (FIG. 3*c*), similar to what adopted by $Y^3$ and $D^6$ in APP-IP in binding to MMP2 (Hashimoto et al., supra). This pre-organized conformation of the key residues in 17 likely contributed to its improved inhibitory activity over the flexible linear peptide 9. Additionally, Asp-RTD-1 18 was obtained by oxidation of Asn(OH)-RTD-1 17 with $NaIO_4$ (1 eq) (Emery & Neilands *J. Amer. Chem. Soc.,* 1960,82,4903), in 20 mM PBS (pH 7.4) at 0° C., which quickly converted Asn(OH) to Asp in 5-10 min. 17 has a 2.3- and 13-fold better binding affinity than Asp-RTD-1 18 and Asn-RTD-1 19, respectively (Table 3 and FIG. 7). All three peptides are more potent MMP2 inhibitors than the native RTD-1 16.

TABLE 3

Selectivity of RTD1-derived cyclic peptides for MMP-2 over MMP-9.

| No | Peptide sequence | Calc mass (m/z) | Found Mass MH+ (m/z) | $K_i$ (nM) MMP2 | MMP9 |
|---|---|---|---|---|---|
| 16 | cyclo[**GFCRCLCRRGVCRCICTR**] (SEQ ID NO: 30) | 2081.6 | 2082.5 | 60 ± 10.4 | >10000 |
| 17 | cyclo[**SYCN**(OH)**CLCRRGVCRCICTI**] (SEQ ID NO: 31) | 2058.6 | 2059.7 | 2.8 ± 0.47 | 2680 |
| 18 | cyclo[**SYCDCLCRRGVCRCICTI**] (SEQ ID NO: 32) | 2043.5 | 2044.7 | 6.5 ± 1.08 | 3290 |
| 19 | cyclo[**SYCNCLCRRGVCRCICTI**] (SEQ ID NO: 33) | 2042.5 | 2043.6 | 36.5 ± 6.5 | 5588 |

Figure 10:
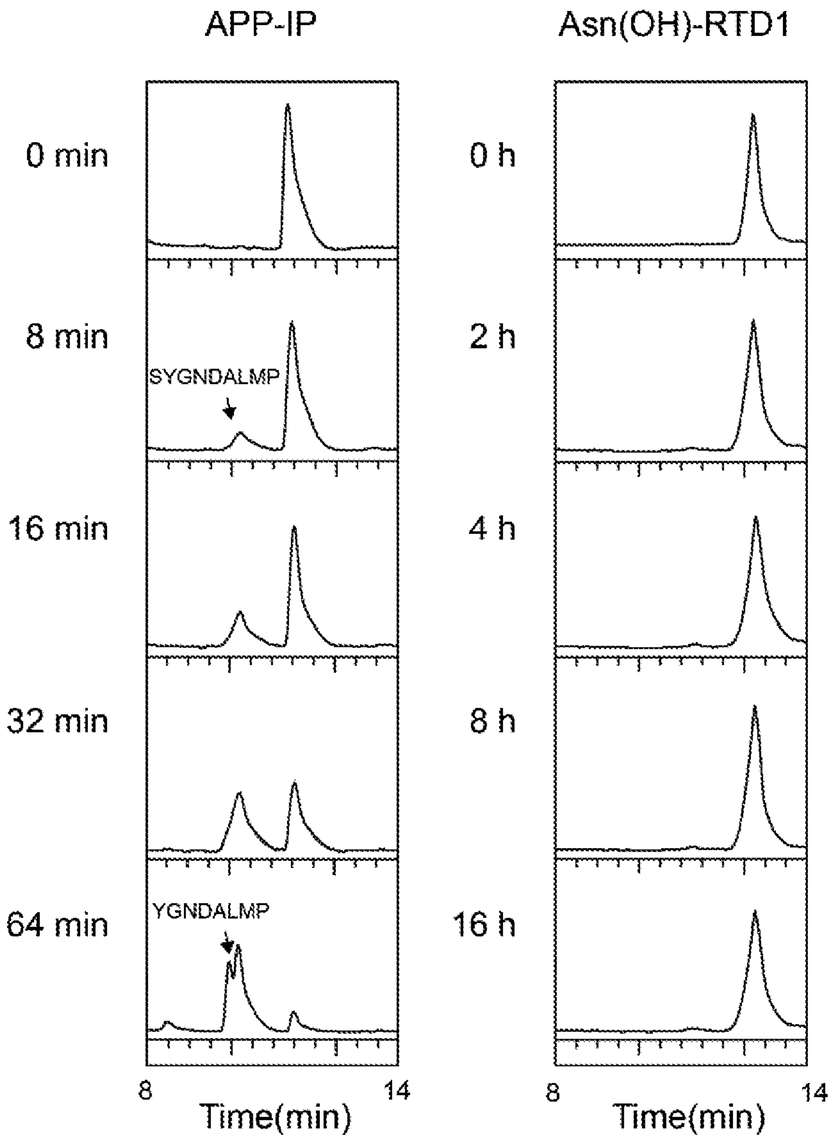
FIG. 10. Stability of linear APP-IP 8 and cyclic Asn(OH)-RTD1 17. Both peptides were incubated in human serum at 37° C. for different time courses, and the remaining peptide were determined by RP-HPLC and ESI-MS. The cyclic Asp-RTD1 co-eluted with other compounds from human serum which eluted out after 15 min, therefore the stability of cyclic Asp-RTD1 cannot be determined quantitatively. Sequences are set forth in SEQ ID Nos. 41 and 42.

Similar to APP-IP, Asn(OH)-RTD1 17 is also a selective inhibitor of MMP2 as it is about 1000-fold more potent towards MMP2 than MMP9 (Table 3), despite the fact that the two enzymes share very similar structures at their active sites. The stability of the linear APP-IP and the cyclic Asn(OH)-RTD1 were examined by incubating the peptides in human serum at 37° C. The cyclic peptide 17 remained intact after 16 h while the linear APP-IP 8 incurred over 50% of degradation in 32 min (FIG. 10). The loss of $N^{\gamma}$-hydroxyl group on Asn(OH) as reported by the Heinis group (Maola et al., supra) was also not observed, which may be stabilized by the highly constrained conformation of 17. The high selectivity and stability of the Asn(OH)-RTD-1 peptide makes it a useful pharmacological tool to study the physiological and pathological roles of MMP2.

Figure 4:
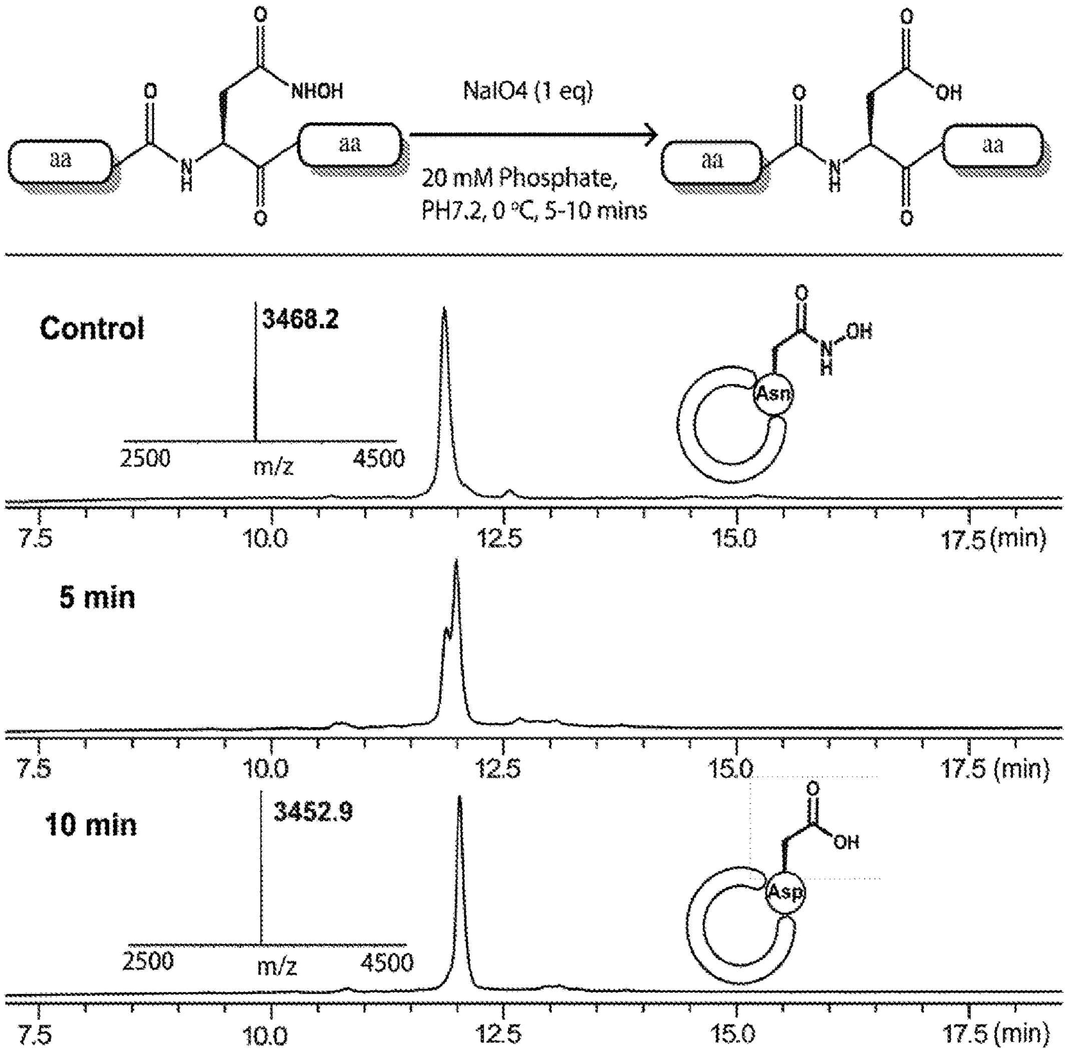
FIG. 4. Converting Asn(OH) to Asp. RP-HPLC trace and ESI-MS profile for the oxidation of cyclic MCoTI-II (200 μM).
Figure 11:
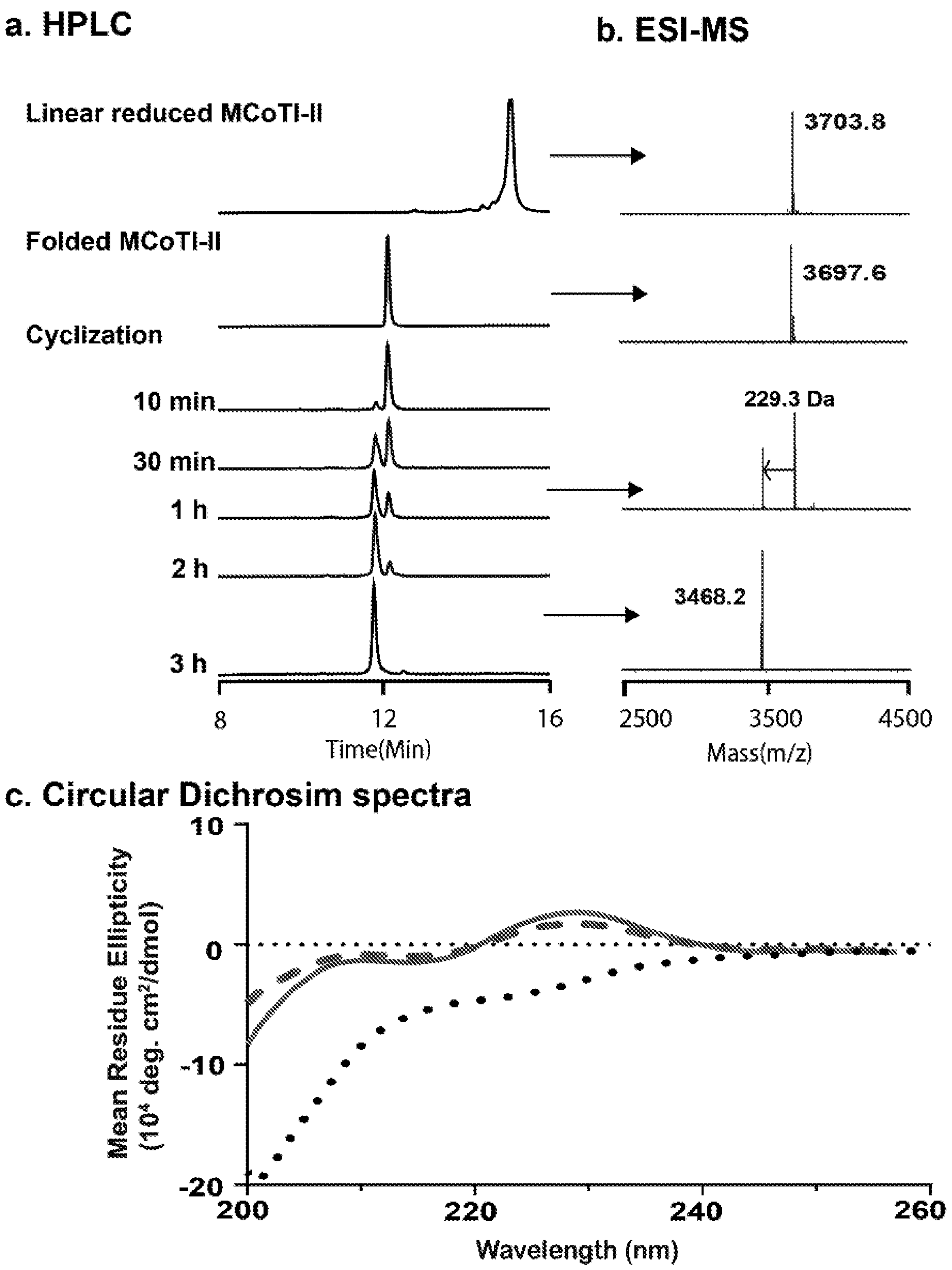
FIG. 11. Butelase-1 mediated cyclization of MCoTI-II 20. (a) RP-HPLC trace (10% buffer B to 50% buffer B in 20 mins, UV absorption at 220 nm) and (b) ESI-MS for linear, refolded acyclic and refolded cyclic MCoTI-II-N(OH)IV. The cyclization reaction was performed at 37° C. using 400 μM of peptide substrate and 0.01 eq of butelase-1 in 20 mM PBS (pH 6.5) for a 3-h time frame. (c) Circular dichroism (CD) spectra of linear reduced MCoTI-II (dotted curve), refolded acyclic MCoTI-II (dashed curve), and cyclic MCoTI-II (solid curve).

Facile conversion of Asn(OH) to Asp makes Asp-cyclization more attainable through PAL ligation, albeit indirectly. To show the generality of this methodology, cyclic peptides ranging from 6 to 34 amino acids from their corresponding P1-Asn(OH) peptide precursors were prepared, followed by oxidative conversion of Asn(OH) to Asp (Table 4). The first peptide generated was MCoTI-II. MCoTI-II is a potent trypsin inhibitor containing 34 amino acid residues with three disulfide bonds and a backbone-cyclic topology, and was first identified from the seeds of *Momordica cochinchinensis* (Hernandez et al. *Biochemistry,* 2000, 39, 5722-5730; Daly et al. *J. Biol. Chem,* 2013, 288, 36141-36148). Chemical and chemoenzymatic methods were developed to cyclize synthetic linear MCoTI by (1) chemical ligation (Daly et al., supra; Thongyoo et al. *Chem. Commun.,* 2006, 27, 2848-2850; Thongyoo et al. *Org. Biomol. Chem.,* 2008, 6, 1462-1470) (2) intein (Camarero et al. Chembiochem, 2007, 8, 1363-1366) (3) sortase A (Stanger et al. *FEBS Lett.,* 2014, 588, 4487-4496) and (4) MCoAEP2 (Du et al. *Nat. Commun.,* 2020, 11, 1575). Herein, it was shown that the use of P1-Asn(OH) makes cyclo-MCoTI-II amenable by PALs that do not prefer P1-Asp substrates (butelase-1 in this study). Linear MCoTI-II-N(OH)IV 20 was prepared by SPPS and oxidatively folded. Backbone cyclization of folded MCoTI-II was completed after incubation with butelase-1 (0.01 eq) for 3 h at 37° C. (FIGS. 11*a&b*). After enzymatic cyclization, the unnatural Asn(OH) residue was then converted to natural Asp (FIG. 4). Again, $NaIO_4$ (1 eq) (Emery & Neilands, supra) was used to oxidize Asn(OH) to Asp under mild conditions. The reaction was done in 20 mM PBS (pH 7.4) at 0° C. and was >95% completed in 10 min. To study the folding states, CD spectra for the linear MCOTI-II, acyclic MCoTI-II (folded), and cyclic MCoTI-II (folded) were measured (FIG. 11*c*). The spectrum of linear MCoTI-II has a negative value from 200 nm to 240 nm, and near-zero value above 240 nm which indicates a random coil structure. In contrast, the spectra of acyclic and cyclic MCoTI-II (both folded) have distinct positive peaks at 230 nm, which are comparable to the reported CD spectrum of synthetic MCoTI-II prepared by D'Souza et al. (D'Souza et al., *Biochemistry,* 2016, 55, 396-405) This result indicates their correct disulfide bond connectivity as natural MCoTI-II (Hider et al. *Biophysical Chemistry,* 1988, 31, 45-51).

Figure 12:
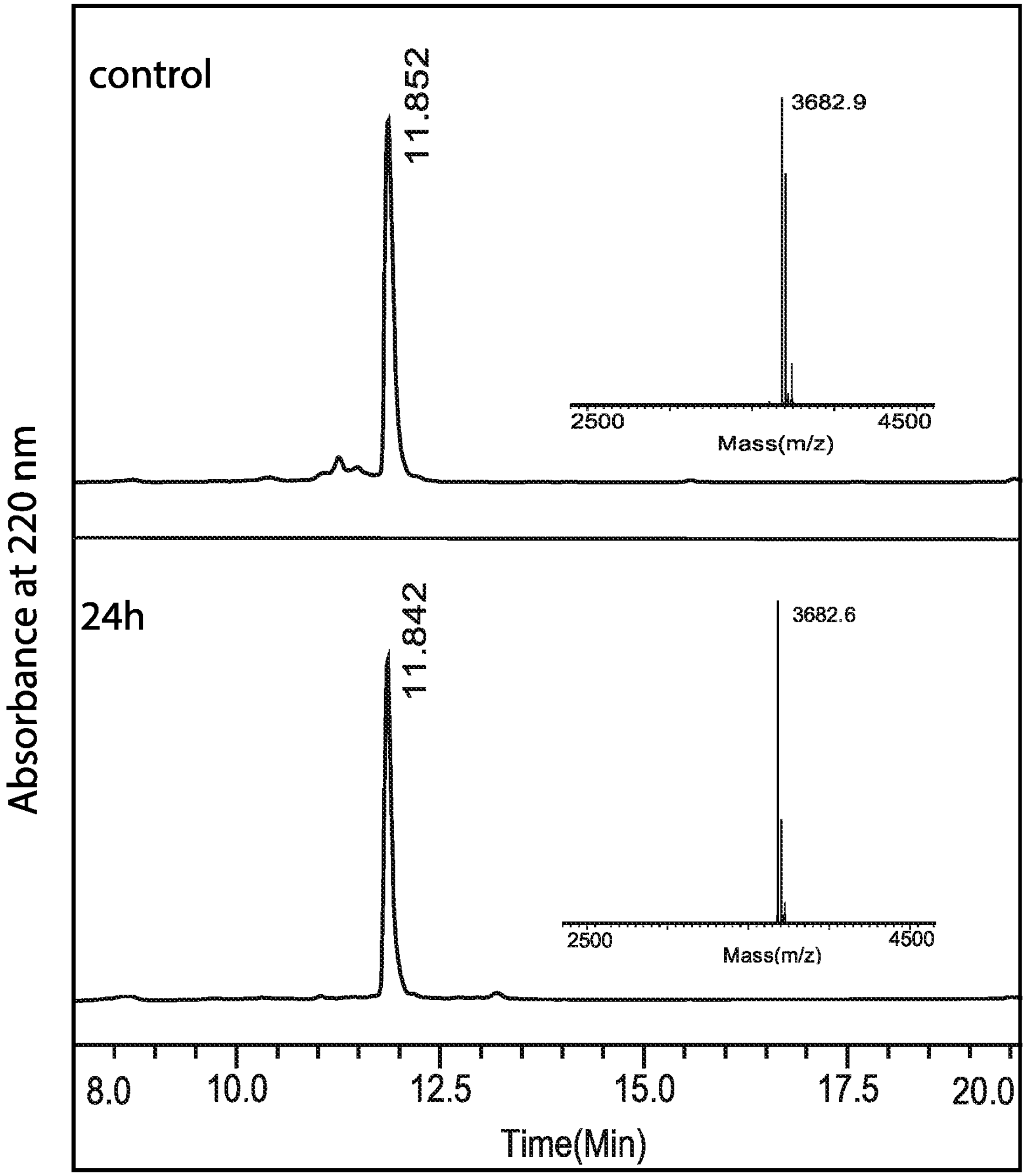
FIG. 12. Butelase-1 mediated cyclization of MCoTI-II-DIV 21. HPLC trace (10% buffer B to 50% buffer B in 20 mins, UV absorption at 220 nm) of MCoTI-II-DIV 21 cyclization over 24 h. The cyclization reaction was performed in the presence of 400 μM of the peptide substrate and 0.01 eq of butelase-1 in 20 mM PBS (pH 6.5). There was no cyclic product observed.
Figure 13:
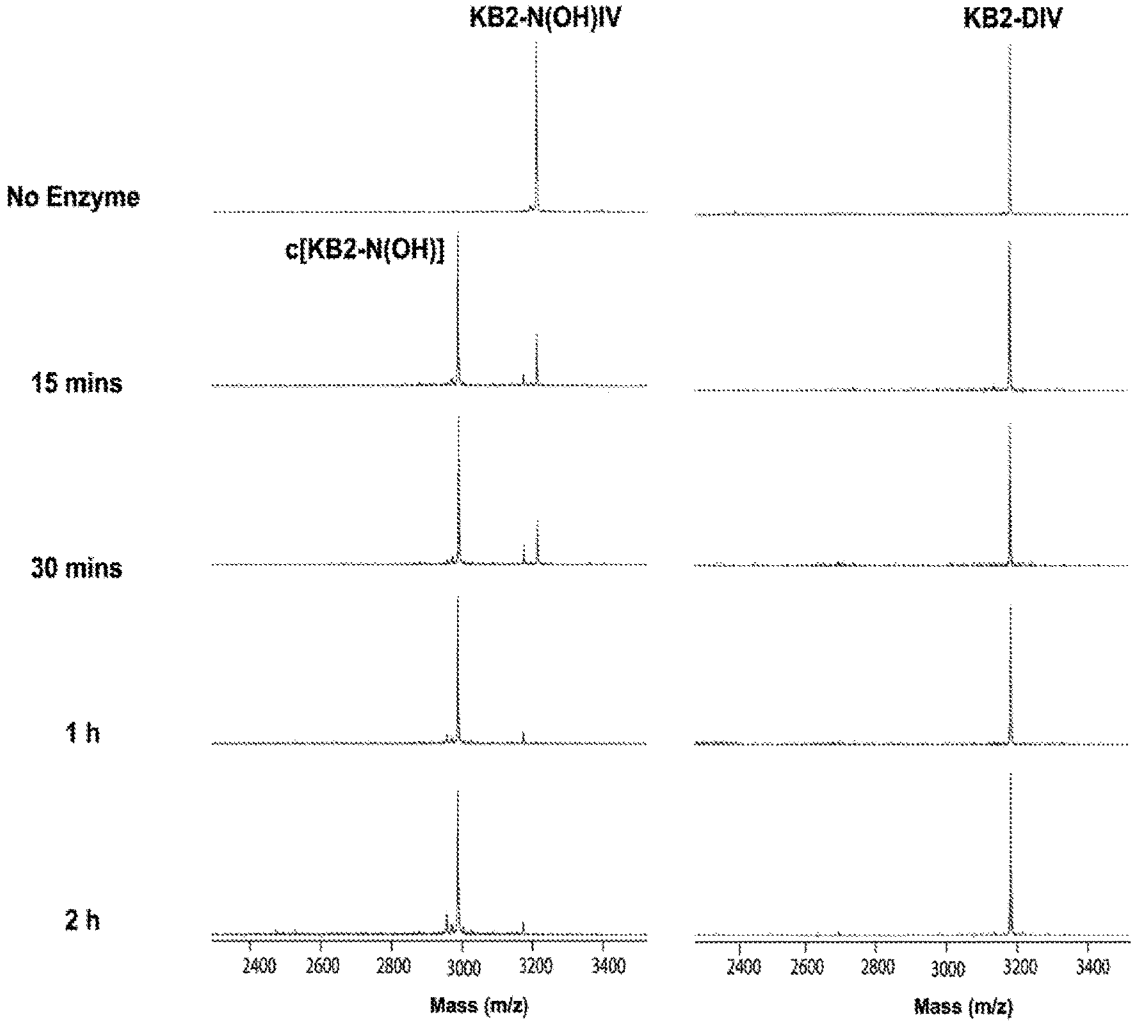
FIG. 13. Butelase-1 mediated cyclization of kB2-N(OH) IV 22 and kB2-DIV 23. The cyclization reactions were performed at 37° C. using 400 μM of the peptide substrates and 0.01 eq of butelase-1 in 20 mM PBS (pH 6.5). The reactions were monitored by MALDI-TOF MS, and the cyclic peptide is labelled as c[KB2-N(OH)].
Figure 14:
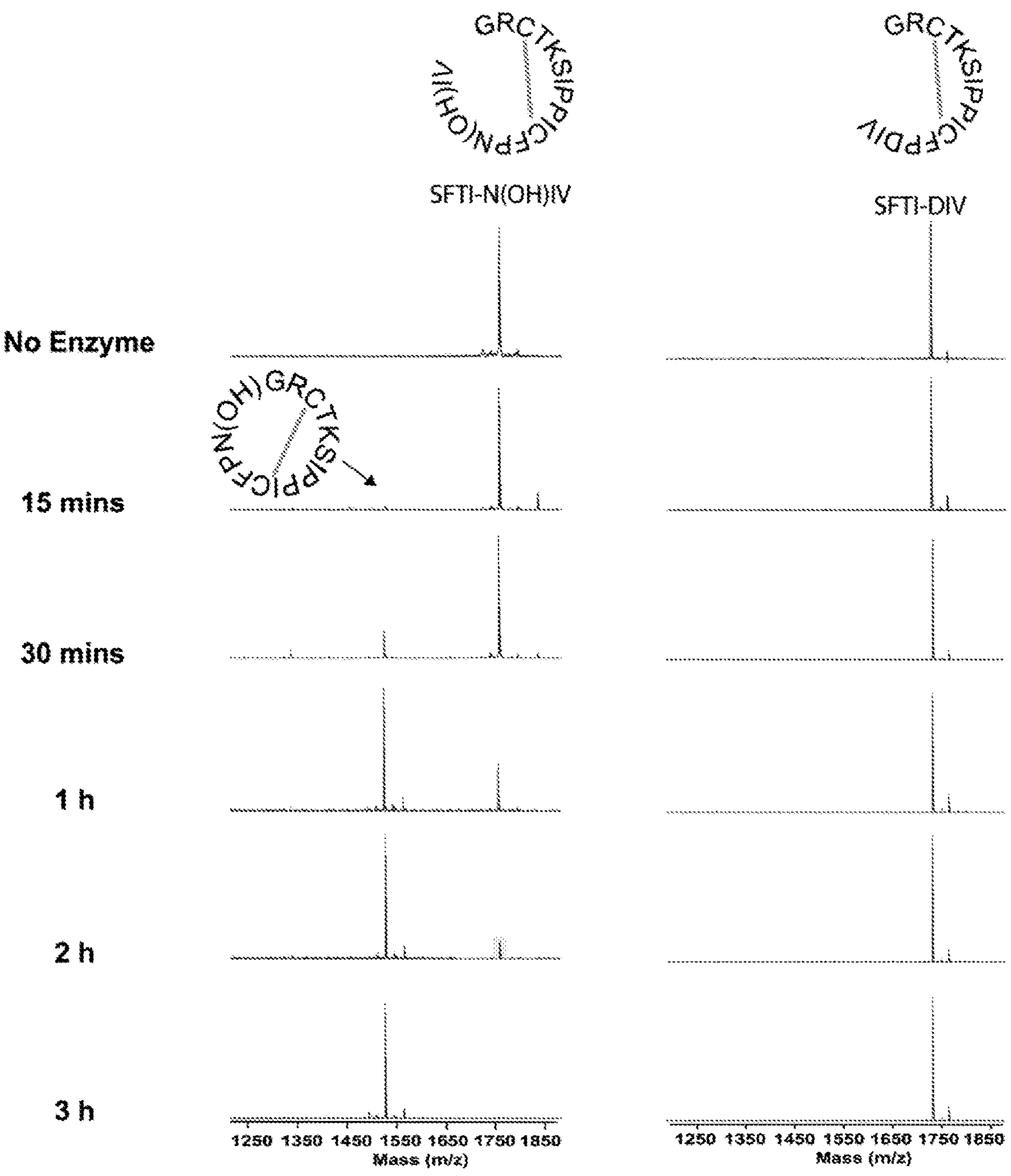
FIG. 14. Butelase-1 mediated cyclization of SFTI-N(OH) IV 24 and SFTI-DIV 25. The cyclization reactions were performed at 37° C. using 400 μM of the peptide substrates and 0.01 eq of butelase-1 in 20 mM PBS (pH 6.5). The reactions were monitored by MALDI-TOF MS. Sequences are set forth in SEQ ID Nos. 9 and 36.

From Table 4, butelase-1 cyclized P1-Asn(OH) peptides (MCoTI-II 20, kB2 22 (Gran et al., *J. Ethnopharmacol,* 2000, 70, 197-203) and SFIT 24 (Luckett et al. *J. Mol. Biol.* 1999, 290, 525-533) within 3 h at 37° C. In contrast, butelase-1 was very inefficient in cyclizing P1-Asp peptides directly as the cyclic products remained undetectable after 3 h (FIGS. 12, 13 and 14). This is due to Asp being a poor P1-amino acid and also to that the N-terminal motifs in these peptides (GG-, GLP- and GR-) are unfavourable nucleophilic substrates of butelase-1, which further impaired the cyclization reaction. However, the unfavourability of the nucleophiles was compensated by the higher reactivity of the P1-Asn(OH) substrates.

Figure 15:
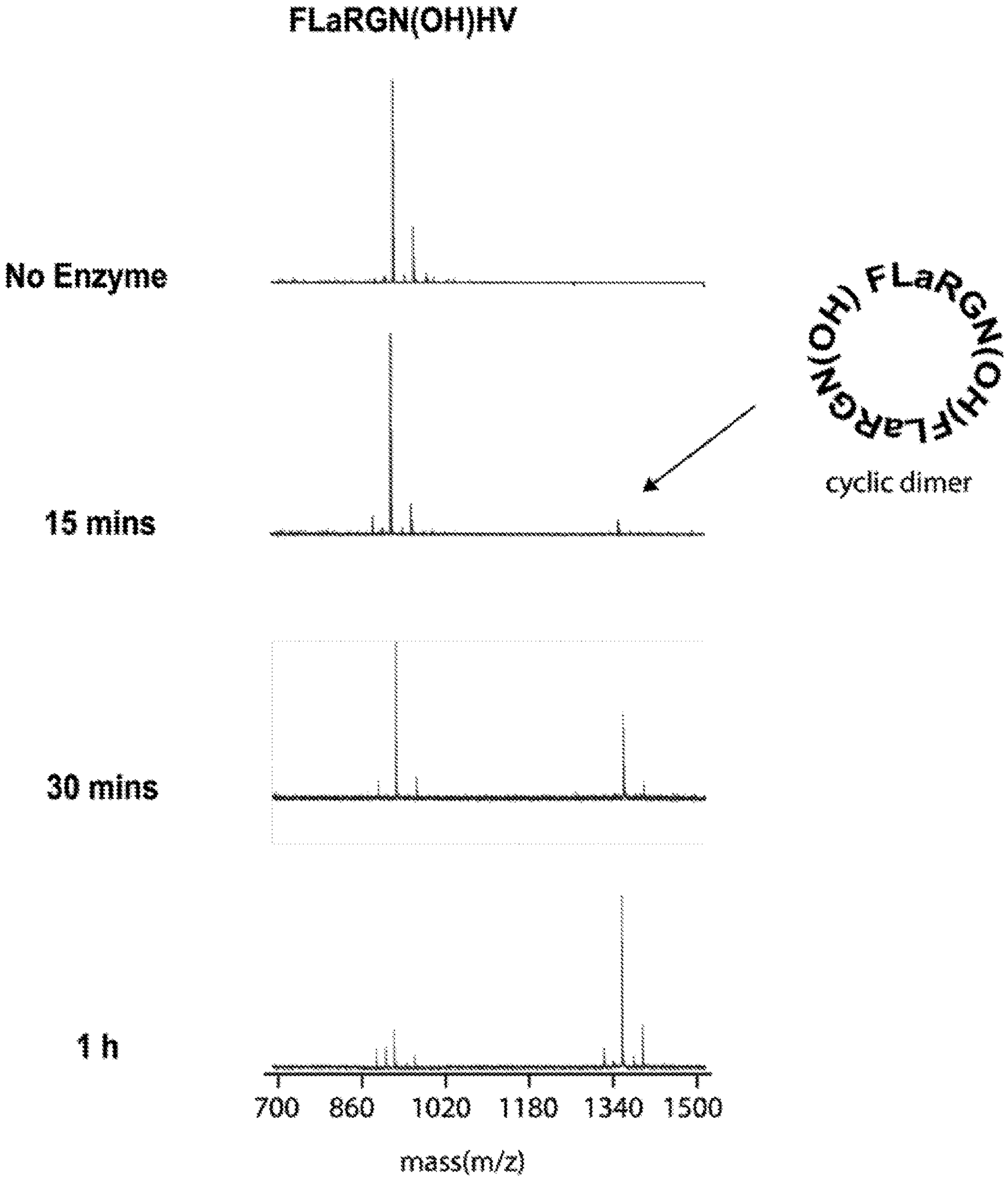
FIG. 15. Butelase-1 mediated cyclization of FLaRGN (OH)HV (SEQ ID NO:14) 26. The cyclization reaction was performed at 37° C. using 400 μM of peptide substrates and 0.01 eq of butelase-1 in 20 mM PBS (pH 6.5). The reactions were monitored by MALDI-TOF MS. A mass corresponds to the cyclic dimer of FLaRGN(OH) (SEQ ID NO:15) was observed. The dimer sequence is set forth in SEQ ID NO:16.
Figure 16:
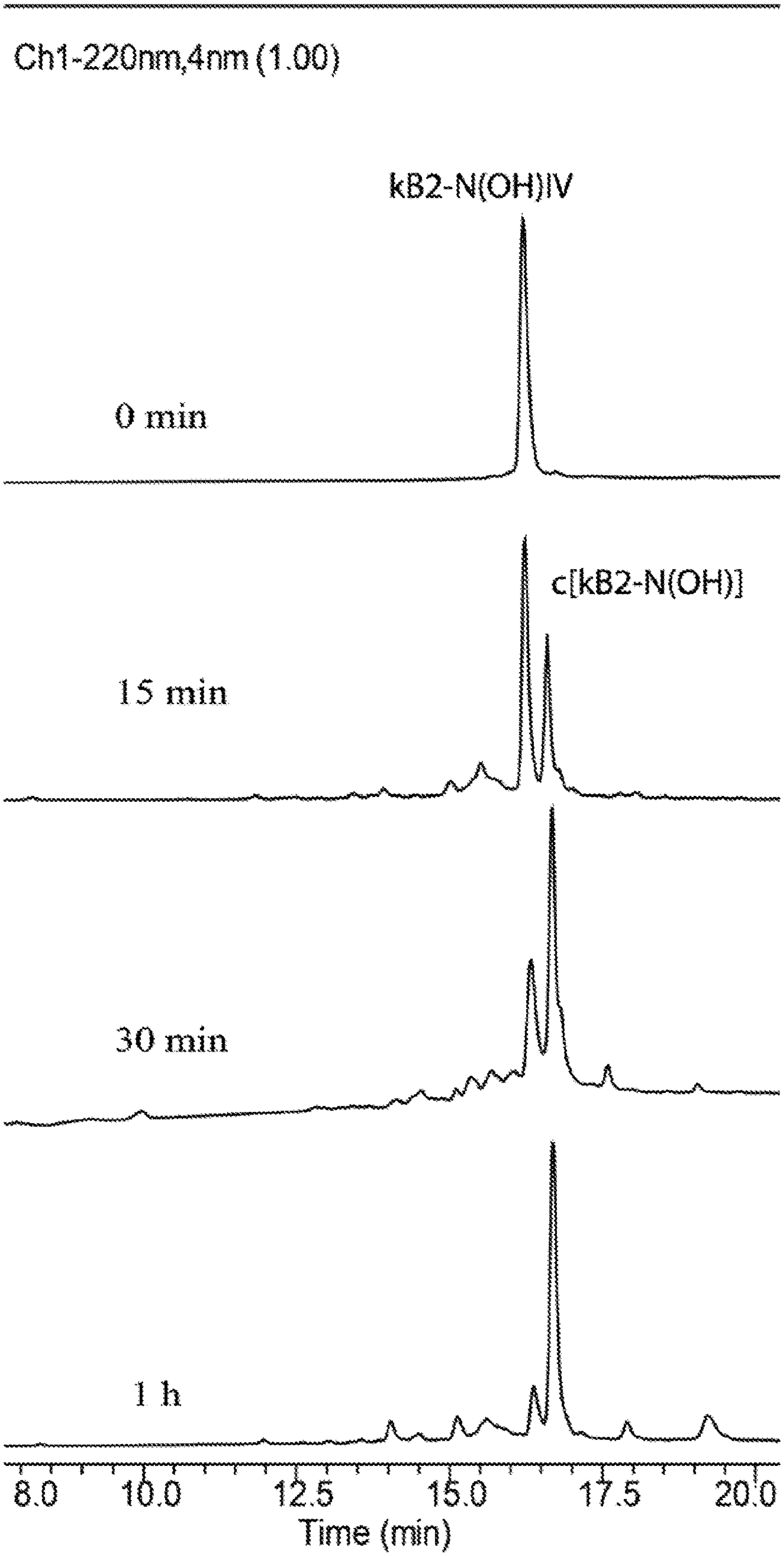
FIG. 16. HPLC trace (20% buffer B to 60% buffer B in 20 mins, 220 nm) of kB2-N(OH)IV 22 cyclization by butelase-1 over 1-h time course. The linear kB2-N(OH)IV and its cyclic product are labeled as kB2-N(OH)IV and c[kB2-N (OH)], respectively. The cyclization reaction was performed at 37° C. using 400 μM of the peptide substrate and 0.01 eq of butelase-1 in 20 mM PBS (pH 6.5).
Figure 17:
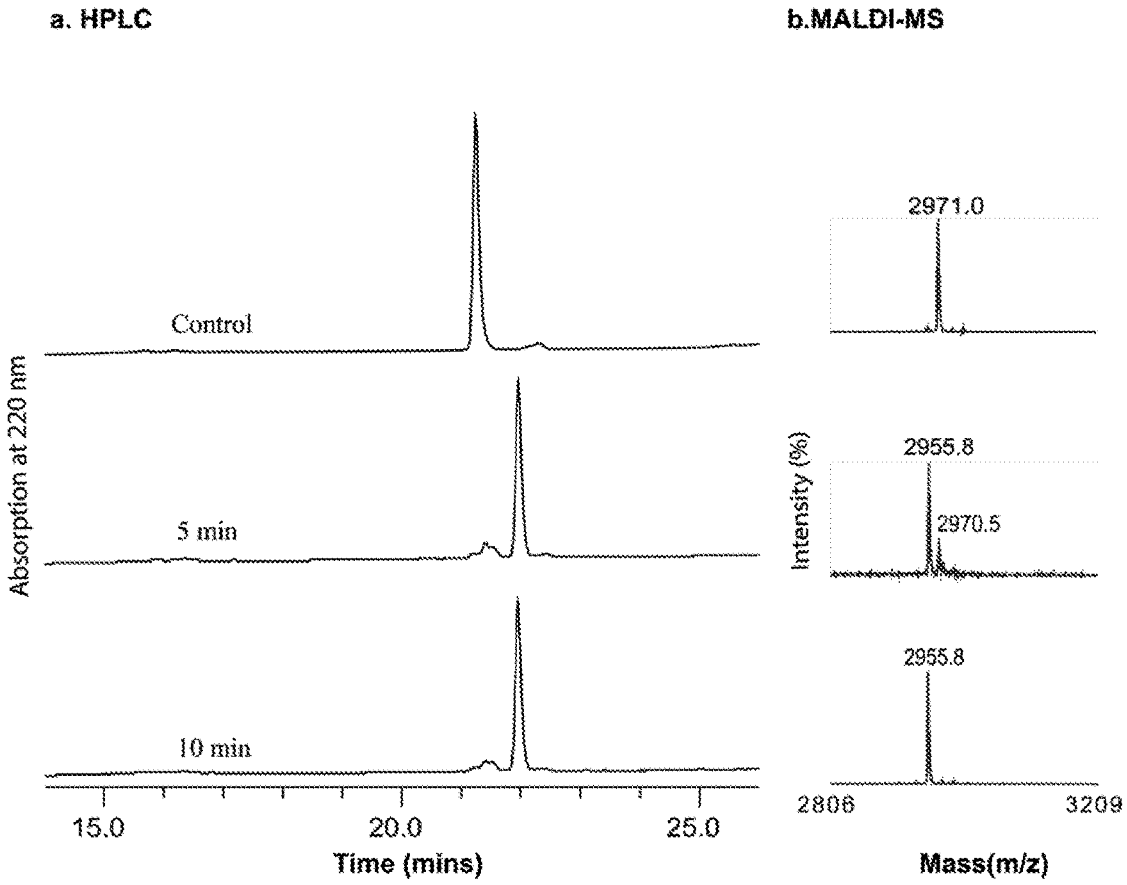
FIG. 17. HPLC (20% buffer B to 80% buffer B in 20 mins, UV absorption at 220 nm) and MALDI-TOF MS monitoring of the hydroxamic acid oxidation reaction of refolded cyclic kB2 22. The oxidation was performed at 0° C. with 200 μM peptide 22, 1 eq $NaIO_4$, 10 eq methionine in 20 mM PBS (pH 7.2) and monitored at 5 min and 10 min.
Figure 18:
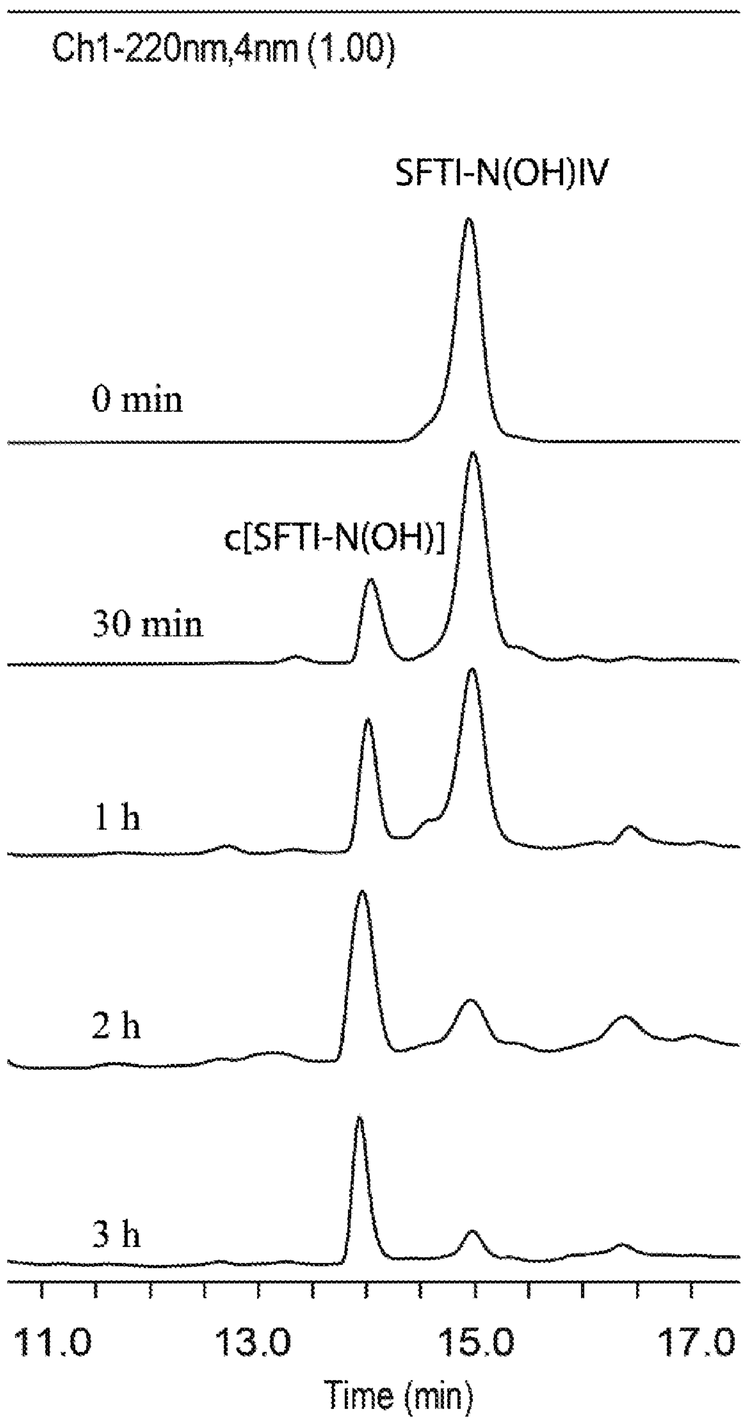
FIG. 18. HPLC trace (20% buffer B to 60% buffer B in 20 mins, UV absorption at 220 nm) of SFTI cyclization over 3 h time course. The linear SFTI-N(OH)IV 24 and its cyclic product are labelled as SFTI-N(OH)IV and c[SFTI-N(OH)], respectively. The cyclization reaction was performed at 37° C. using 400 μM of the peptide substrate and 0.01 eq of butelase-1 in 20 mM PBS (pH 6.5).
Figure 19:
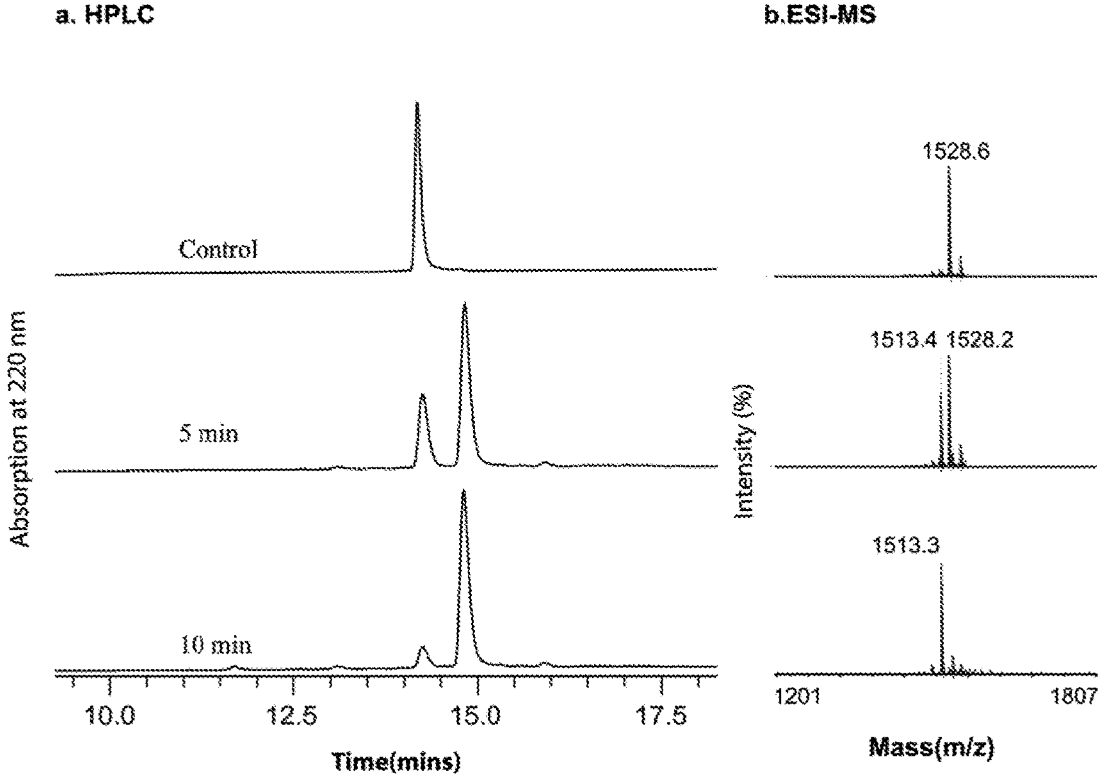
FIG. 19. HPLC (20% buffer B to 60% buffer B in 20 mins, UV absorption at 220 nm) and MALDI-TOF MS monitoring of the hydroxamic acid oxidation reaction of refolded cyclic SFTI 24. The oxidation reaction was performed at 0° C. with 200 μM peptide, 1 eq $NaIO_4$, 10 eq methionine in 20 mM PBS (pH 7.2) and monitored at 5 and 10 min.
Figure 20:
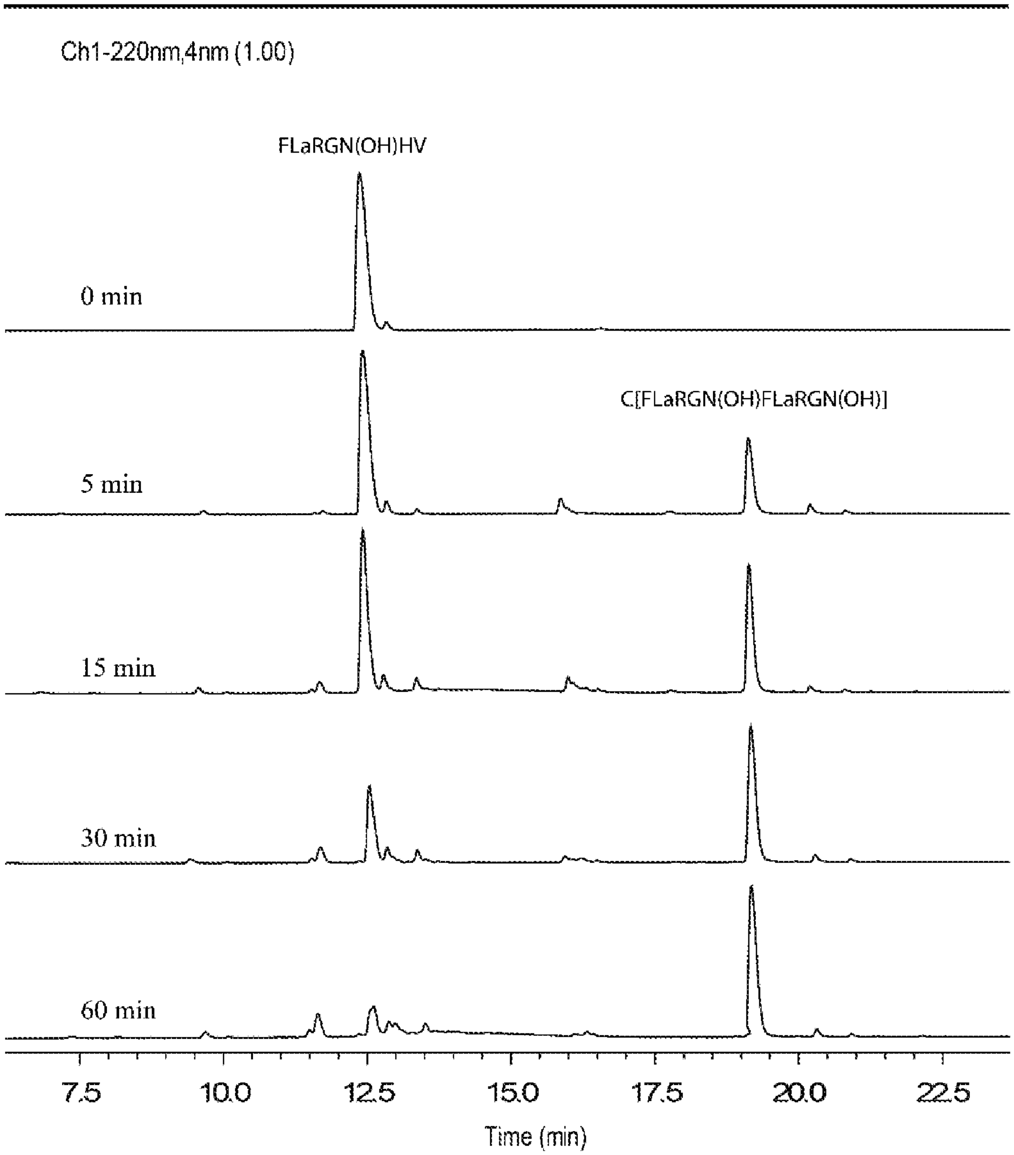
FIG. 20. HPLC trace (10% buffer B to 60% buffer B in 25 mins, UV absorption at 220 nm) of FLaRGN(OH)HV (SEQ ID NO:14) 26 cyclization over 1-h time course. The linear FLaRGN(OH)HV 26 and its cyclic product are labelled as FLaRGN(OH)HV and c[FLaRGN(OH)FLaRGN(OH)] (SEQ ID NO:16), respectively. The cyclization reaction was performed at 37° C. using 400 μM of the peptide substrate and 0.01 eq of butelase-1 in 20 mM PBS (pH 6.5).
Figure 21:
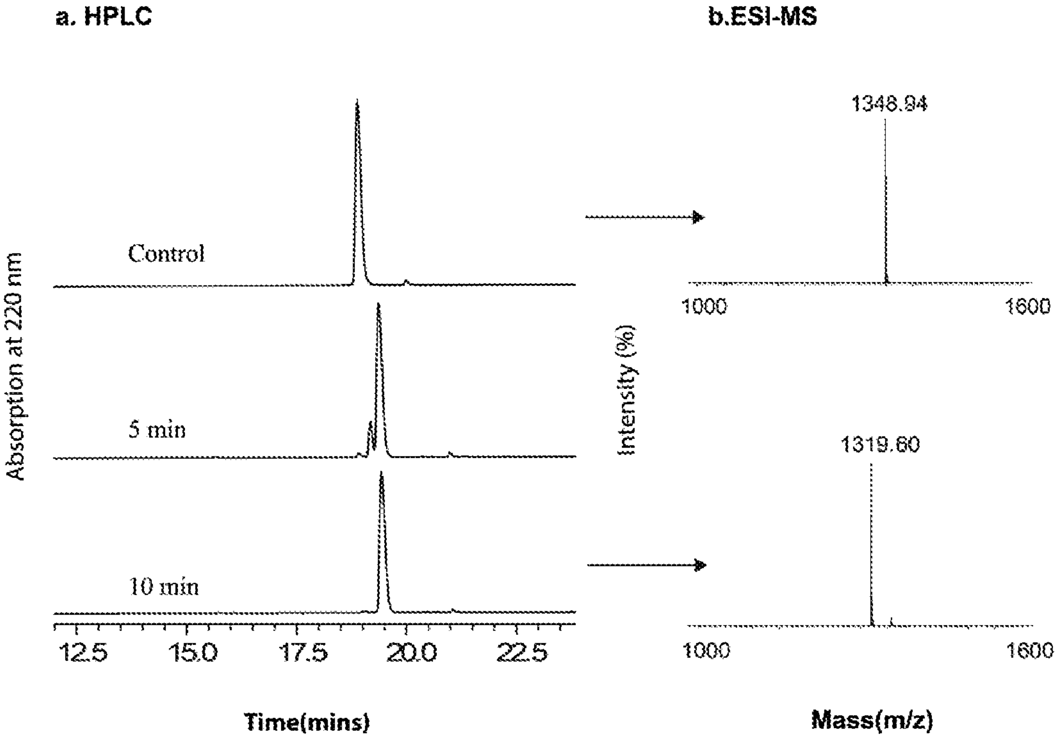
FIG. 21. HPLC (10% buffer B to 60% buffer B in 25 mins, UV absorption at 220 nm) and ESI MS monitoring of the hydroxamic acid oxidation reaction of c[FLaRGN(OH) FLaRGN(OH)] 26 (SEQ ID NO:16). The oxidation was performed at 0° C. with 200 μM peptide, 2 eq $NaIO_4$, 10 eq methionine in 20 mM PBS (pH 7.2) and monitored at 5 min and 10 min.
Figure 22:
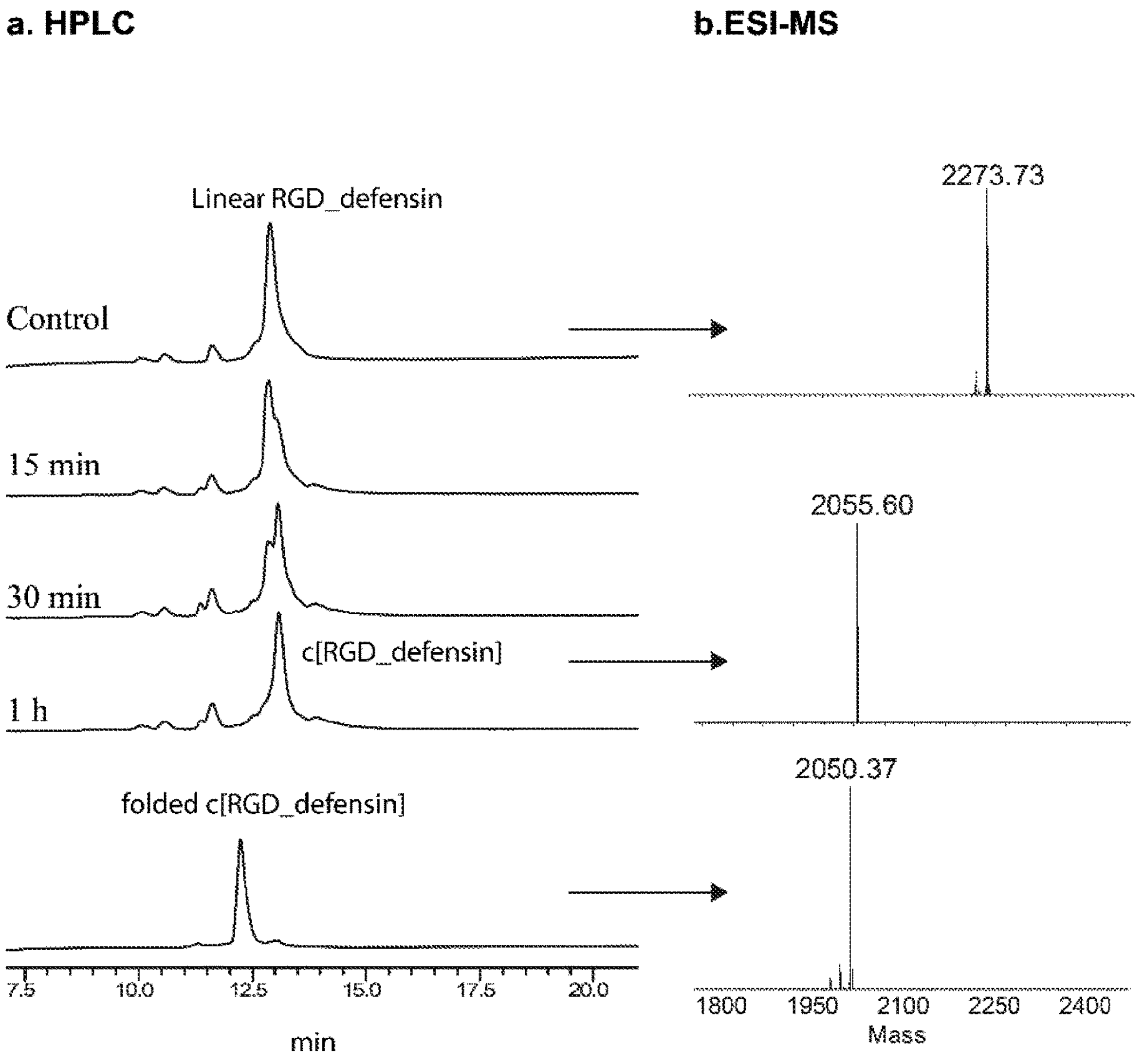
FIG. 22. HPLC trace (10% buffer B to 50% buffer B in 20 mins, 220 nm) and ESI MS profile of RGD-defensin peptide 27 cyclization over 1 h time course. The linear RGD defensin and its cyclic product are labelled as linear RGD defensin and c[RGD defensin], respectively. The cyclization reaction was performed at 37° C. using 400 μM of the peptide substrate and 0.01 eq of butelase-1 in 20 mM PBS (pH 6.5).
Figure 23:
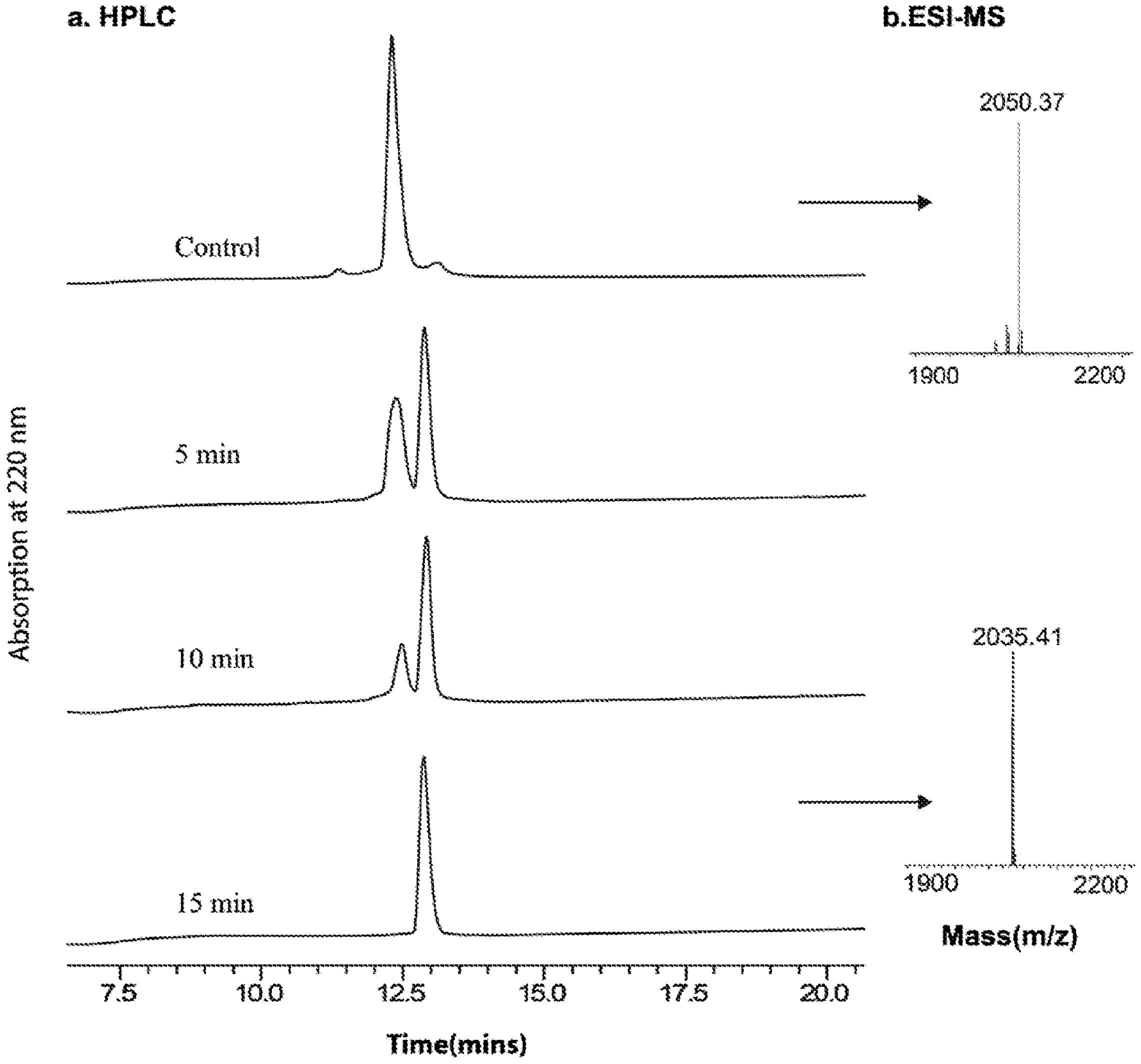
FIG. 23. HPLC (10% buffer B to 50% buffer B in 20 mins, UV absorption at 220 nm) and MALDI-TOF MS monitoring of the hydroxamic acid oxidation reaction of refolded cyclic RGD defensin 27. The oxidation was performed at 0° C. with 200 μM peptide, 1 eq $NaIO_4$, 10 eq methionine in 20 mM PBS (pH 7.2) and monitored at 5 min, 10 min and 15 min.

Also prepared were RGD-containing cyclic peptides (for integrin targeting) using the Asp residue as the cyclization site to enhance their metabolic stability and therefore therapeutic value (Conibear et al. *ChembioChem,* 2014, 15, 451-459; Pfaff et al. *J. Biol. Chem.,* 1994, 269, 20233-8). Two such peptides were used for demonstration (Table 4). The theta defensin-RGD precursor 27 was cyclized within 1 h after incubating with VyPAL2 (FIG. 19). Interestingly, FLaRGN(OH)HV 26 was converted to a cyclic dimer within 1 h (FIGS. 15 and 20), likely because the high angle strain prevented the formation of the small 6-residue ring, which have previously been reported by Hemu (Hemu et al. *Org. Lett.,* 2019. 21. 202902032). The peptide first underwent intermolecular ligation, followed immediately by cyclization, to form cyclo-[FLaRGN(OH)FLaRGN(OH)].

TABLE 4

Peptides cyclized at Asp using Asn(OH)-mediated cyclization followed by oxidative N(OH)-to-D conversion

| Peptide | No | Sequence | Cyclisation time (h) | Yield (%) | Oxidation time (min) | Yield (%) |
|---|---|---|---|---|---|---|
| MCoTI-II-N(OH)IV | 20 | GGVCPKILKKCRRDSDCP GACICRGNGYCGSGS**N(OH)**IV (SEQ ID NO: 34) | 3 | 95 | 10 | >95 |
| MCoTI-II-DIV | 21 | GGVCPKILKKCRRDSDCP GACICRGNGYCGSGS**D**IV (SEQ ID NO: 7) | 3 | ND | NA | NA |
| kB2-N(OH)IV | 22 | GLPVCGETCFGGTCNTP GCSCTWPICTR**N(OH)**IV (SEQ ID NO: 35) | 1 | 80 | 10 | >95 |
| kB2-DIV | 23 | GLPVCGETCFGGTCNTP GCSCTWPICTR**D**IV (SEQ ID NO: 8) | 1 | ND | NA | NA |
| SFTI-N(OH)IV | 24 | GRCTKSIPPICFP**N(OH)**IV (SEQ ID NO: 36) | 3 | 85 | 10 | >95 |
| SFTI-DIV | 25 | GRCTKSIPPICFP**D**IV (SEQ ID NO: 9) | 3 | ND | NA | NA |
| RGD-N(OH)HV | 26 | FLaRGN(OH)HV (SEQ ID NO: 14) | 1 | 90* | 10 | >95 |
| RGD-defensin-N(OH)SL | 27 | ACRCLCRRGDCRCICRG **N(OH)**SL (SEQ ID NO: 37) | 1 | 95 | 15 | >95 |

Cyclization reactions were performed at 37° C. using 400 μM of peptide substrates and 0.01 eq of butelase-1 or VyPAL2 in PBS (pH 6.5) for 2-3 h. Peptide 27 was cyclized by VyPAL2 while others were cyclized by butelase-1. Asn(OH) oxidation was performed in 20 mM PBS (pH 7.4) at 0° C., with 1 eq or 2 eq of $NaIO_4$.

ND = not detectable.

*Yield of the cyclic dimer.

much higher affinity and turnover than the P1-Asp peptides for peptide cyclization. A wide range of cyclic peptides were prepared to demonstrate our methodology of P1-Asn(OH)-enabled cyclization and oxidative Asn(OH)-to-Asp conversion. The structure and bioactivity of these peptides were confirmed by CD spectroscopy, NMR and enzyme inhibition assays. More importantly, it was shown that cyclization of Asn(OH)-containing peptides are suited for generating inhibitors that have high potency and selectivity towards matrix metalloproteinases 2 (MMP2) as well as high stability in human serum. To sum up, it was shown that Asn(OH) is an excellent mimetic of Asn as the P1 amino acid in PAL substrates. This engineered Asn(OH) serves three functions: (1) it mediates PAL-catalyzed ligation and is the site of peptide cyclization, (2) it donates a chelator for metal ions for metalloenzyme inhibition, and (3) it is a precursor to Asp residue. The results disclosed herein clearly show that substrate engineering is capable of expanding the substrate scope of PALs and increasing the usefulness of the prepared cyclic peptides.

Figure 24:
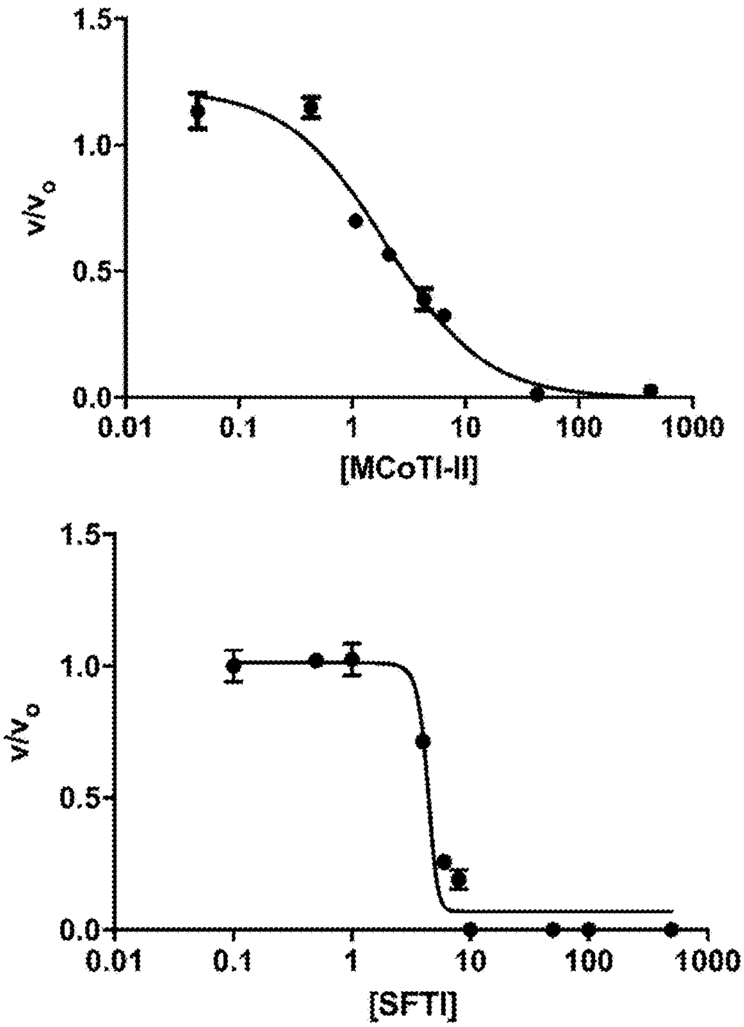
FIG. 24. Trypsin inhibition assay of MCoTI-II 20 and SFTI 24. All triplicated data are presented as means±SEM.
Figure 25:
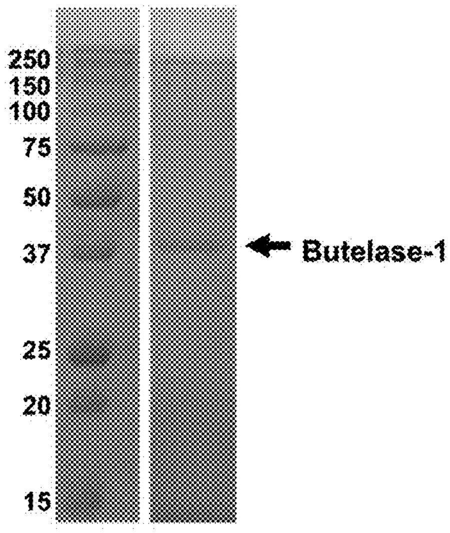
FIG. 25. SDS-PAGE of butelase-1.
Figure 26:
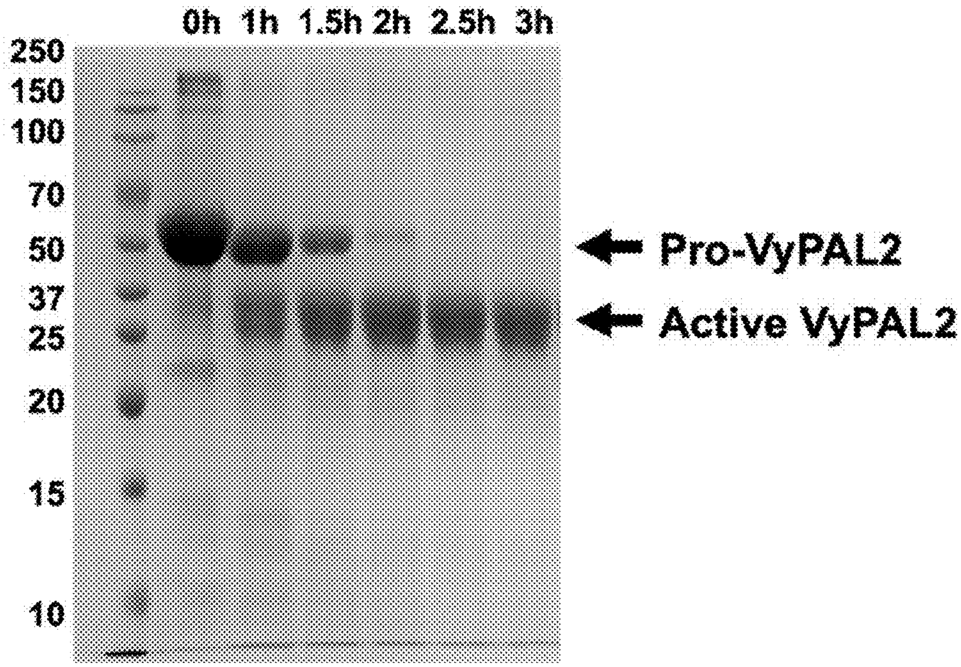
FIG. 26. Activation of pro-VyPAL2. After 2.5-h activation, the activated enzyme was purified by SEC at pH 6.5 and stored at −20° C.

To evaluate whether the synthetic MCoTI-II and SFTI have similar bioactivity as their native counterparts, trypsin inhibition assays were performed (Table S3 and FIG. 24). The $K_i$ of cyclic MCoTI-II towards trypsin was found to be 0.18 nM. The reported $K_i$ value of cyclic MCoTI-II ranges from 0.03 to 2.1 nM, depending on the methods used (Avrutina et al. *J. Biol. Chem.,* 2005, 386, 1301-1306). The $K_i$ of SFTI towards trypsin was 0.44 nM, which is also consistent to reported values. Therefore, both cyclic trypsin inhibitor peptides prepared by our method have the expected biological activities.

In conclusion, an artificial amino acid, Asn(OH), was engineered as the P1 residue in peptide substrates of butelase-1 and VyPAL2. The P1-Asn(OH) peptides exhibit a

TABLE S1

Expected, observed masses and amino acid sequences of peptides synthesized for enzyme kinetic studies.

| Model peptides | Sequence | Expected mass (m/z) | Founded mass [MH+] (m/z) |
|---|---|---|---|
| 1 | AIYRRGRLYRRNHV (SEQ ID NO: 17) | 1830.1 | 1830.9 |
| 2 | AIYRRGRLYRRN(OH)HV (SEQ ID NO: 18) | 1846.1 | 1846.5 |
| 3 | AIYRRGRLYRRDHV (SEQ ID NO: 19) | 1831.1 | 1831.3 |
| 4 | AIYRRGRLYRRNSL (SEQ ID NO: 20) | 1794.1 | 1793.9 |
| 5 | AIYRRGRLYRRN(OH)SL (SEQ ID NO: 21) | 1810.1 | 1810.7 |
| 6 | AIYRRGRLYRRDSL (SEQ ID NO: 22) | 1795.1 | 1794.6 |
| 7 | AIYRRGRLYRRN(Me) HV (SEQ ID NO: 38) | 1844.1 | 1844.1 |

TABLE S2

Expected, observed masses and amino acid sequences of peptides derived from APP-IP.

| No | Peptide sequence | Calc mass (m/z) | Found Mass MH+ (m/z) |
|---|---|---|---|
| 8 | ISYGNDALMP (SEQ ID NO: 5) | 1079.2 | 1080.3 |
| 9 | ISYGNN(OH)ALMP (SEQ ID NO: 23) | 1094.2 | 1095.0 |
| 10 | cyclo[ISYGQN(OH)ALMP] (SEQ ID NO: 24) | 1090.5 | 1091.5 |
| 11 | cyclo[SISYGQN(OH)ALMPG] (SEQ ID NO: 25) | 1234.6 | 1235.6 |
| 12 | cyclo[SGISYGQN(OH)ALMPSG] (SEQ ID NO: 26) | 1378.1 | 1379.6 |
| 13 | cyclo[GSGISYGQN(OH)ALMPSGA] (SEQ ID NO: 27) | 1506.9 | 1507.9 |
| 14 | cyclo[ATSGISYGQN(OH)ALMPSGYM] (SEQ ID NO: 28) | 1845.3 | 1846.2 |
| 15 | cyclo[ATRSGISYGQN(OH)ALMPSGQYM] (SEQ ID NO: 29) | 2129.6 | 2030.6 |

TABLE S3

Trypsin inhibitory activity ($IC_{50}$ and $K_i$) of MCoTI-II 20 and SFTI 24. All triplicated data are presented as means ± SEM.

| Inhibitor | Peptide sequence | $IC_{50}$ (nM) | $K_i$ (nM) |
|---|---|---|---|
| [MCoTI-II] | [GGVCPKILKKCRRDSDCPGACICR GNGYCGSGSD] (SEQ ID NO: 39) | 2.01 ± 0.28 | 0.18 ± 0.03 |
| [SFTI] | [GRCTKSIPPICFPD] (SEQ ID NO: 40) | 4.85 ± 0.23 | 0.44 ± 0.02 |

TABLE S4

| Structural statistics for ASN(OH)-RTD1 17. | |
|---|---|
| Distance restraints | |
| Intraresidue (i − j = 0) | 44 |
| Sequential (\|i − j\| = 1) | 52 |
| Medium-range (2 ≤ \|i − j\| ≤ 4) | 32 |
| long-range (\|i − j\| ≥ 5) | 10 |
| Total NOE constraints | 138 |
| Angular restraints | |
| φ | 15 |
| ψ | 15 |
| Distance restraints violations | |
| No. of violations | 22 |
| Average NOE violation (Å) | <0.31 |
| Maximum NOE violation (Å) | <0.48 |
| Average target function values | 4.74 (4.65-4.92) |
| Deviation from mean structure | |
| Backbone atoms (N, Cα, C') (Å) | 0.22 ± 0.09 |
| Heavy atoms (Å) | 0.94 ± 0.18 |
| Ramachandran plot analysis | |
| Residues in the most favorable region (%) | 53.3 |
| Residues additionally allowed region (%) | 46.7 |
| Residues in the generously allowed region (%) | 0 |
| Residues in the disallowed region (%) | 0 |

Example 2

Peptides including $N^{\gamma}$-amino-L-asparagine can be synthesized by using the standard Fmoc solid phase peptide synthesis (Fmoc SPPS) protocol (Scheme 1 below). The $N^{\gamma}$-amino group on Asn($NH_2$) is introduced on-resin by reacting the side-chain carboxyl of an Asp residue with hydrazine ($NH_2NH_2$) in the presence of a coupling reagent such as PyBOP. To generate a sidechain selectively-deprotected Asp residue in a resin-bound peptide, Fmoc-Asp (ODmab)-OH is used to introduce the orthogonally protected Asp residue at the required position and after assembling the entire peptide sequence with the N-terminal amine protected as Boc or capped (e.g., by acetyl), the ODmab group is removed by treatment with 5% hydrazine in DMF (5 min×3). The exposed carboxyl of the Asp residue is then coupled with $NH_2NH_2$ (10 eq) using PyBOP (1.2 eq) in DMF (with 1.2 eq DIEA) for 3 h. To ensure a complete reaction, the coupling can be repeated for two more times. Because aspartimide formation is prone to occur, the aspartyl amide bond also needs to be protected such as in (Dmb)Gly (Scheme 1). The peptide is then cleaved from resin using a trifluoroacetic acid (TFA) cocktail according to the standard cleavage procedure.

Scheme 1. Synthesis of Asn(NH2)-containing peptides by Fmoc SPPS.

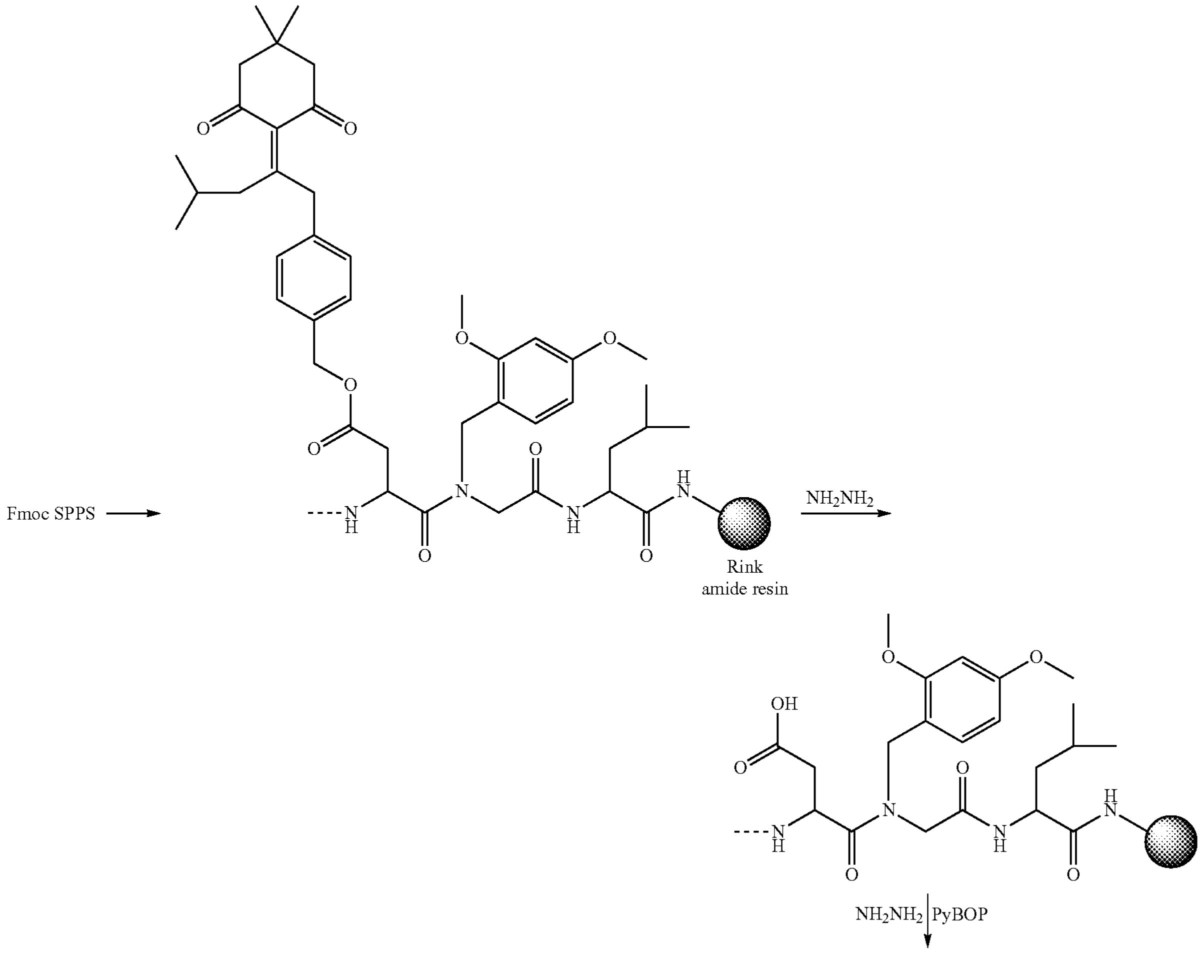

-continued

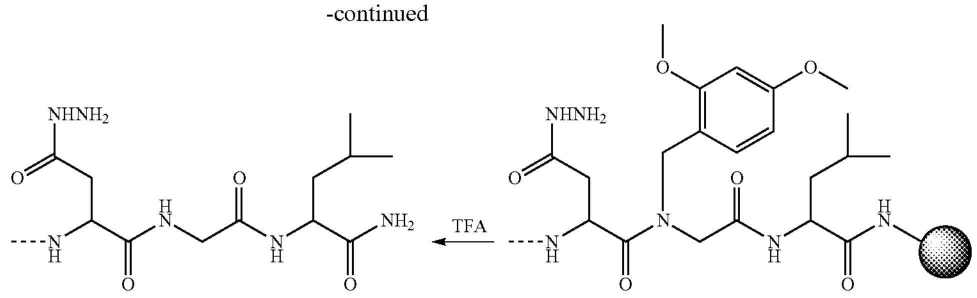

Figure 27:
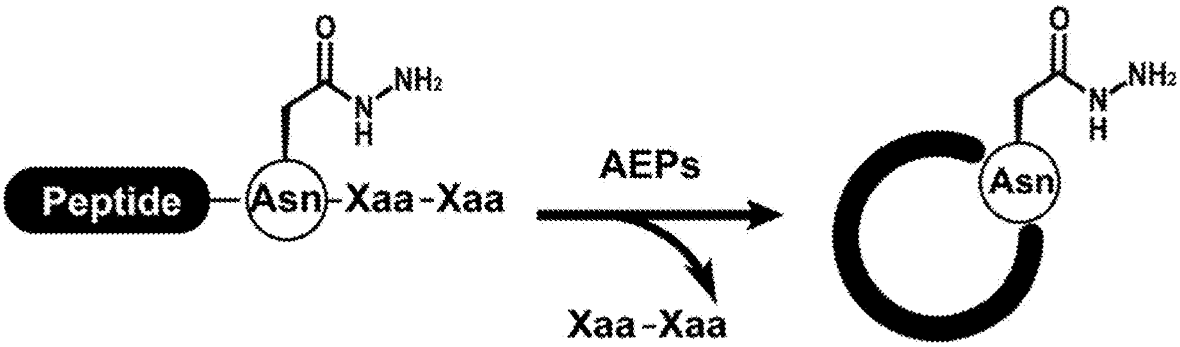
FIG. 27. General scheme of Asn($NH_2$)-mediated peptide cyclization by the transpeptidase activity of the asparaginyl endopeptidase (AEP) class of enzymes.
Figure 28:
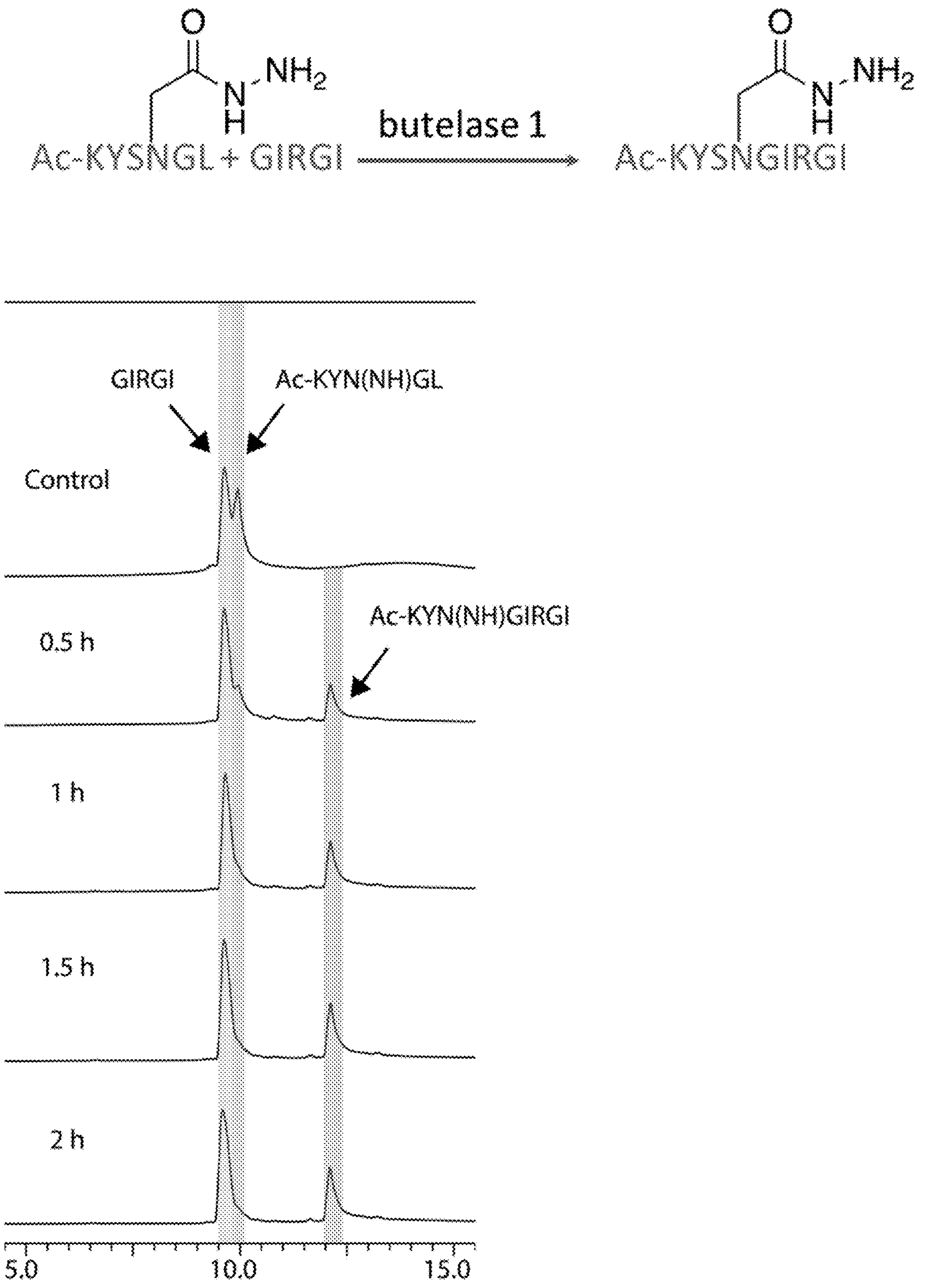
FIG. 28. Demonstration of Asn($NH_2$) as a P1 residue recognized by butelase-1 in an inter-peptide ligation reaction.

For example, Ac-KYSN($NH_2$)GL (SEQ ID NO:43) was synthesized on RINK amide resin using the above method. The synthesized Asn($NH_2$) peptide Ac-KYSN($NH_2$)GL was found to be a good acyl donor substrate in butelase 1-mediated ligation with an acyl acceptor substrate GIRGI (SEQ ID NO:44) (FIG. 28, upper panel). The reaction was conducted using 400 uM of Ac-KYSN($NH_2$)GL and 3.2 mM of GIRGI (8 eq) in the presence of 0.01 eq butelase 1 in 20 mM PBS buffer (pH 6.5) at room temperature. The ligation product was obtained in >80% yield in 1 h (FIG. 28, lower panel). The fact that Asn($NH_2$) can be recognized by butelase 1 as a P1 residue for inter-peptide ligation indicates it can also be used to mediate peptide cyclization (FIG. 27).

All documents referred to herein are incorporated by reference in their entirety.

The invention claimed is:

1. Method for the cyclization of a (poly)peptide comprising an $N^{\gamma}$-hydroxy-L-asparagine (N(OH)) or $N^{\gamma}$-amino-L-asparagine ($N(NH_2)$) residue, the method comprising the steps of:

(i) providing a linear (poly)peptide comprising an $N^{\gamma}$-hydroxy-L-asparagine or $N^{\gamma}$-amino-L-asparagine residue;

(ii) contacting the linear (poly)peptide comprising an $N^{\gamma}$-hydroxy-L-asparagine or $N^{\gamma}$-amino-L-asparagine residue with a peptidyl asparaginyl ligase (PAL) under conditions that allow cleavage of the amino acids C-terminal to the $N^{\gamma}$-hydroxy-L-asparagine or $N^{\gamma}$-amino-L-asparagine residue and ligation of the C-terminus of the $N^{\gamma}$-hydroxy-L-asparagine or $N^{\gamma}$-amino-L-asparagine residue to the N-terminus of the (poly)peptide to cyclize the (poly)peptide.

2. The method of claim 1, wherein the linear (poly)peptide comprising an $N^{\gamma}$-hydroxy-L-asparagine or $N^{\gamma}$-amino-L-asparagine residue comprises or consists of the amino acid sequence $(X)_oN(OH)(X)_p$ or $(X)_oN(NH_2)(X)_p$, with X being any amino acid, o being an integer of 1 or more, preferably 2 or more, p being an integer of 1 or more, preferably of 2 or more, more preferably 2, N(OH) being $N^{\gamma}$-hydroxy-L-asparagine and $N(NH_2)$ being $N^{\gamma}$-amino-L-asparagine.

3. The method of claim 2, wherein $(X)_p$ is $X^3X^4(X)_r$, with $X^3$ being any amino acid with the exception of P, preferably A, C, F, G, H, K, N, Q, R, S, Y, I, preferably H, G, S, N, Q and R, more preferably H, G or S, $X^4$ being a hydrophobic or aromatic amino acid, preferably selected from L, I, V, F, C, W, Y and M, preferably V, L, I and F, and r being 0 or an integer of 1 or more, preferably 0.

4. The method of claim 1, wherein the (poly)peptide comprises the amino acid sequence N(OH)HV or N(OH)GL or N(OH)SL or N(OH)AL or N(OH)IV or $N(NH_2)HV$ or $N(NH_2)GL$ or $N(NH_2)SL$ or $N(NH_2)AL$ or $N(NH_2)IV$, preferably on its C-terminus.

5. The method of claim 1, wherein the (poly)peptide comprises the N-terminal amino acid sequence $X^1X^2$, wherein $X^1$ is G or H and $X^2$ being G, F, L, V or I.

6. The method of claim 1, wherein the PAL is selected from butelase-1, VyPAL2, and OaAEP1b or variants thereof.

7. The method of claim 1, wherein the PAL is VyPAL2 or a variant thereof and the (poly)peptide comprises the amino acid sequence $(X)_oN(OH)X^3X^4(X)_p$ or $(X)_oN(NH_2)X^3X^4(X)_p$, wherein X is any amino acid and o is an integer of at least 2, $X^3$ is G or S, and $X^4$ is a hydrophobic or aromatic amino acid, preferably selected from L, I, V, F, C, W, Y and M, preferably L or F, p is 0 or an integer of 1 or more, N(OH) is $N^{\gamma}$-hydroxy-L-asparagine and $N(NH_2)$ is $N^{\gamma}$-amino-L-asparagine.

8. The method of claim 1, wherein the PAL is butelase-1 or a variant thereof and the (poly)peptide comprises the amino acid sequence $(X)_oN(OH)X^3X^4(X)_p$ or $(X)_oN(NH_2)X^3X^4(X)_p$, wherein X is any amino acid and o is an integer of at least 2, $X^3$ is H, and $X^4$ is a hydrophobic or aromatic amino acid, preferably selected from L, I, V, F, C, W, Y and M, preferably V, p is 0 or an integer of 1 or more, N(OH) is $N^{\gamma}$-hydroxy-L-asparagine and $N(NH_2)$ is $N^{\gamma}$-amino-L-asparagine.

9. The method of claim 1, wherein the PAL is VyPAL2 comprising or consisting of the amino acid sequence set forth in SEQ ID NO:1 or a variant thereof that has an amino acid sequence that has at least 80% sequence identity to the amino acid sequence set forth in SEQ ID NO: 1 over its entire length.

10. The method of claim 1, wherein the PAL is butelase-1 comprising or consisting of the amino acid sequence set forth in SEQ ID NO: 2 or a variant thereof that has an amino acid sequence that has at least 80% sequence identity to the amino acid sequence set forth in SEQ ID NO:2 over its entire length.

11. The method of claim 1, wherein the (poly)peptide to be cyclized is a peptide hormone or therapeutic peptide.

12. The method of claim 1, wherein the (poly)peptide to be cyclized comprises only a single $N^{\gamma}$-hydroxy-L-asparagine or $N^{\gamma}$-amino-L-asparagine residue.

13. The method of claim 1, wherein the (poly)peptide to be cyclized does not comprise any one or more of the sequence motifs NHV, NGL, NSL, preferably does not comprise the amino acid motif $NX^3X^4$, with $X^3$ being any amino acid with the exception of P, preferably A, C, F, G, H, K, N, Q, R, S, Y, I, preferably H, G, S, N, Q and R, more preferably H, G or S, $X^4$ being a hydrophobic or aromatic amino acid, preferably selected from L, I, V, F, C, W, Y and M, preferably V, L, I and F, more preferably does not comprise any N residue.

14. The method of claim 1, wherein the (poly)peptide to be cyclized does not contain any ligation motif for the used PAL other than that comprising the N(OH) or $N(NH_2)$ residue.

15. The method of claim 1, wherein the method further comprises the step of oxidizing the cyclized (poly)peptide to convert the $N^{\gamma}$-hydroxy-L-asparagine or $N^{\gamma}$-amino-L-asparagine residue into L-aspartic acid.

16. Cyclized (poly)peptides obtained according to the method of claim 1 comprising a $N^{\gamma}$-hydroxy-L-asparagine or $N^{\gamma}$-amino-L-asparagine residue.

* * * * *